US012727867B2

(12) United States Patent
Muse et al.

(10) Patent No.: US 12,727,867 B2
(45) Date of Patent: Sep. 8, 2026

(54) TISSUE ENGAGEMENT DEVICES, SYSTEMS, AND METHODS

(71) Applicant: CIRCA SCIENTIFIC, INC., Englewood, CO (US)

(72) Inventors: Jay Muse, Salt Lake City, UT (US); Kevin Jerry Cook, Kaysville, UT (US); Adnan Becic, Sandy, UT (US); Nathaniel Young, Salt Lake City, UT (US); David Willenbrink, Denver, CO (US); Puskar Mishra, Salt Lake City, UT (US)

(73) Assignee: Circa Scientific, Inc., Englewood, CO (US)

( * ) Notice: Subject to any disclaimer, the term of this patent is extended or adjusted under 35 U.S.C. 154(b) by 15 days.

(21) Appl. No.: 18/784,474

(22) Filed: Jul. 25, 2024

(65) Prior Publication Data

US 2024/0374247 A1 Nov. 14, 2024

Related U.S. Application Data

(63) Continuation-in-part of application No. 18/136,284, filed on Apr. 18, 2023, now Pat. No. 12,274,428, (Continued)

(51) Int. Cl.

| | |
|---|---|
| ***A61B 17/02*** | (2006.01) |
| ***A61B 17/34*** | (2006.01) |
| *A61B 17/00* | (2006.01) |

(52) U.S. Cl.
CPC .......... *A61B 17/02* (2013.01); *A61B 17/0218* (2013.01); *A61B 17/3478* (2013.01); (Continued)

(58) Field of Classification Search
CPC ..... A61B 17/02; A61B 17/0218; A61B 17/34; A61B 17/3478; A61B 17/3468; A61B 17/3417; A61M 25/04
See application file for complete search history.

(56) References Cited

U.S. PATENT DOCUMENTS

| | | | | |
|---|---|---|---|---|
| 5,669,885 A * | 9/1997 | Smith | ................ | A61B 17/3496 604/164.01 |
| 6,814,742 B2 * | 11/2004 | Kimura | ............. | A61B 17/1285 606/151 |

(Continued)

*Primary Examiner* — Christopher J Beccia
(74) *Attorney, Agent, or Firm* — Bochner PLLC; Andrew D. Bochner; Ross Brown

(57) ABSTRACT

An embodiment of a tissue engagement device having a sheath, a first arm, a second arm, a first tissue engaging member, a second tissue engaging member, and an actuation cannula. At least a proximal portion of each arm is within the sheath and the tissue engaging members may be positioned on a distal end of each arm. The actuation cannula is also within the sheath, and can move within the sheath between a retracted position and an extended position. The actuation cannula moves at least a portion of each of the first and second arms into a region between an exterior surface of the actuation cannula and an interior surface of the sheath as the actuation cannula moves to the extended position. The engaging members are configured to pierce a desired tissue and anchor to the desired tissue layer when the actuation cannula is in the extended position.

18 Claims, 49 Drawing Sheets

Related U.S. Application Data which is a continuation of application No. 16/841,434, filed on Apr. 6, 2020, now Pat. No. 11,627,951, which is a continuation of application No. 15/361,312, filed on Nov. 25, 2016, now Pat. No. 10,631,840.

(60) Provisional application No. 62/260,212, filed on Nov. 25, 2015.

(52) U.S. Cl.
CPC ............... *A61B 2017/00243* (2013.01); *A61B 2017/00247* (2013.01); *A61B 2017/00349* (2013.01); *A61B 2017/3488* (2013.01)

(56) References Cited

U.S. PATENT DOCUMENTS 10,631,840 B2 * 4/2020 Muse ................. A61B 17/0218
2006/0224165 A1 * 10/2006 Surti ...................... A61B 17/29 606/142

* cited by examiner 100
102
101
120
7A
7A
110
130

166
165
164
160

155b
153b
150b
159b
141

199
198
197
192
191
194a
194b
193
196a
195
196b
149
139
147
190

137
149
193
146
144
145
130
147

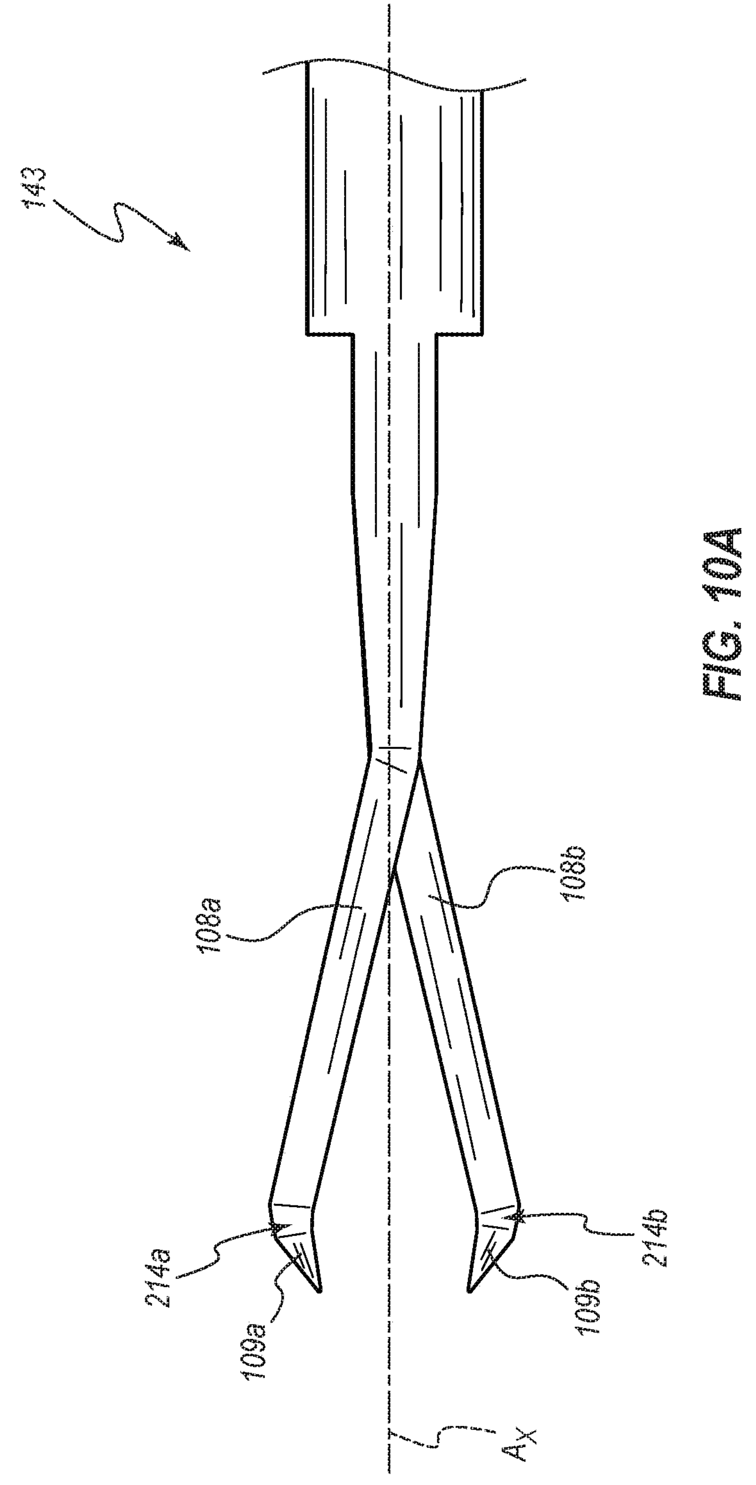
143
108a
108b
214a
214b
109a
109b
AX
FIG. 10A
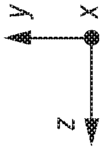
y
x
z 143
108a
108b 347
345
304
300
308a
308b 347
345
304
300
308a
347
308b

TISSUE ENGAGEMENT DEVICES, SYSTEMS, AND METHODS

CROSS-REFERENCE TO RELATED APPLICATIONS

This application is a continuation in part of U.S. patent application Ser. No. 18/136,284, titled TISSUE ENGAGEMENT DEVICES, SYSTEMS, AND METHODS, filed on Apr. 18, 2023, and granted U.S. Pat. No. 12,274,428 which is a continuation of U.S. patent application Ser. No. 16/841,434, titled TISSUE ENGAGEMENT DEVICES, SYSTEMS, AND METHODS, filed on Apr. 6, 2020, and granted U.S. Pat. No. 11,627,951 which is a continuation of U.S. patent application Ser. No. 15/361,312, titled TISSUE ENGAGEMENT DEVICES, SYSTEMS, AND METHODS, filed on Nov. 25, 2016 and granted U.S. Pat. No. 10,631,840 which claims the benefit under 35 U.S.C. § 119(e) of U.S. Provisional Patent Application No. 62/260,212, titled TISSUE ENGAGEMENT DEVICES, SYSTEM, AND RELATED METHODS, filed on Nov. 25, 2015; the entire contents of each of the foregoing applications are hereby incorporated by reference herein

TECHNICAL FIELD

The present disclosure relates generally to systems, devices and methods for providing access to a region beneath a tissue layer. More specifically, the present disclosure relates to devices and methods for accessing the space beneath a tissue layer, which space may be between the tissue layer and an underlying structure (e.g., the pericardial space).

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 10A is a further side elevation view of the engagement element after manufacture of engagement arms;

DETAILED DESCRIPTION

Figure 1:
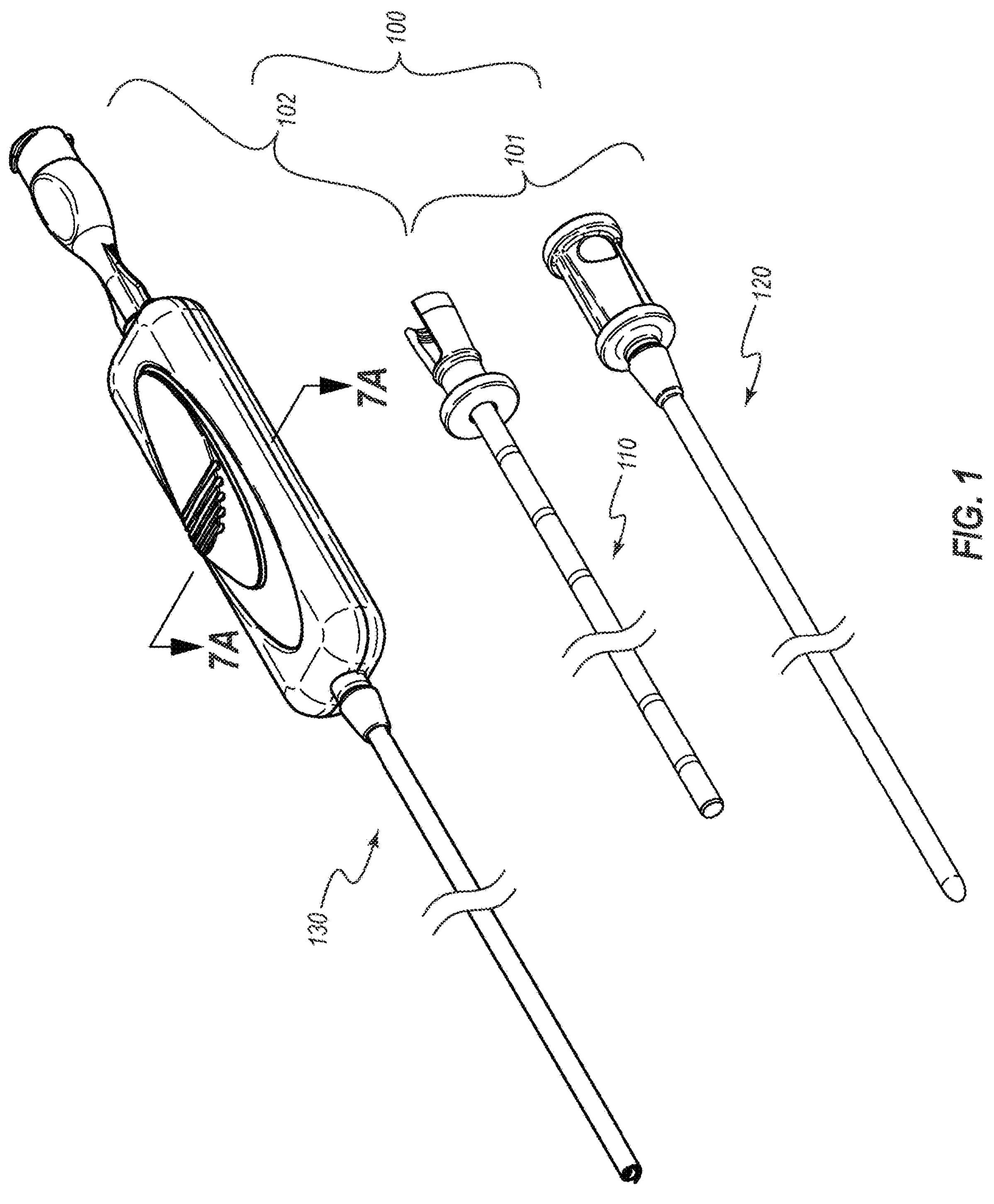
FIG. 1 is a perspective view of an embodiment of a tissue engagement system.

Known systems, devices and methods for providing access to a region beneath a tissue layer, or more particularly, for accessing a space (e.g., the pericardial space or pericardial cavity) between a tissue layer (e.g., the parietal pericardium) and an underlying structure (e.g., the epicardium), suffer from a variety of drawbacks. In the field of cardiac medicine, for example, minimally invasive therapies for treating conditions at the heart's surface, or epicardium, have been developed or contemplated. Example treatments include epicardial ablation, left atrial appendage ligation, lead placement, and drug delivery. An important element of these procedures is safely gaining access to the pericardial space through the pericardium, which is a thin, protective, multi-layer membrane surrounding the heart. The outermost layer is the fibrous pericardium and the inner surface facing the pericardial space is a serous membrane called the parietal layer or pericardium. Opposing the parietal pericardium is another serous membrane called the visceral layer, which forms the outer surface of the epicardium. The pericardial space between the visceral and parietal layers is a thin film of serous fluid that provides lubrication. Because of its close proximity to the epicardium, creating an access port through the very thin pericardium can be difficult without injuring the underlying epicardium, heart muscles (myocardium tissue) and other structures such as blood vessels and nerves. The movement of the beating heart, breathing motions, presence of fatty surface tissue on the external surface of the fibrous pericardium, and toughness of the pericardium are some of the additional factors that can increase access difficulty.

Non-minimally invasive procedures for accessing the pericardial space are considered surgical methods and can use a thorascope to create an opening in the pericardium called a pericardial window. One accepted minimally invasive method for accessing the pericardial space between the pericardium and epicardium for purposes other than draining effusions (pericardiocentesis) involves carefully inserting a needle with fluoroscopic guidance. This procedure, which has been used for many years and is still performed at present, employs a commercially available Tuohy needle (typically 17 gauge or 18 gauge) that accommodates a standard 0.035 inch (8.9 millimeter) guide wire. Other epicardial access procedures are performed with a 21 gauge micropuncture needle which, because of the much smaller diameter, is more benign to unintended heart puncture, but very difficult to use because it is less stiff and requires exchanging to a larger, more stable 0.035 inch (8.9 millimeter) guide wire. Using either needle type requires a high degree of skill and practice, and can be very time-consuming, and therefore this procedure has not been widely adopted, limiting the use of emerging epicardial therapies.

These and other known devices and procedures suffer from a variety of drawbacks, as will be apparent from the disclosure herein. These limitations can be ameliorated or eliminated by embodiments disclosed hereafter.

The present disclosure relates generally to tissue engagement devices, systems, and methods. In particular, certain embodiments disclosed herein can be used for creating or enlarging a space between two tissue layers and, additionally, can be used to access the space.

For purposes of illustration, much of the disclosure herein pertains to creating or enlarging the pericardial space and also accessing this space. Certain devices can engage the pericardium (i.e., the parietal pericardium), which can be pulled away from the heart, or stated otherwise, away from underlying tissue (e.g., the visceral pericardium or epicardium) to expand the pericardial cavity, which may also be referred to as the pericardial space. Enlarging the pericardial space in this manner can reduce the risk of puncturing the underlying tissue (e.g., the epicardium) when a needle is advanced through the pericardium to provide access to this space. Numerous procedures can benefit from providing access to the pericardial space in this manner, such as, for example, collection of pericardial fluid, pericardial biopsy, diagnostic and therapeutic agent delivery, placement of electrical leads, electrophysiology mapping and/or ablation, angioplasty, restenosis reduction, coronary vessel stent placement, coronary vessel bypass grafting, etc. Disclosures provided herein in the context of pericardial access, however, should not be construed as limiting, as other or further embodiments can be used for engaging other tissue layers and providing access to other spaces between tissue layers in a patient.

FIG. 1 is a perspective view of an embodiment of a tissue engagement system 100. As more fully described hereafter, the tissue engagement system 100 can be used to engage a tissue layer and to pierce the tissue layer to provide access to a region beneath the tissue layer. Certain embodiments can be particularly well suited for engaging and piercing tissue layers that are relatively thin and/or are closely situated to an underlying structure. For example, some embodiments are well suited for engaging and piercing the pericardium, and can be configured to do so without contacting or damaging the underlying epicardium. Other features and advantages of various embodiments will be apparent from the disclosure that follows.

In the illustrated embodiment, the tissue engagement system 100 includes a tunneling system 101 and a tissue engagement system 102. Stated otherwise, each of the tunneling system 101 and the tissue engagement system 102 is a subset of the tissue engagement system 100. In the illustrated embodiment, a tunneler cannula 110 is common to both the tunneling system 101 and the tissue engagement system 102. That is, the tunneler cannula 110 can be used with the tunneling system 101 to tunnel a path to a target tissue layer, and can further be used with the tissue engagement system 102 in the subsequent engagement and piercing of the target tissue layer.

In addition to the tunneler cannula 110, the tunneling system 101 includes an obturator 120, and the tunneling system 102 includes a tissue engagement device. In the illustrated embodiment, each of the obturator 120 and the tissue engagement device 130 is configured to be selectively coupled with the tunneler cannula 110.

In some embodiments, the tissue engagement system 100 is provided as a kit 103. For example, the tunneler cannula 110, the obturator 120, and the tissue engagement device 130 can be assembled as a set and distributed together, such as in unitary sterile packaging. In other embodiments, the kit 103 may exclude one or more of the obturator 120 or the tunneler cannula 110. In other instances, one or more of the tunneler cannula 110, the obturator 120, or the tissue engagement device 130 can be distributed separately.

Figure 2:
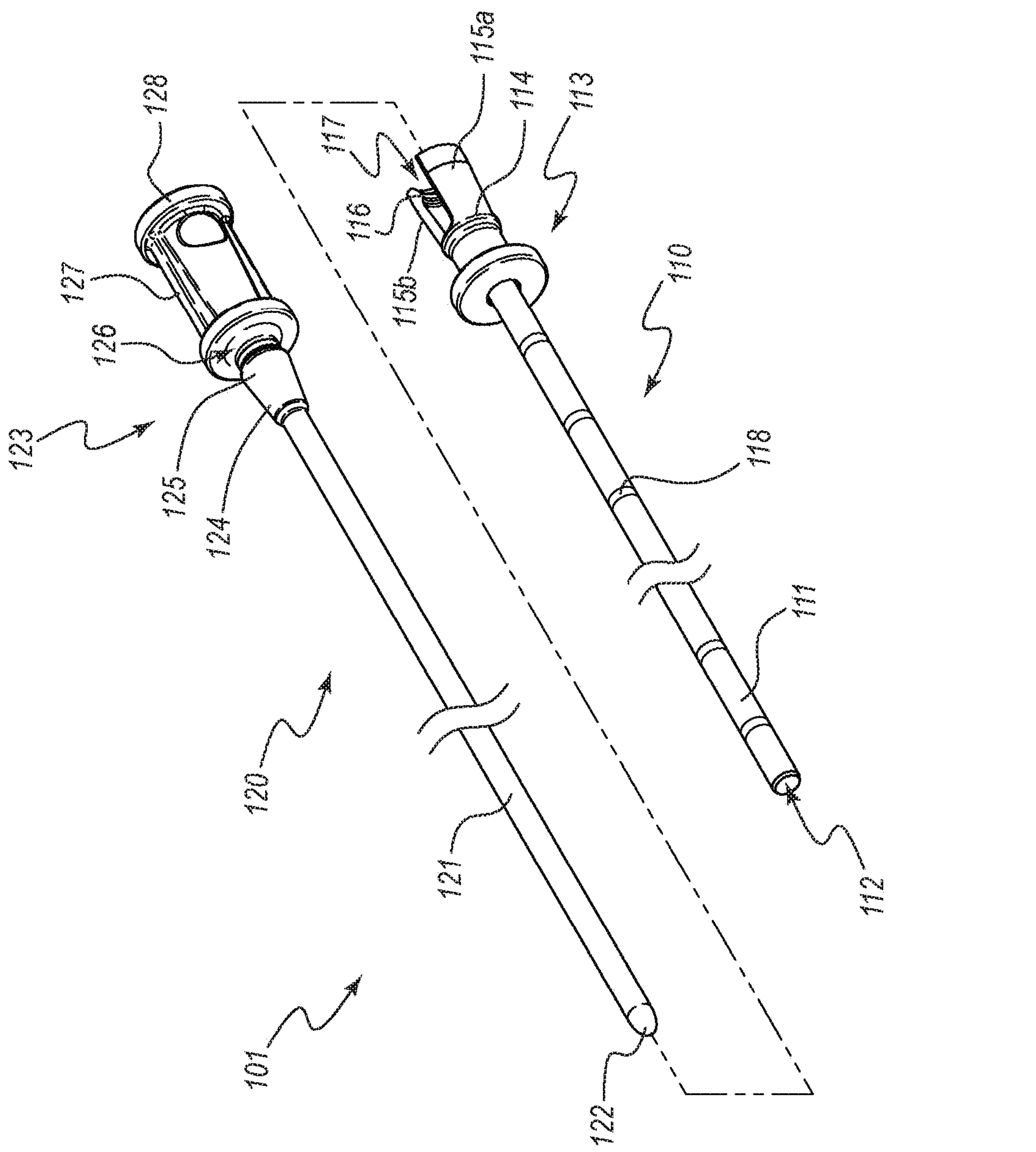
FIG. 2 is a perspective view of an embodiment of a tunneling system that includes an embodiment of a tunneler cannula and an embodiment of an obturator, wherein the depicted tunneling system can be a subset of the tissue engagement system of FIG. 1.

With reference to FIG. 2, the tunneling system 101 is shown in greater detail. In the illustrated embodiment, the tunneler cannula 110 includes a cannula, shaft, or tube 111 that defines a lumen 112.

The tunneler cannula 110 can further include a connector 113 at a proximal end of the tube 111. The connector 113 can be of any suitable variety and can be configured to selectively couple/decouple the tunneler cannula 110 to/from the obturator 120. In the illustrated embodiment, the connector 113 comprises a female snap fitting 114 that includes two resilient prongs 115*a*, 115*b* that are configured to flex outwardly relative to a longitudinal axis of the tunneler cannula 110. A proximal end of each resilient prong 115*a*, 115*b* includes an inwardly directed ridge 116 that can engage a complementary portion of the obturator 120. The illustrated snap fitting 114 includes a pair of diametrically opposed channels 117 (only one of which is shown in FIG. 2). The channels 117 can facilitate flexion of the prongs 115*a*, 115*b*. In some embodiments, the tunneler cannula 110 can include one or more depth markings 118 of any suitable variety.

The illustrated obturator 120 includes a rod 121 that is sized to substantially fill the lumen 112 of the tunneler cannula 110. For example, an outer diameter of the rod 121 can be slightly smaller than an inner diameter of the tube 111 to permit the obturator 120 to be readily inserted into and removed from the tube 111, while still filling the lumen 112 to prevent coring thereby as the tube 111 is advanced through tissue (e.g., soft or connective tissue) of a patient.

As used herein, the term "diameter" is used in its broadest sense, and includes the definition of a straight line from one side of something to the other side that passes through the center point, or the distance through the center of something from one side to the other. That is, the term diameter does not necessarily imply a circular configuration. Although the drawings generally depict circular or cylindrical symmetries, such as for the tube 111 and the rod 121, the present disclosure contemplates non-circular configurations. For example, various embodiments can have non-circular cross-sectional profiles such as triangular, rectangular, polygonal, oval, etc. Unless otherwise specified, the term "diameter" refers to the maximum diameter of a given feature, or portion thereof, as will be apparent from context.

The obturator 120 can include a dull or blunt tip 122 that may be rounded at a distal end thereof. The tip 122 may have a sufficiently steep pitch (e.g., be sufficiently sharp) to permit the obturator 120 to be readily advanced through tissue. In some embodiments, the tip 122 is, nevertheless, sufficiently blunt to prevent inadvertent puncturing or perforation of a target tissue layer when the tip 122 presses against the target tissue layer. For example, in some embodiments, the tip 122 may be readily advanced through tissue of a patient toward the heart of the patient (e.g., by application of about 2 or 3 pounds of force), but when the tip 122 comes into contact with the heart (e.g., the pericardium) with the same amount of force, the tip 122 is stopped thereby and does not puncture the heart.

The obturator 120 can include a connector 123 that is configured to be selectively coupled with the connector 113 of the tunneler cannula 110. The illustrated connector 123 is a male snap fitting 124 that is complementary to the female snap fitting 114 of the tunneler cannula 110. The snap fitting 124 includes an inclined or camming surface 125 that spreads apart the prongs 115*a*, 115*b* until the ridges 116 are received into a groove 126 at a proximal end of the camming surface 125. Any other suitable connection interface between the obturator 120 and the tunneler cannula 110 is contemplated.

In the illustrated embodiment, the obturator 120 includes a pair of diametrically opposed ridges 127, which may act as grips that can permit ready twisting of the tunneling system 101 during a tunneling event. The obturator 120 can include an enlarged base 128, which may be substantially flat, which may facilitate application of distally directed force to the tunneling system 101 during a tunneling event.

Figure 3:
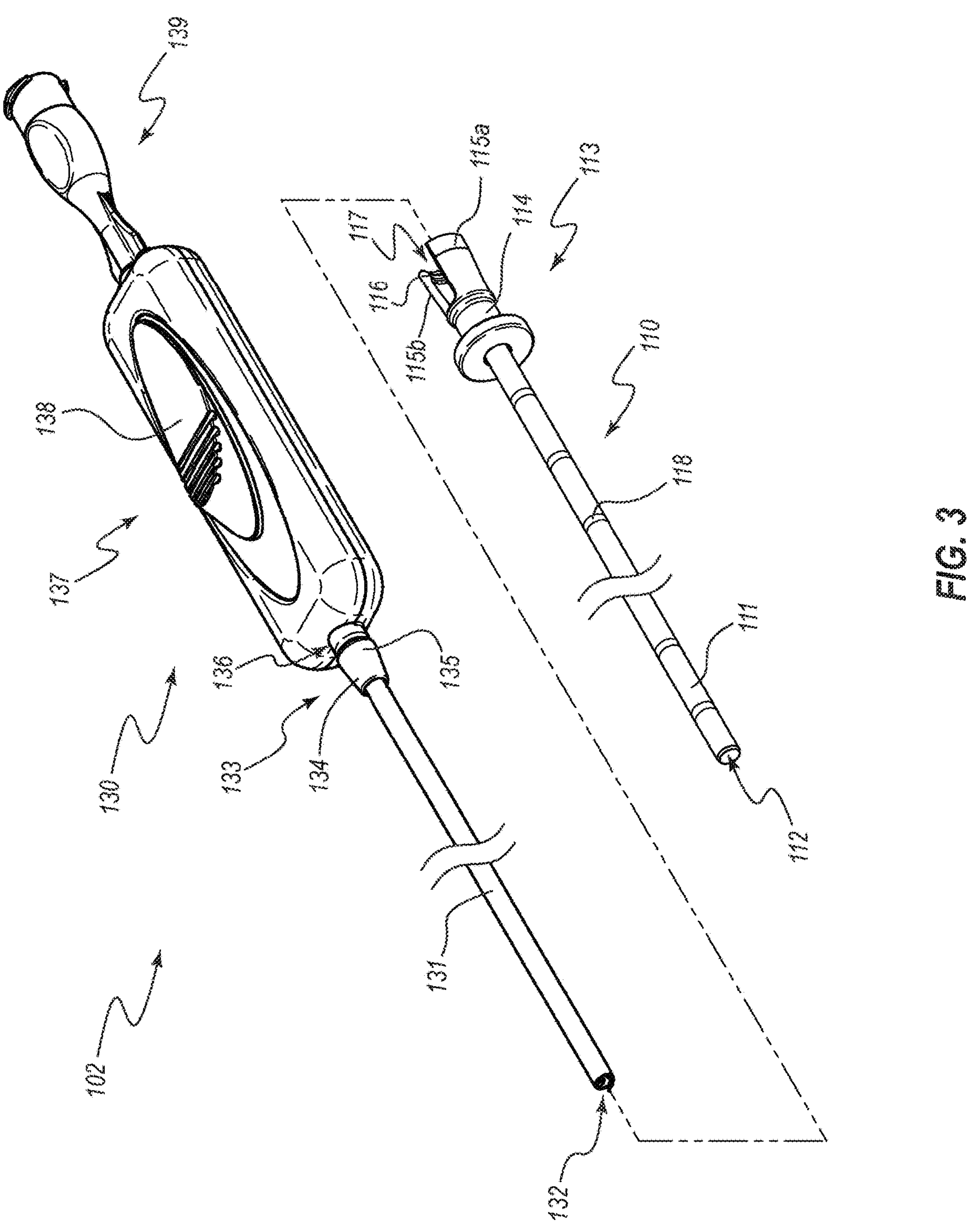
FIG. 3 is a perspective view of an embodiment of a tissue engagement system that includes the tunneler cannula of FIG. 2 and an embodiment of a tissue engagement device, wherein the depicted tunneling system can be a subset of the tissue engagement system of FIG. 1.

With reference to FIG. 3, the tissue engagement device 130 can include coupling features similar or identical to those of the obturator 120. For example, in the illustrated embodiment, the tissue engagement device 130 includes a connector 133 having a camming surface 135 and a groove 136 that are the same as like-numbered, like-named features of the obturator. Accordingly, after a tunneling event, the obturator 120 can be readily removed from the tunneler cannula 110 and replaced with the tissue engagement device 130.

The tissue engagement device 130 can include an elongated housing or sheath 131 that defines a lumen 132. In order to diminish the profile of a distal portion of the tissue engagement system 102 that is inserted in a patient, the sheath 131 can have an outer diameter that is slightly smaller than an inner diameter of the tube 111. Such an arrangement can permit the sheath 131 to be readily inserted into and removed from the tube 111, while providing a large amount of space for components of the tissue engagement device 130 that are housed within the sheath In various embodiments, an outer diameter of the sheath 131 can be no greater than about 0.15, 0.10, or 0.09 inches (3.8, 2.5, or 2.3 millimeters). In some embodiments, the outer diameter of the sheath 131 is about 0.96 inches (2.4 millimeters).

A thickness of a sidewall of the sheath 131 may also be selected to provide the sheath 131 with sufficient stiffness or rigidity to resist bending, while being narrow to provide a large amount of space for the components housed within the sheath 131. In various embodiments, the thickness of the sidewall of the sheath 131 is no greater than about 0.005, 0.004, or 0.003 inches (0.13, 0.1, 0.08 millimeters).

The sheath 131 may be formed of any suitable material. In some embodiments, the sheath 131 comprises stainless steel.

The tissue engagement device 130 can include an actuation mechanism 137 that can include an actuation interface 138 via which a user can deploy a portion of the tissue engagement device 130. In the illustrated embodiment, the actuation interface 138 comprises a button that can be pushed distally to actuate engagement arms or pulled proximally to retract the engagement arms after actuation, as further discussed below. The actuation mechanism 137 can further include an access assembly 139, which can be used to deploy an access device, such as a needle. In the illustrated embodiment, the access assembly 139 can be pushed distally to deploy the needle and can be pulled proximally to retract the needle after deployment, as discussed further below.

Figure 4A:
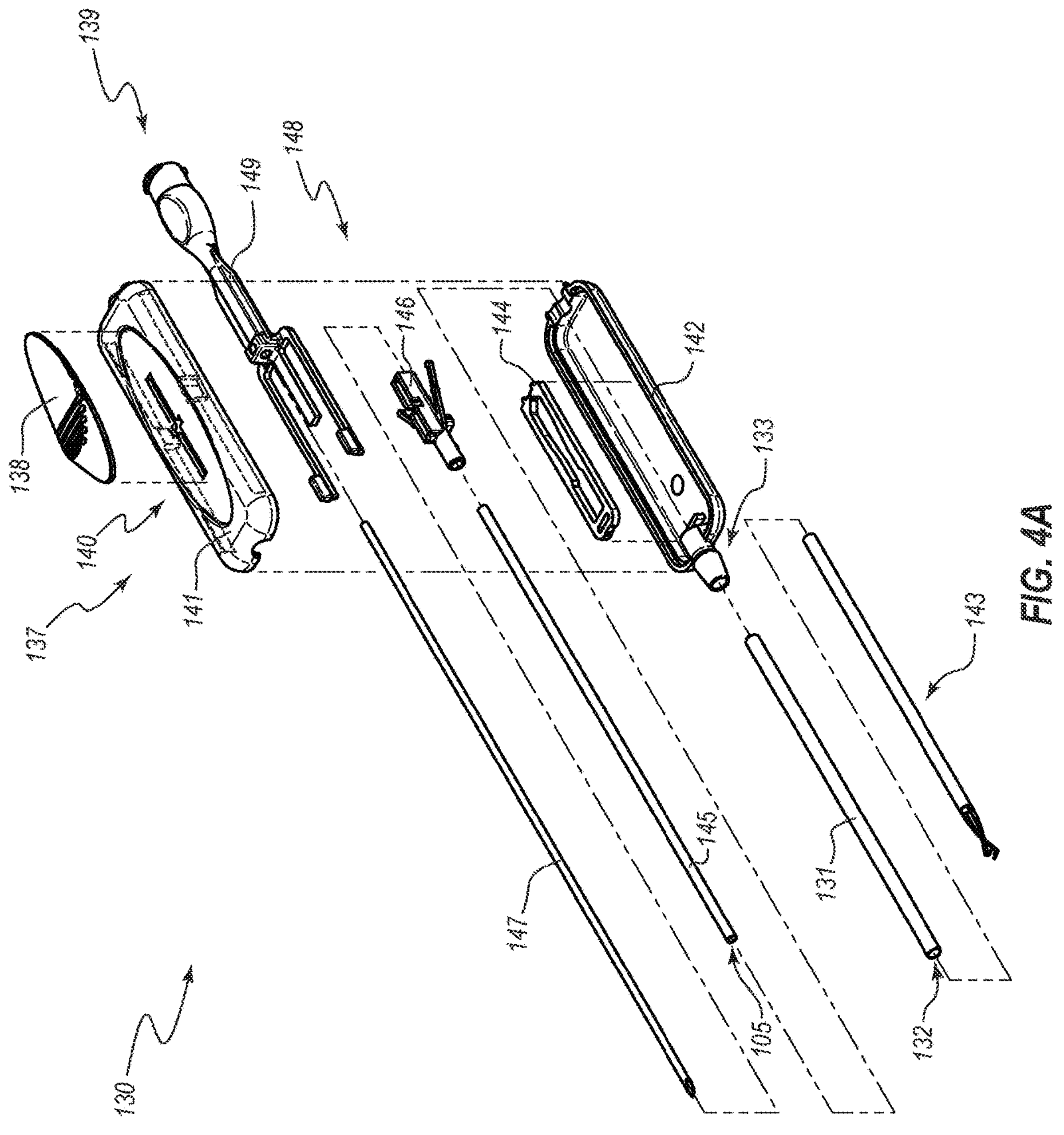
FIG. 4A is an exploded perspective view of the tissue engagement device of FIG. 3.

With reference to FIG. 4A, the actuation mechanism 137 of the tissue engagement device 130 can include a housing 140 within which various components are received. In the illustrated embodiment, the housing 140 includes an upper shell 141 and a lower shell 142. The upper and lower shells 141, 142 can be secured to each other in any suitable fashion, including one or more of friction-fit engagement, snap-fit engagement, adhesive, welding (e.g., ultrasonic welding), etc.

Use of directional terms herein, such as "upper" and "lower," are generally relative to the orientations depicted in the drawings. Such directional terms are not necessarily intended to limit the possible orientations of the devices or components. For example, in some instances, a user may prefer to orient the upper shell 141 downwardly, and the lower shell upwardly 142, during use of the actuation mechanism.

In some embodiments, the assembled housing 140 can be sized to fit within the curvature of one or more curled, clenched, or gripped fingers of a user's hand. For example, an external width of the assembled housing 140 can be no greater than about ½ inch, ⅝ inch, ¾ inch, 1 inch, or 1.5 inches (1.3, 1.6, 1.9, 2.5, or 3.8 centimeters). In some embodiments, the width is about ⅝ inches. In some embodiments, an external length of the assembled housing 140 can simultaneously contact up to 3 or up to 4 curled, clenched, or gripped fingers of one of a user's hands. Such a configuration can provide the user with a firm handle on the housing 140 and can permit stable, reliable, and/or ergonomic usage of the engagement device 130. In various embodiments, a gripping region of the assembled housing (e.g., the substantially parallelepiped central portion of the illustrated embodiment) can have a length that is no greater than about 2, 2.5, or 3 inches (5.1, 6.4, or 7.6 centimeters). In some embodiments, the length is about 2.25 inches.

As further discussed hereafter, the actuation interface 138 can be movably coupled with the housing 140. For example, in the illustrated embodiment, the actuation interface 138 can be configured to be selectively translated distally (for actuation) or proximally (for retraction). A location of the actuation interface 138 relative to the housing 140 can be ergonomically designed for ease of use. In the illustrated embodiment, the actuation interface 138 is configured to pass substantially through a center point of an upper surface of the upper shell 141. The actuation interface 138 may further be configured to move approximately equal distances from the center point in each of the distal and proximal directions. Other suitable configurations are also contemplated. The actuation interface 138 may be conveniently located for single-handed operation thereof. For example, in the illustrated embodiment, the housing can be gripped by multiple fingers of one hand of a user and the actuation interface 138 can be controlled by the thumb of that hand.

The lower shell 142 of the housing 140 can define the connector 133. In the illustrated embodiment, the sheath 131 is fixedly secured to the connector 133 in any suitable manner. An engagement element 143 can be received within the lumen 132 of the sheath 131, and may be fixedly secured to the connector 133 and/or the sheath 131. Stated otherwise, the engagement element 143 can be fixed relative to the sheath 131 and/or relative to the housing 140. In the illustrated embodiment, a proximal end of the engagement element 143 is attached to a proximal end of the sheath 131.

Figure 4B:
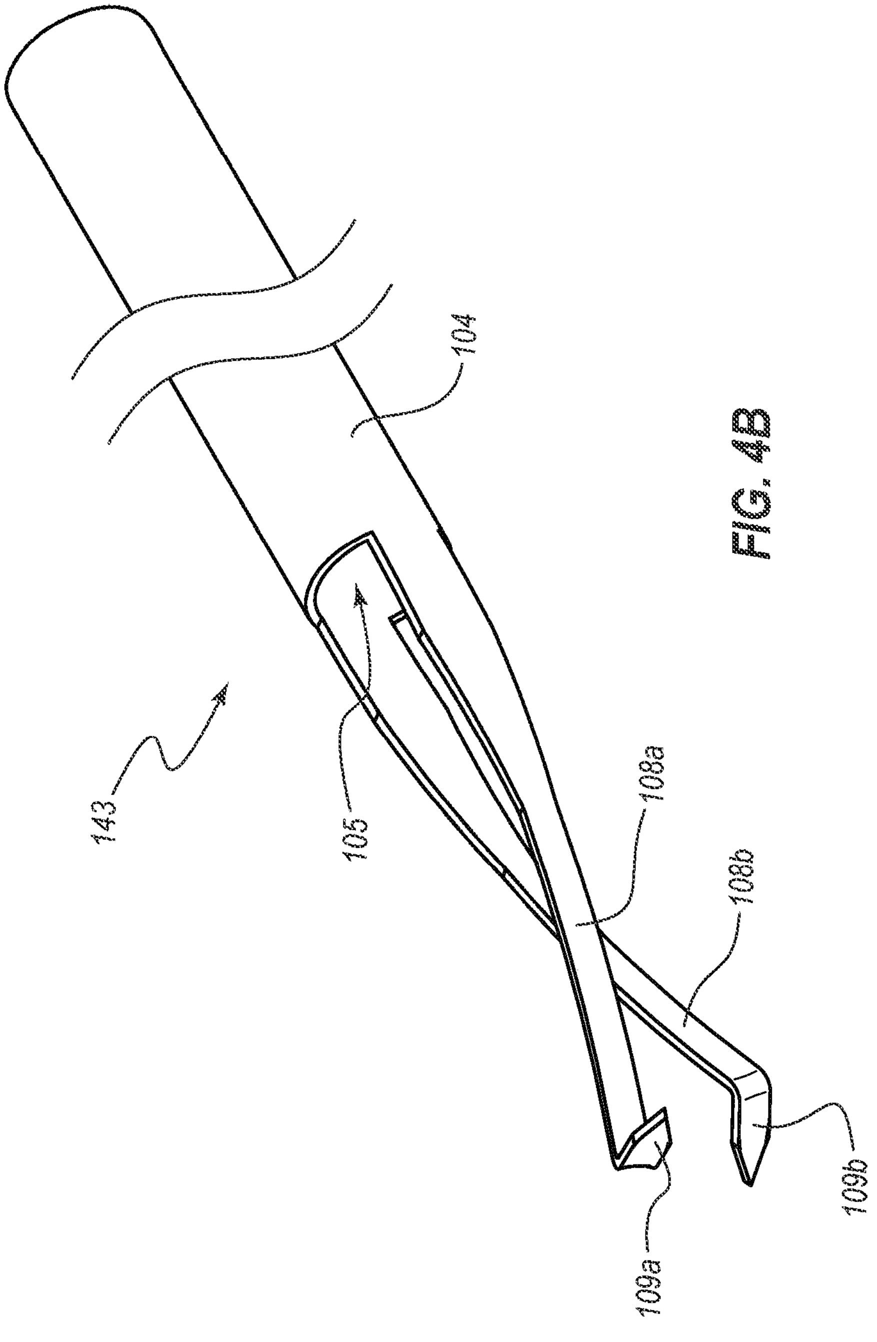
FIG. 4B is an enlarged perspective view of a distal portion of an embodiment of an engagement element.

FIG. 4B depicts a distal portion of the engagement element 143 in greater detail. The engagement element 143 comprises a base 104, which defines the proximal portion of the engagement element 143. In the illustrated embodiment, the base 104 is a substantially tubular or cannular structure, and thus the base 104 may also be referred to as a cannular base. The cannular base 104 defines a lumen 105. In the illustrated embodiment, an outer diameter of the base is slightly smaller than an inner diameter of the sheath 131.

In the illustrated embodiment, a plurality of flexible arms 108*a*, 108*b* extend distally from a distal end of the base 104. The arms 108*a*, 108*b* may also be referred to as tines or prongs. As further discussed below, the arms 108*a*, 108*b* may be integrally connected to the base 104, in some embodiments, or stated otherwise, the base 104 and the arms 108*a*, 108*b* may be integrally formed from a unitary piece of material. For example, the arms 108*a*, 108*b* may be formed by cutting away (e.g., laser cutting) portions of a tube (see FIG. 9) and then bending the remaining protrusions. In some embodiments, prior to insertion of the engagement element 143 into the sheath 131, the arms 108*a*, 108*b* may retain a bent configuration that extends transversely outward beyond an outer perimeter of the base 104, such as, for example, the configuration depicted in FIGS. 10A and 10B.

Each arm 108*a*, 108*b* can include a tissue engaging member 109*a*, 109*b* that can embed within, pierce, or otherwise attach to a target tissue layer. The tissue engaging members can each include a pointed element, such as an angled end, spike, or barb, that can pierce into the target tissue layer. In the illustrated embodiment, each tissue engaging member 109*a*, 109*b* includes an angled distal end of the respective arm 108*a*, 108*b*.

With reference again to FIG. 4A, the engagement device 130 can include an actuation member 145 that communicates movement of the actuation interface 138 at a proximal end thereof to a distal end of the actuation member 145. As further discussed below, the actuation member 145 can be configured to deploy the arms 108*a*, 108*b* of the engagement element 143. In some embodiments, such as that illustrated in FIG. 4A, the actuation member 145 comprises a tube or cannula. Accordingly, the actuation member 145 may also be referred to as an actuation cannula.

Further, the illustrated embodiment includes a piercing member or access device 147 that is configured to create an access opening through the target tissue layer when deployed. In the illustrated embodiment, the access device 147 is a needle. Any suitable needle or other piercing member may be used. The actuation member 145 can be positioned within the lumen 132 of the sheath 131, and can be sized to slide or otherwise translate freely therein. The access device 147 can be positioned within the lumen 105 of the actuation member 145, and can be sized to slide or otherwise translate freely therein.

The actuation mechanism 137 can include multiple components that are configured to constrain operation of the tissue engagement device 130. In particular, in the illustrated embodiment, the actuation mechanism 137 includes components that control the movement of the actuation member 145 relative to the engagement element 143, and also relative to the access device 147. Further, the actuation mechanism 137 includes components that control the movement of the access device 147 relative to the actuation member 145 and the engagement element 143. In the illustrated embodiment, the actuation mechanism includes a gate 144 that is received within the lower shell 142 of the housing, a shuttle 146 that is coupled with the actuation member 145, and a hub 149 that is coupled with the access device 147. At least a portion of each of these components is positioned within the housing 140. Various features of these components and their functions are discussed further below with respect to FIGS. 6A-7E. The access assembly 139 includes the hub 149 and the access device 147. The actuation interface 138, the shuttle 146, and the actuation member 145 may be referred to collectively herein as an actuation assembly 148.

FIGS. 5A-5D depict the tissue engagement system 102 in various operational states, which can correspond with method steps for using the system 102. These figures depict a distal end of the assembled engagement system 102. Although illustrative examples for achieving the operational states depicted in FIGS. 5A-5D can be achieve via the illustrated actuation mechanism 137, as described further below with respect to FIGS. 6A-7E, it should be understood that any suitable systems and methods for achieving the operational states discussed are contemplated.

Figure 5A:
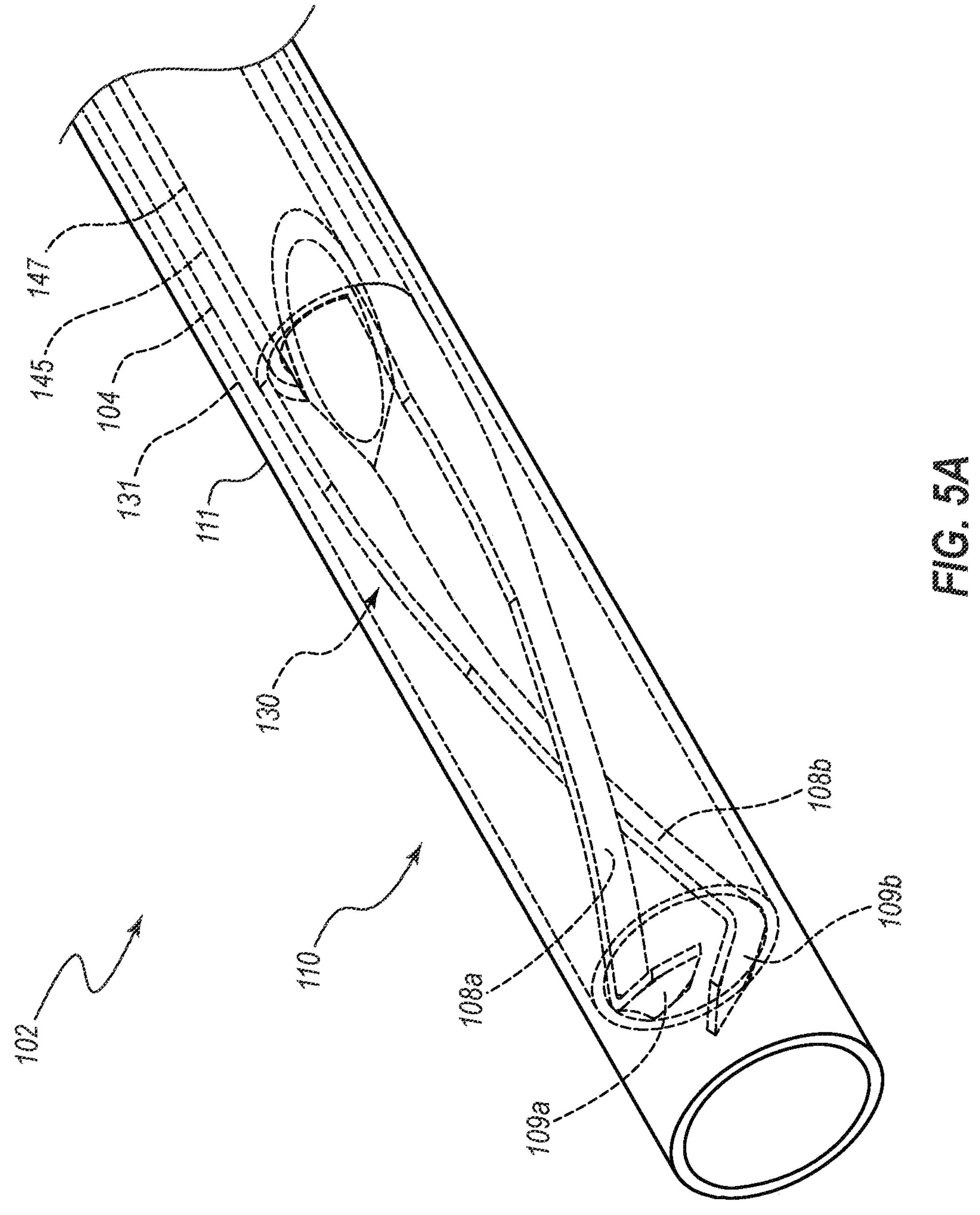
FIG. 5A is an enlarged partial perspective view of a distal portion of the tissue engagement device positioned within a distal portion of the tunneler cannula.

FIG. 5A depicts a distal portion of the tissue engagement device 130 positioned within a distal portion of the tunneler cannula 110. The tube 111 of the tunneler cannula is shown as the outermost tube. The outer surfaces of the sheath 131, the cannular base 104, the actuation member 145, and the access device 147 are depicted in broken lines. This view depicts the compact configuration achieved by the nested, telescopic, or coaxial arrangement of the tube 111, the sheath 131, the cannular base 104, the actuation member 145, and the access device 147.

The arms 108*a*, 108*b* and the tissue engaging members 109*a*, 109*b* are also identified in FIG. 5A. In this operational configuration of the tissue engagement system 102, the tissue engagement device 130 may either be in the process of being advanced distally toward or through a distal end of the tube 111 or retracted proximally through the tube 111. In either case, the pointed ends of the tissue engaging members 109*a*, 109*b* are at an interior of the tube 111, or stated otherwise, are within the lumen 112. In this arrangement, the pointed ends cannot inadvertently contact tissue (i.e., tissue at an exterior of the tube 111) during advancement through the tube 111 or retraction through the tube 111.

Figure 5B:
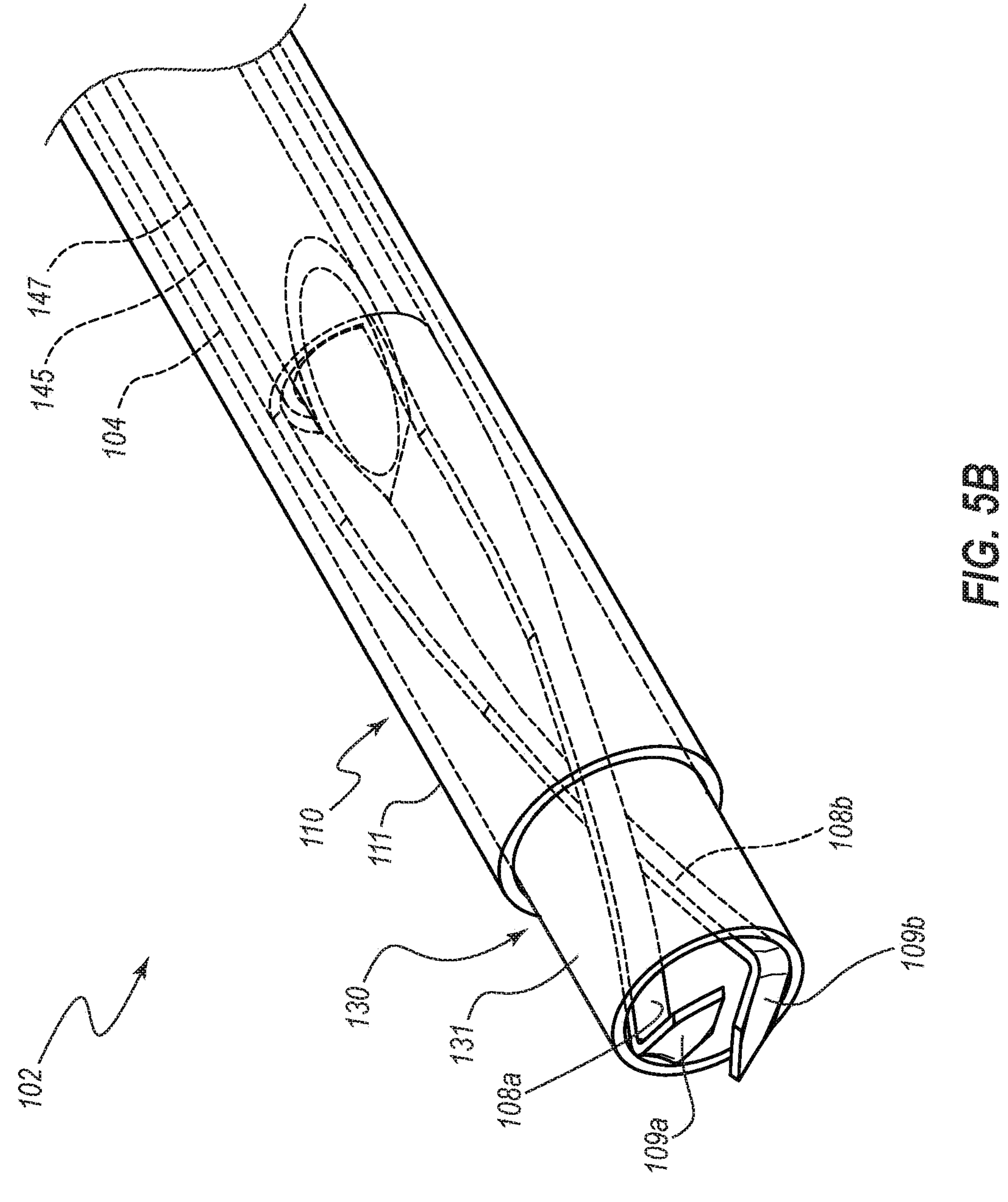
FIG. 5B is an enlarged partial perspective view, such as that of FIG. 5A, that depicts the distal portion of the tissue engagement device advanced past a distal end of the tunneler cannula, wherein the tissue engagement device is in a fully retracted or unactuated state in which engagement arms and an access device are retracted.

FIG. 5B depicts the distal end of the tissue engagement device 130 advanced past a distal end of the tube 111 of the tunneler cannula 110. As with FIG. 5A, the tissue engagement device 130 is depicted in a fully retracted or unactuated state. In the fully retracted state, neither the arms 108*a*, 108*b* nor the access device 147 is deployed. The illustrated configuration can represent a point in time after the system 102 has been advanced to the target tissue layer and just before deployment of the arms 108*a*, 108*b*.

In the illustrated embodiment, the engaging members 109*a*, 109*b* of the arms 108*a*, 108*b* are positioned slightly external to a distal end of the sheath 131 when the tissue engagement device 130 is in the fully retracted configuration. Stated otherwise, the engaging members 109*a*, 109*b* are positioned distally relative to a distal end of the sheath 131. The exposed pointed tips of the engaging members 109*a*, 109*b* may readily engage a target tissue layer upon contact therewith as the distal end of the sheath 131 is advanced into contact with the target tissue layer. Indeed, in the illustrated embodiment, the pointed tips are directed in a slightly distal direction, such that initial contact of the pointed tips with the target tissue layer as the engagement device 130 is advanced distally through the tunneler cannula 110 can urge the pointed tips into the target tissue layer. Further, due to the slight exposure of the pointed tips past the distal end of the sheath 131, abutting contact of the distal end of the sheath 131 against the target tissue layer can provide tactile feedback to the user that the tissue layer has been initially engaged and that deployment of the arms 108*a*, 108*b* can proceed.

Figure 11A:
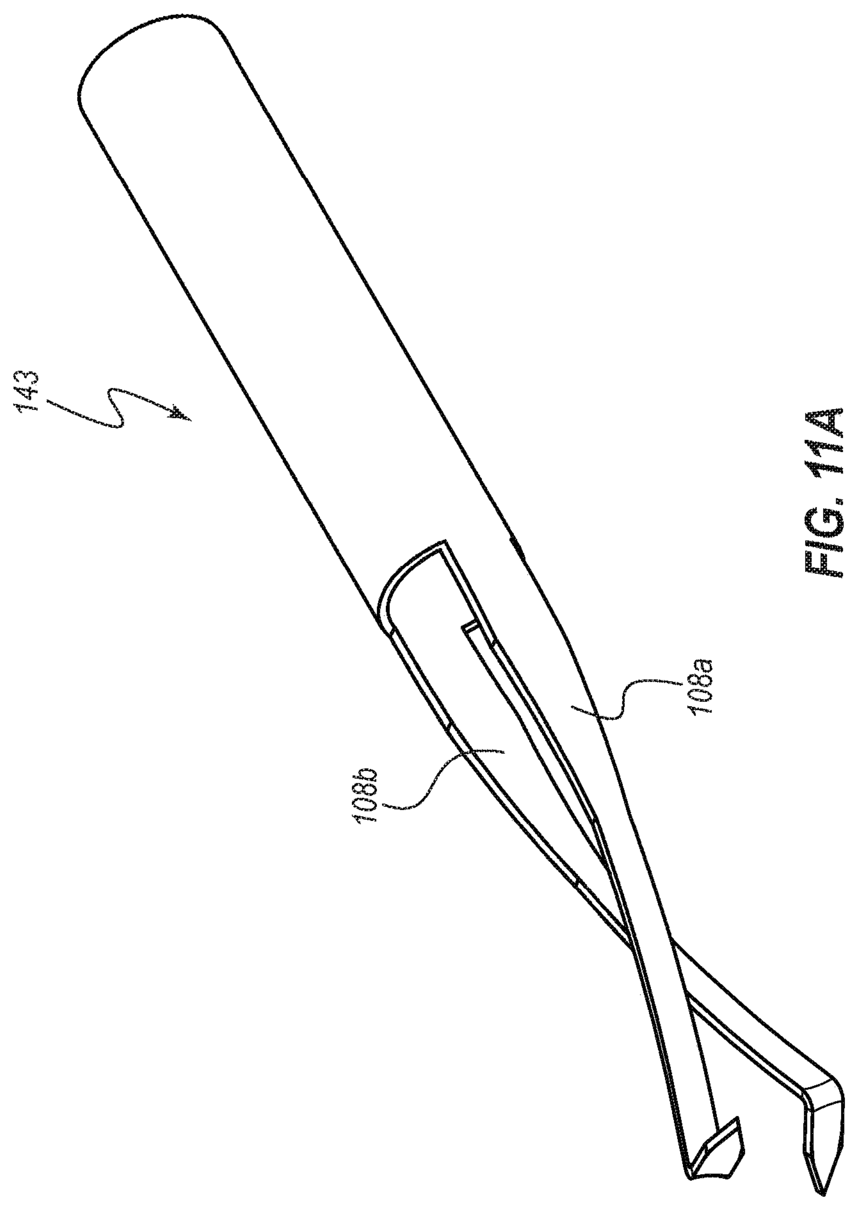
FIG. 11A is a perspective view of the engagement element in a constrained state, such as may be provided by a sheath—not shown in the present view (but see, e.g., FIG. 5B)
Figure 11B:
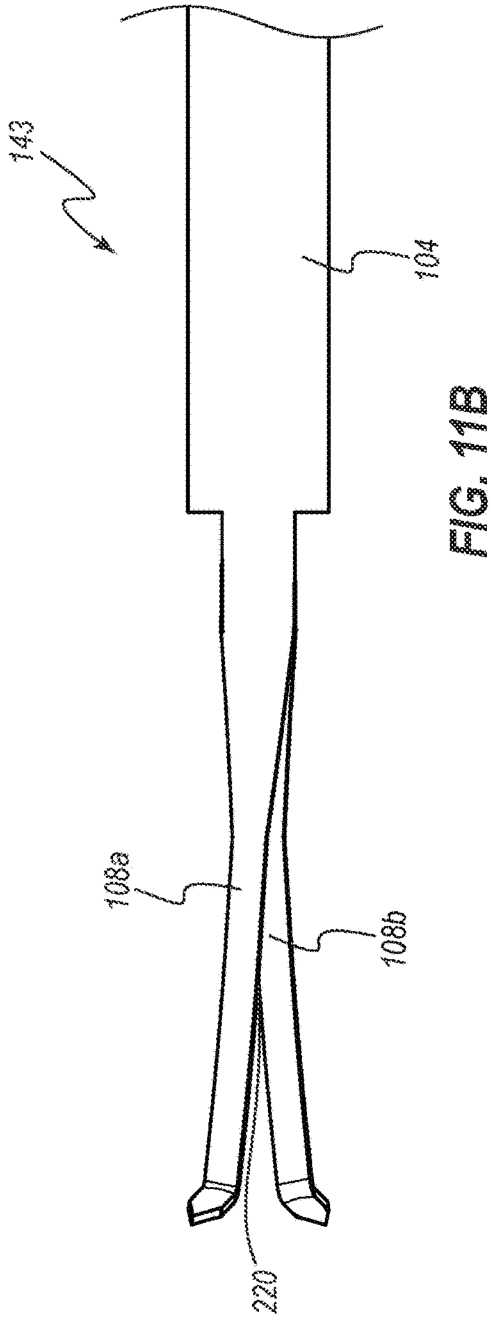
FIG. 11B is a side elevation view of the engagement element in the constrained state.
Figure 11C:
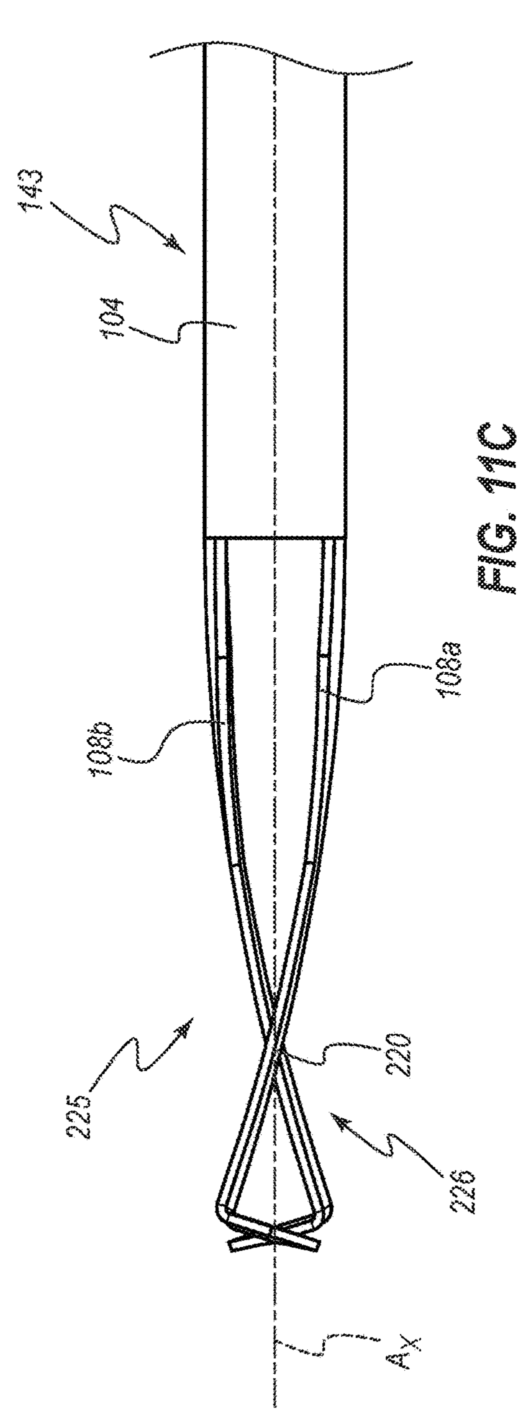
FIG. 11C is a top plan view of the engagement element in the constrained state.
Figure 11D:
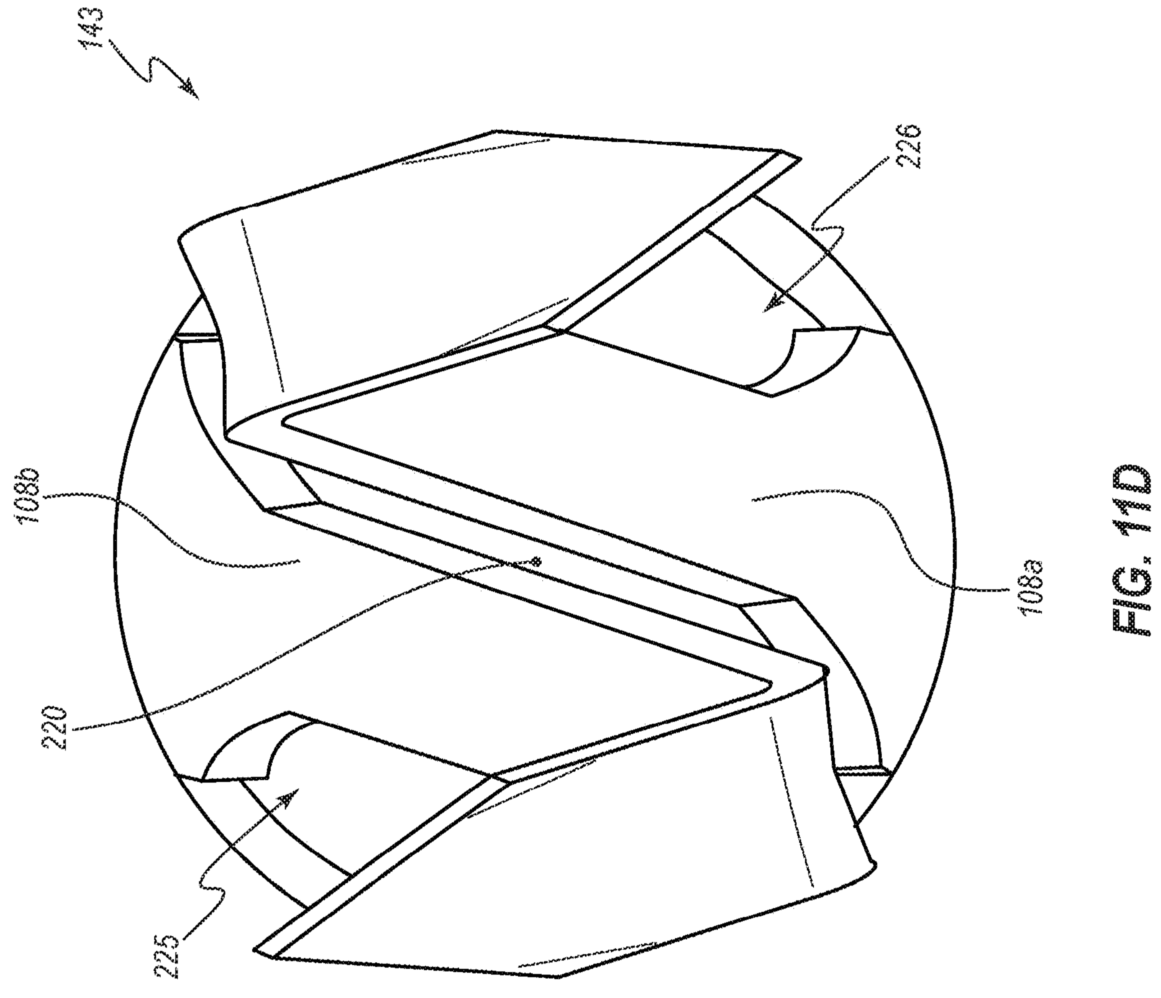
FIG. 11D is a front elevation view of the engagement element in the constrained state.

Although the engaging members 109*a*, 109*b* in the illustrated embodiment extend in a longitudinal direction, or distally, beyond the distal tip of the sheath 131, the engaging members 109*a*, 109*b* are nevertheless restrained to a low-profile configuration in which they either do not extend or do not significantly extend laterally outward beyond a perimeter of the sheath 131. For example, if the arrangement depicted in FIG. 5B were shown in an end-on view (directed proximally), similar to the view depicted in FIGS. 11D and 13, the full perimeter of the distal end of the sheath 131 would be visible in situations where the engaging members 109*a*, 109*b* do not extend laterally outward beyond the perimeter. In this view, the engaging members 109*a*, 109*b* would appear to be interior to the perimeter. Stated otherwise, if an outer surface of the sheath 131 were projected distally beyond the distal end of the sheath 131, either all or substantially all (e.g., no less than 75 percent) of the engaging members 109*a*, 109*b* would be encompassed or circumscribed thereby. Such an arrangement can inhibit or avoid interaction (e.g., snagging, tearing, etc.) between the engaging members 109*a*, 109*b* and tissue that is positioned outside the perimeter of the sheath 131. This can be advantageous either during deployment of the tissue engagement device 130 beyond the distal end of the tunneler cannula 110 or during retraction of the engagement device 130 into the tunneler cannula 110.

The remainder of the arms 108*a*, 108*b* are positioned within the lumen 132 of the sheath 131. As discussed further below, and as depicted in FIG. 5B, the arms 108*a*, 108*b* cross each other at a position that is within the lumen 132 and that is distal to a distal end of the actuation member 145.

Figure 5C:
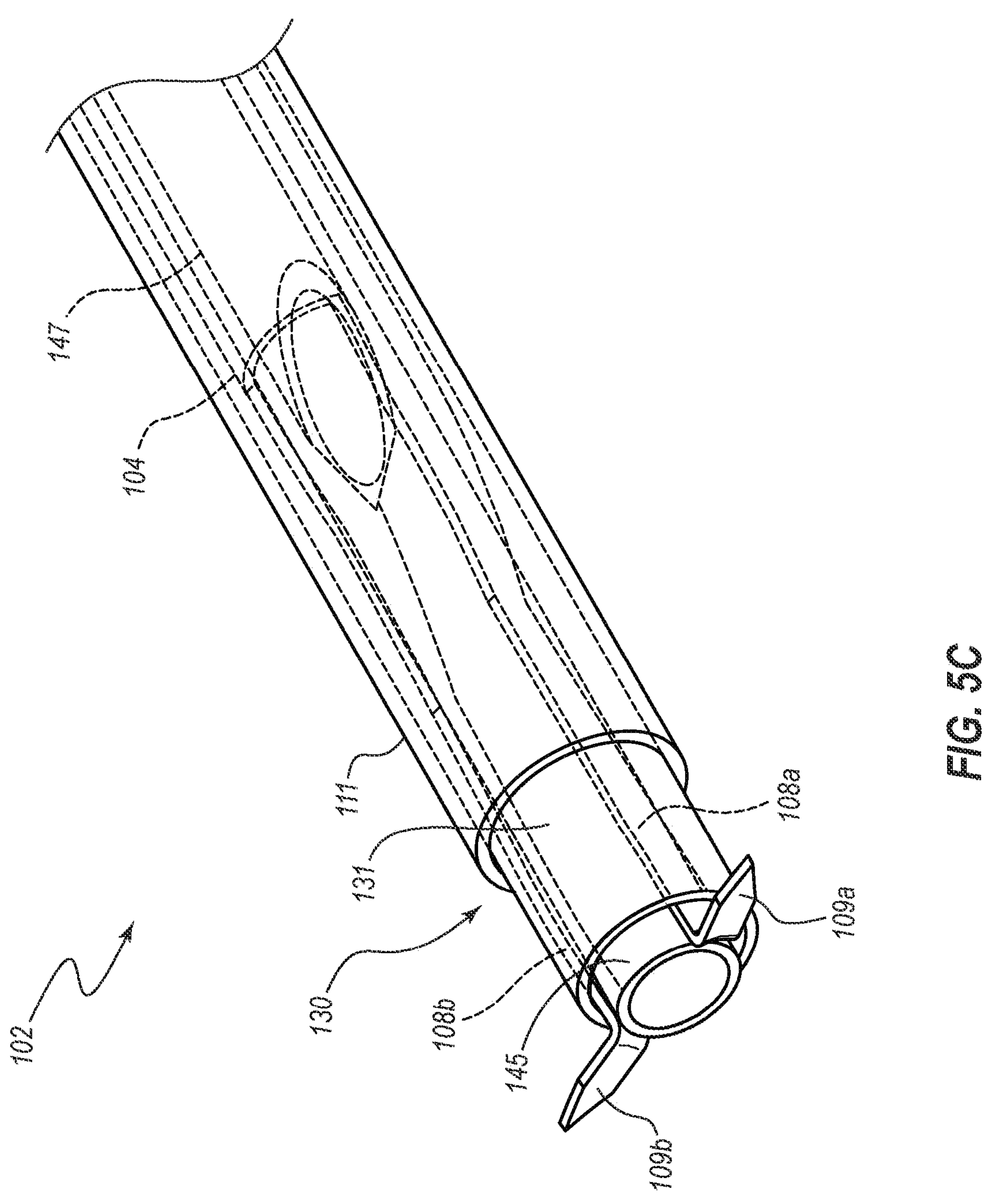
FIG. 5C is an enlarged partial perspective view, such as that of FIGS. 5A and 5B, that depicts the tissue engagement device in a partially deployed state in which the engagement arms are deployed and the access device remains retracted.

FIG. 5C depicts the tissue engagement system 102 after the arms 108*a*, 108*b* have been deployed. In particular, the actuation member 145 has been advanced distally beyond the position at which the arms 108*a*, 108*b* crossed each other, thereby uncrossing the arms 108*a*, 108*b* and deforming them from the undeployed configuration depicted in FIG. 5B. The actuation member 145 has forced a proximal portion of the arms 108*a*, 108*b* into an annular region between an outer surface of the actuation member 147 and an inner surface of the sheath 131.

In the illustrated embodiment, the arms 108*a*, 108*b* are at diametrically opposite sides of the device 130 (e.g., at opposite sides of the cannular base 104). As further discussed below, deployment of the arms 108*a*, 108*b* moves the engaging members 109*a*, 109*b* in substantially opposite directions. The engaging members 109*a*, 109*b* thus can embed within and/or apply tension to the target tissue layer in substantially opposite directions. The arms 108*a*, 108*b* are in a high-profile configuration in which they extend laterally outwardly beyond a perimeter of the sheath 131.

In the illustrated configuration, the tissue engagement device 130 is in a partially deployed state, in that the arms 108*a*, 108*b* are deployed, but the access device 147 remains retracted. Deployment of the arms 108*a*, 108*b* clears the engaging members 109*a*, 109*b* away from the distal end of the actuation member 145 to provide an unobstructed passageway for deployment of the access device 147. Stated otherwise, in the configuration depicted in FIG. 5B, the arms 108*a*, 108*b* cover a distal end of the actuation member 145. Deployment of the arms 108*a*, 108*b* effectively uncovers the distal end of the actuation member 145 to provide an access pathway for the access device 147.

As used herein, the term "cover" does not require direct contact against a surface (e.g., the distal end of the actuation member 145), although such an arrangement is subsumed within this term. The term "cover" is used more broadly herein, and includes situations of obstruction without direct contact. For example, if the arrangement depicted in FIG. 5B were shown in an end-on view (directed proximally), similar to the view depicted in FIG. 13, rather than perspective, much of the opening in the distal end of the actuation member 145 would be obstructed from view by the arms 108*a*, 108*b*. Of more pertinence, viewed in the opposite direction-namely, from the perspective of the distal end of the access device 147, the distal opening of the actuation member 145 would appear to be obstructed. Stated otherwise, if an inner surface of the actuation member 145 that defines the distal opening of the actuation member 145 were projected distally beyond the distal end of the actuation member 145, the arms 108*a*, 108*b* would be encompassed or circumscribed thereby.

In some embodiments, the actuation mechanism 137 can prevent deployment of the access device 147 prior to deployment of the arms 108*a*, 108*b* via the actuation member 145. This can be a safety measure to ensure that the user does not inadvertently partially deploy the arms 108*a*, 108*b* by moving the access device 147 distally past the arms. That is, because the outer diameter of the access device 147 is only slightly smaller than the outer diameter of the actuation member 145, deployment of the access device 147 prior to deployment of the actuation member 145 could extend the engaging members 109*a*, 109*b* laterally outwardly to a relatively high-profile configuration, though potentially not quite as wide or as high-profile an arrangement as can be achieved by deployment of the actuation member 145.

Figure 5D:
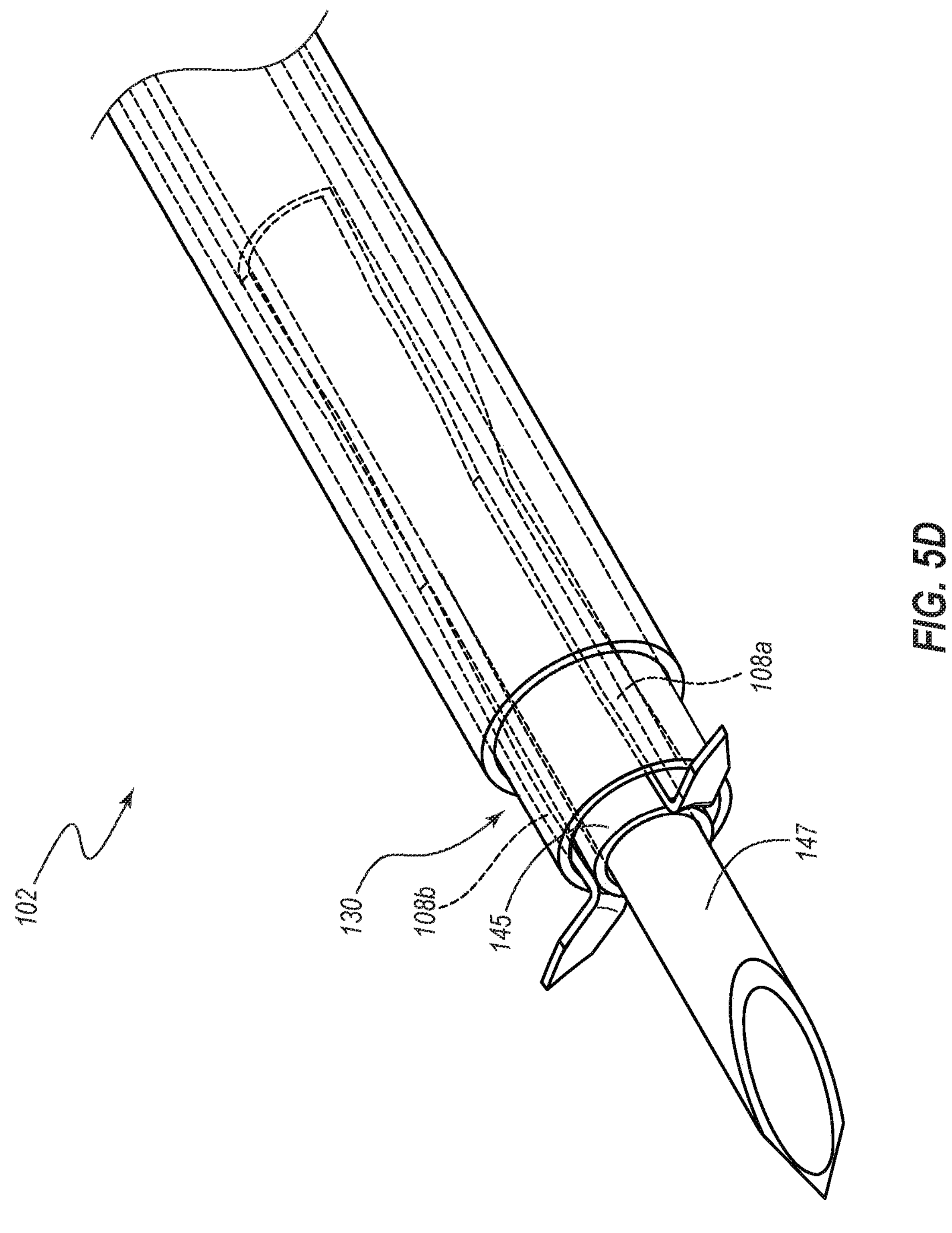
FIG. 5D is an enlarged partial perspective view, such as that of FIG. 5A-5C, that depicts the tissue engagement device in a fully deployed state in which the engagement arms are deployed and the access device is deployed.

FIG. 5D depicts the tissue engagement device 130 in a fully deployed state. In particular, the engagement arms 108*a*, 108*b* are deployed and the access device 147 is also deployed. The access device 147 has been advanced distally through the actuation member 145 and beyond the distal end thereof.

In some embodiments, the actuation mechanism 137 can prevent the actuation member 145 from retracting the engagement arms 108*a*, 108*b* unless the access device 147 is first retracted. This can serve as a safety precaution, as retraction of the actuation member 145 without first retracting the access device 147 could leave the arms 108*a*, 108*b* in a partially deployed state. For example, in the illustrated embodiment, the access device 147 has an outer diameter that is slightly smaller than an outer diameter of the actuation member 145. Thus, if the actuation member 145 were to be withdrawn while the access device 147 is in the deployed state, the resilient arms 108*a*, 108*b* would begin to return to the low-profile configuration upon retraction of the actuation member 145, but would be prevented from reaching this configuration by instead coming into contact with the outer surface of the access device 147. The user could potentially think that the arms 108*a*, 108*b* had been fully retracted at this stage, due to the retraction of the actuation member 145, and could withdraw the tissue engagement device 130 with the arms 108*a*, 108*b* in the partially deployed state. Distal movement of the tissue engagement device 130 in this state could potentially damage the target tissue layer, overlying tissue, and/or the engagement device 130 itself.

In certain embodiments, a method of retracting the system 102 from a patient can follow the stages depicted in FIGS. 5A-5D in reverse order. For example, beginning with the configuration depicted in FIG. 5D, the access device 147 can be retracted to the orientation depicted in FIG. 5C. Thereafter, the actuation member 145 can be retracted to the orientation depicted in FIG. 5B. In certain embodiments, due to resilience of the arms 108*a*, 108*b*, this retraction of the actuation member 145 will also case the arms 108*a*, 108*b* to naturally or automatically return from the deformed condition in FIG. 5C to the configuration depicted in FIG. 5B. Thereafter, the tissue engagement device 130 can be withdrawn through the lumen of the tunneling cannula 110, as depicted in FIG. 5A.

FIGS. 6A-6G depict an illustrative embodiment of the actuation mechanism 137 for the tissue engagement device 130. As previously mentioned, other suitable mechanisms are also contemplated and are within the scope of the present disclosure. The illustrated actuation mechanism 137 is capable of preventing two potentially undesirable configurations of the tissue engagement device 130. In particular, the actuation mechanism 137 is configured to prevent the access device 147 from being deployed prior to deployment of the arms 108*a*, 108*b* via the actuation member 145, which can avoid the potentially undesirable results for such a configuration discussed above. The illustrated actuation mechanism 137 is further configured to prevent retraction of the actuation member 145 and the resultant retraction of the arms 108*a*, 108*b*, which can avoid the potentially undesirable results for such a configuration discussed above. The illustrated actuation mechanism 137 may be referred to as a dual interlock system or as a locking mechanism. Stated otherwise, the actuation mechanism 137 can serve as a lock to prevent a first potentially undesirable configuration of the tissue engagement device 130, and can further serve as a lock to prevent a second potentially undesirable configuration of the tissue engagement device 130. In other embodiments, an interlock device may prevent only one of the potentially undesirable configurations. In still other embodiments, the actuation mechanism 137 may not function as an interlock device for either potentially undesirable configuration.

Figure 6A:
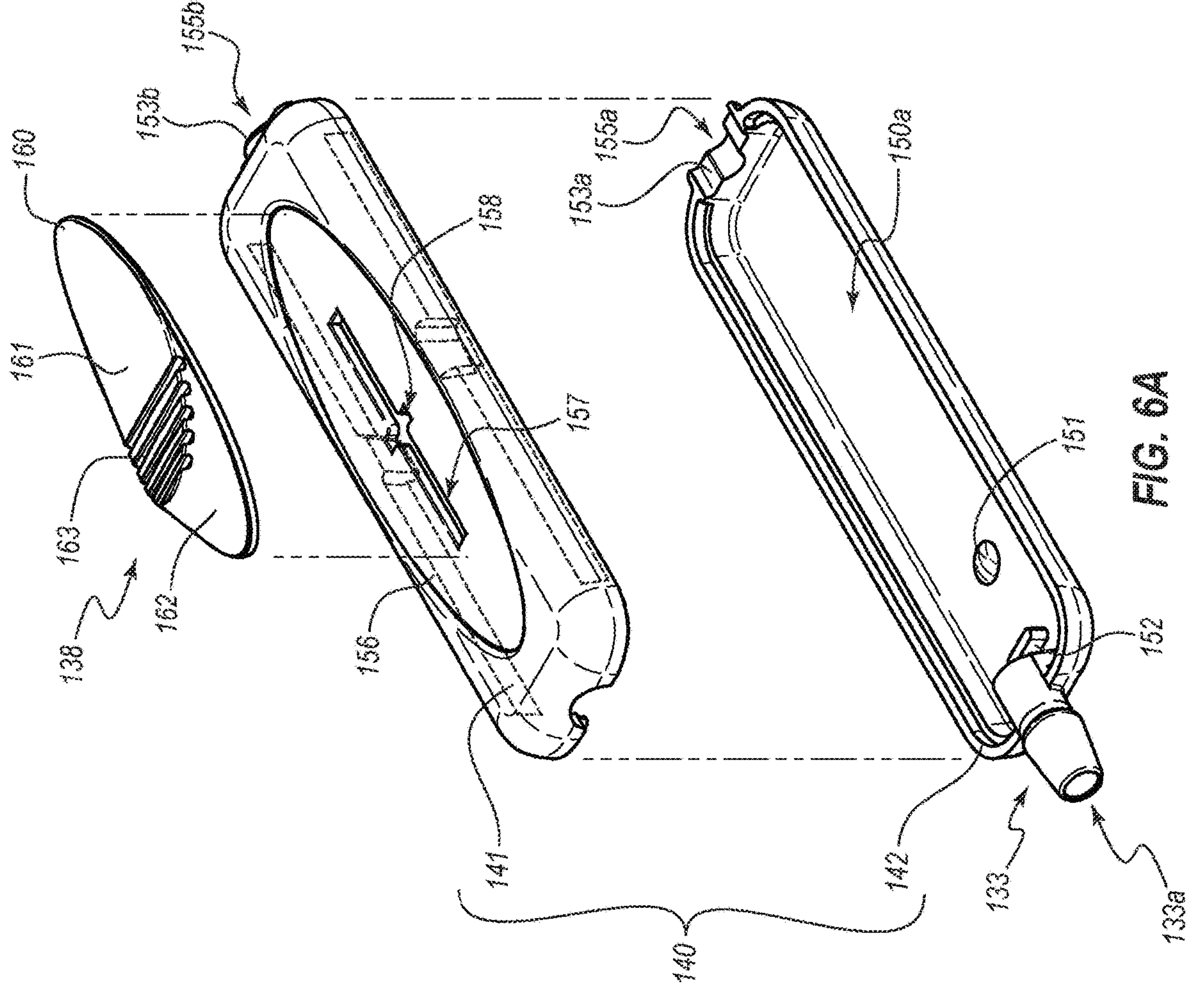
FIG. 6A is an exploded perspective view of a housing and an actuation interface portion of an actuation mechanism of the tissue engagement device, which may also be referred to as an interlock mechanism.

FIG. 6A depicts an exploded perspective view of an embodiment of the housing 140, which includes the upper shell 141 and the lower shell 142. The lower shell 142 can include the connector 133 at a distal end thereof, as previously described. The connector 133 can define a lumen 133*a* through which the actuation member 145 and the access device 147 can pass for advancement to a deployed state or retraction to a retracted state.

Figures 6B, 6C:
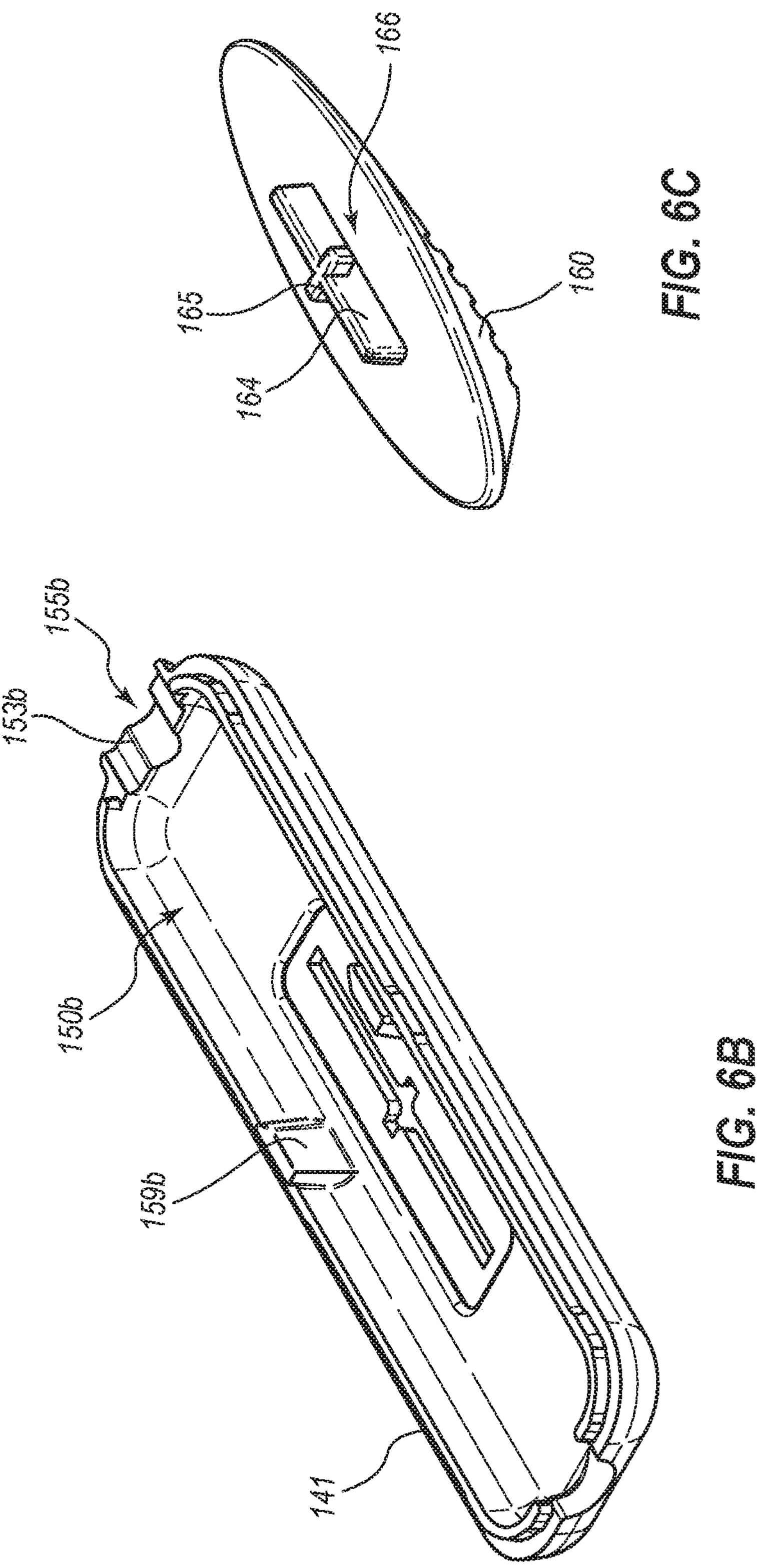
FIG. 6B is a further perspective view of an upper component of the housing.
FIG. 6C is a further perspective view of the actuation interface.

With reference to FIGS. 6A and 6B, the lower shell 142 can define a cavity 150*a* into which certain components of the actuation mechanism 147, or portions thereof, can be received. The upper shell 141 likewise defines a cavity 150*b* into which certain components or portions thereof can be received. When the upper and lower shells 141, 142 are coupled to each other, the cavities 150*a*, 150*b* define a unitary volume of space.

The dual interlock property of the illustrated embodiment of the actuation mechanism 137 generally operates on two levels or planes. The upper level is generally defined by a lower portion of the upper shell 141. The lower level is defined by the lower shell 142. For example, the lower shell 142 includes an actuator stop 151, which is a rounded protrusion that extends upwardly from a substantially flat base wall of the lower shell 142. As further discussed below, the actuator stop 151 is configured to interact with a component in the lower level.

The lower shell 142 further includes a coupling protrusion 152 that is configured to connect with the gate 144, as further discussed below. A proximal end of the lower shell 142 can include a key slot region 155*a* defined by a keying surface 153*a*. A proximal end of the upper shell 141 likewise can include a key slot region 155*b* defined by a keying surface 155*b*. When the upper and lower shells 141, 142 are coupled to each other, the key slot regions 155*a*, 155*b* define a unitary key slot, and the keying surfaces 153*a*, 153*b* cooperate to maintain a fixed rotational orientation of the hub 149 as portions thereof are advanced distally into or retracted proximally from the housing 140.

The upper shell 141 defines a recess 156 within which the actuation interface 138 can translate forward or backward. The upper shell 141 further defines a longitudinal channel 157 along which the actuation interface 138 can be translated forward or backward. The upper shell 141 also includes a transverse channel 158 through which a portion of the actuation interface 138 can be advanced.

With reference to FIG. 6B, the upper shell 141 defines a pair of stops 159*a*, 159*b* that can selectively prevent proximal movement of the shuttle 146, as further described below. The stops 159*a*, 159*b* reside within the upper level along which the dual interlock mechanism operates.

With reference to FIG. 6A, the illustrated actuation interface 138 is formed as a button 160, which may also be referred to as a slider. The illustrated button 160 is particularly well suited for actuation via a thumb of a user while the housing 140 is held by fingers of the hand, although other actuation grips are possible. The button 160 includes a proximal surface 161 that is contoured to receive a thumb tip of a user. The proximal surface 161 rises in a distal direction toward a grip 163, which can provide traction for the user. While any suitable grip arrangement is contemplated, the illustrated grip includes transversely directed grooves. A distal surface 162 drops steeply from the apex. The user can readily grip the apex and/or upper portions of the distal surface 162 to apply rearward directed force for retraction of the actuation assembly 148.

With reference to FIG. 6C, the button 160 can include a longitudinal guide 164 that is sized to slide within the longitudinal channel 157 of the upper shell 141. The button 160 can further include a lateral retainer or transverse bar 165 that cooperates with a bottom surface of the button 160 to define a channel 166 on either side of the guide 164. The channels 166 can receive a portion of the upper shell 141 that borders the longitudinal channel 157.

Figure 6E:
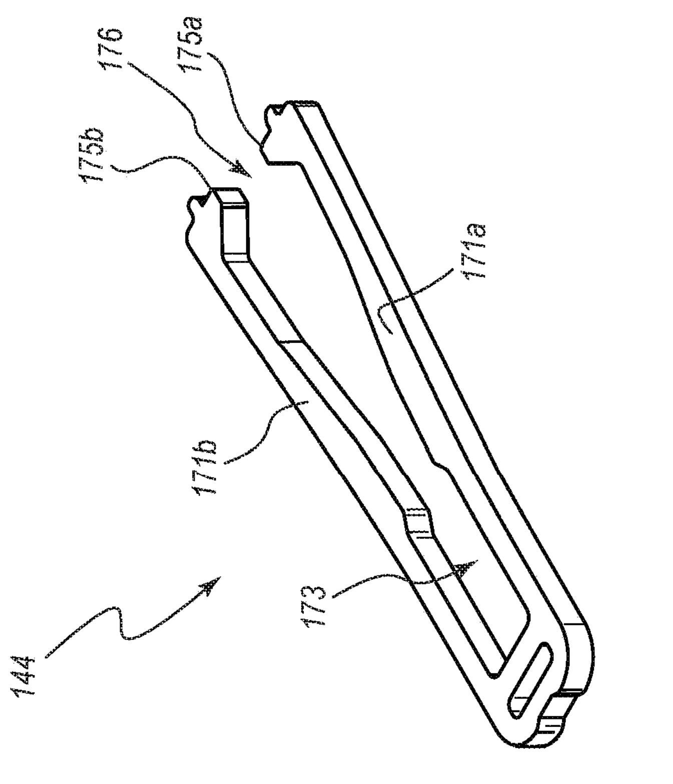
FIG. 6E is another perspective view of the gate that depicts the gate in an open state.
Figure 6D:
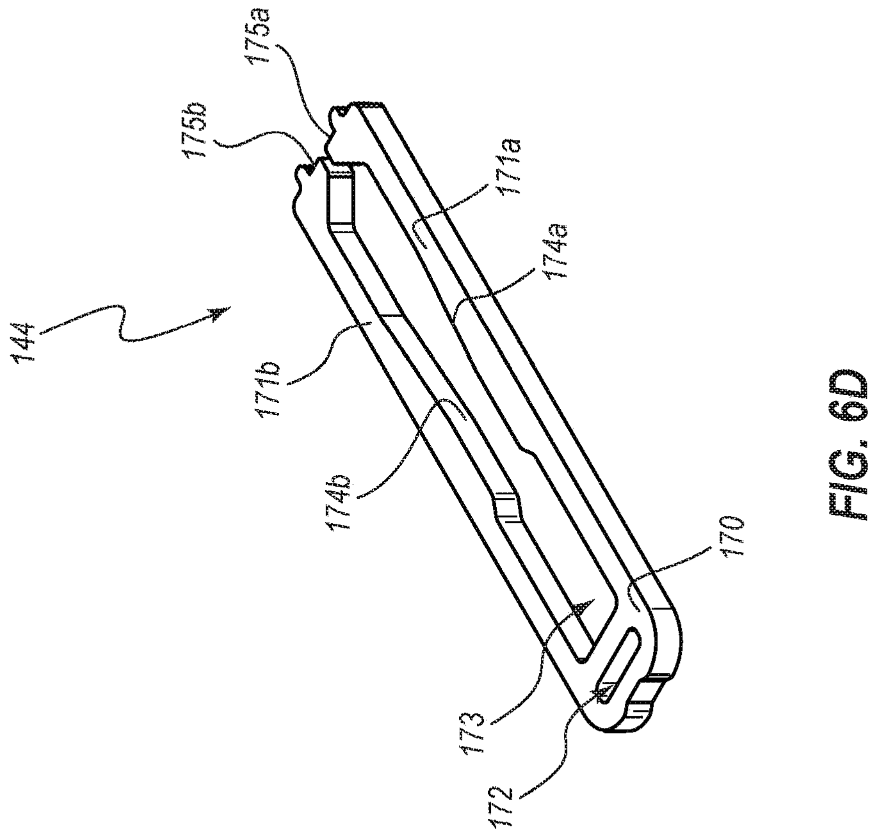
FIG. 6D is a perspective view of an embodiment of a gate portion of the actuation mechanism that depicts the gate in a closed state.

FIGS. 6D and 6E depict the gate 144 in two different operational states. In FIG. 6D, the gate 144 is closed, whereas the gate 144 is open in FIG. 6E. The gate 144 is positioned within the lower shell 142. Accordingly, the gate 144 operates in the lower level of the dual interlock mechanism.

The gate 144 includes a base 170 from which two resilient arms 171*a*, 171*b* extend in the proximal direction. The base 170 defines an opening 172 sized to receive the coupling protrusion 152 of the lower shell 142 to connect the gate 144 to the lower shell 142. The distal ends of the arms 171*a*, 171*b* cooperate with an inner surface of the base 170 to define a receptacle 173. When the gate 144 is coupled to the lower shell 142, the actuator stop 151 resides within the receptacle 173.

Generally central portions of the arms 171*a*, 171*b* include inwardly projecting camming surfaces 174*a*, 174*b*, respectively. The camming surfaces 174*a*, 174*b* are configured to interact with a portion of the shuttle 146 to selectively open the gate 144, as further described below.

The proximal ends of the arms 171*a*, 171*b* include stops 175*a*, 175*b* that are configured to abut a portion of the hub 149 to prevent distal movement of the hub 149 when the gate 144 is in the closed state of FIG. 6D. When the gate 144 is in the open state of FIG. 6E, the stops 175*a*, 175*b* are separated from each other to define a passageway 176 through which the portion of the hub 149 can pass in the distal direction.

Figure 6F:
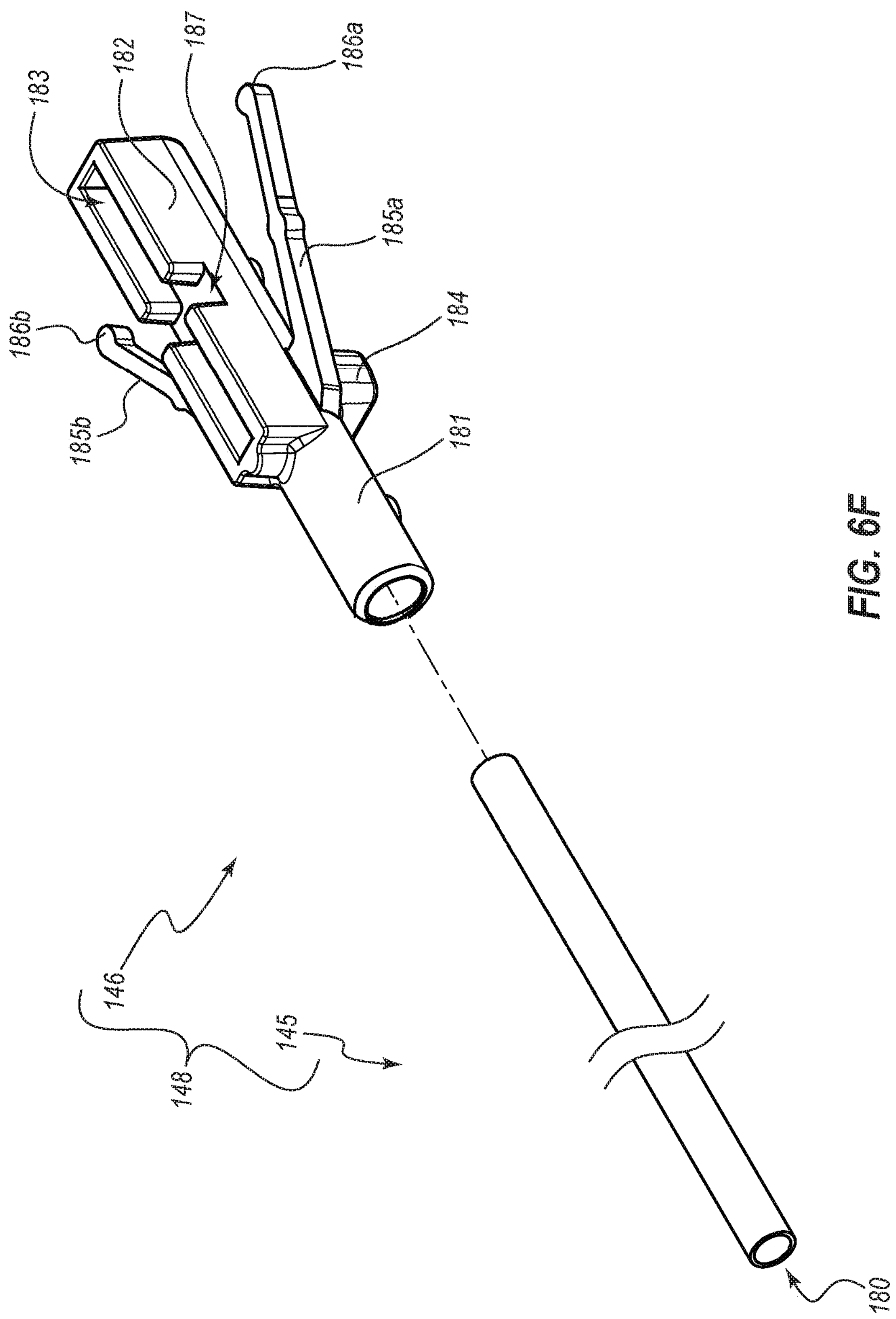
FIG. 6F is an exploded perspective view of a portion of an embodiment of an actuator that includes an embodiment of an actuation cannula and an embodiment of an actuation shuttle in an uncoupled state.

FIG. 6F depicts a portion of the actuator 148, which includes the actuation member 145 and the shuttle 146. As previously mentioned, the actuator 148 further includes the actuation interface 138.

As previously mentioned, in the illustrated embodiment, the actuation member 145 is a cannula that defines a lumen 180. The lumen 180 is sized to permit passage of the access device 147. A proximal end of the actuation member 145 can be coupled to a body 181 of the shuttle 146 in any suitable manner.

The shuttle 146 includes a pair of upwardly projecting sidewalls 182 that cooperate to define a longitudinal channel 183 and a lateral channel 187. The channels 183, 187 are sized to receive the longitudinal guide 164 and the transverse bar 165 that project downwardly from the button 160.

With reference to FIGS. 6A-6C and 6F, in coupling the button 160 with the shuttle 146 and the upper shell 141 of the housing 140, the longitudinal guide 164 and the transverse bar 165 are inserted through the longitudinal channel 157 and the transverse channel 158 of the upper shell 141 and into the longitudinal channel 183 and the lateral channel 187 of the shuttle 146. The button 160 and the shuttle 146 can be connected together in any suitable manner, including one or more of friction fit, snap fit, adhesive, etc. Once the button 160 and the shuttle 146 are connected, the button 160 is free to slide forward and rearward within the longitudinal channel 157 of the upper shell.

With reference again to FIG. 6F, the shuttle 146 further includes a downward protrusion, such as a wedge 184. The wedge 184 is configured to operate on the lower plane of the interlock mechanism. In particular, the wedge 184 can be positioned between the proximal portions of the arms 171*a*, 171*b* of the gate 144. The wedge 184 can include camming surfaces that interact with the camming surfaces 174*a*, 174*b* of the gate 144 to urge apart the resiliently flexible arms 171*a*, 171*b*. The wedge 184 can interact with the actuator stop 151 (FIG. 6A) to prevent the shuttle from traveling too far in a distal direction. In particular, the stop 151 may be positioned so as to ensure that a distal end of the actuation member 145 stops at a desired position relative to the actuated arms 108*a*, 108*b* (see FIG. 5C), such as, for example, a position that is slightly proximal of the tissue engaging members 109*a*, 109*b* of the actuated arms 108*a*, 108*b*. Such as position may, for example, avoid pushing an engaged portion of the target tissue layer off of the actuated engaging members 109*a*, 109*b*.

With continued reference to FIG. 6F, the illustrated embodiment of the shuttle 146 includes a pair of laterally and proximally projecting resiliently flexible arms 185*a*, 185*b*. The arms 185*a*, 185*b* include stops 186*a*, 186*b* at the proximal ends thereof. The arms 185*a*, 185*b* and stops 186*a*, 186*b* are positioned to operate on the upper level of the interlock mechanism. In particular, the arms 185*a*, 185*b* may be flexed inwardly as the actuator 148 is advanced distally to deploy the arms 108*a*, 108*b* via the actuation member 145 via contact with a portion of the hub 149, as discussed further below. Upon distal advancement of the hub 149 to deploy the access device 147, however, the arms 108*a*, 108*b* can automatically return to a natural extended state, at which point the stops 186*a*, 186*b* engage the stops 159*a*, 159*b* of the upper shell 141. The shuttle 146 can be retained in this position until the hub 149 is returned to a proximal position to free the stops 186*a*, 186*b* from the stops 159*a*, 159*b*, as discussed further below with respect to FIG. 7E.

Figure 6G:
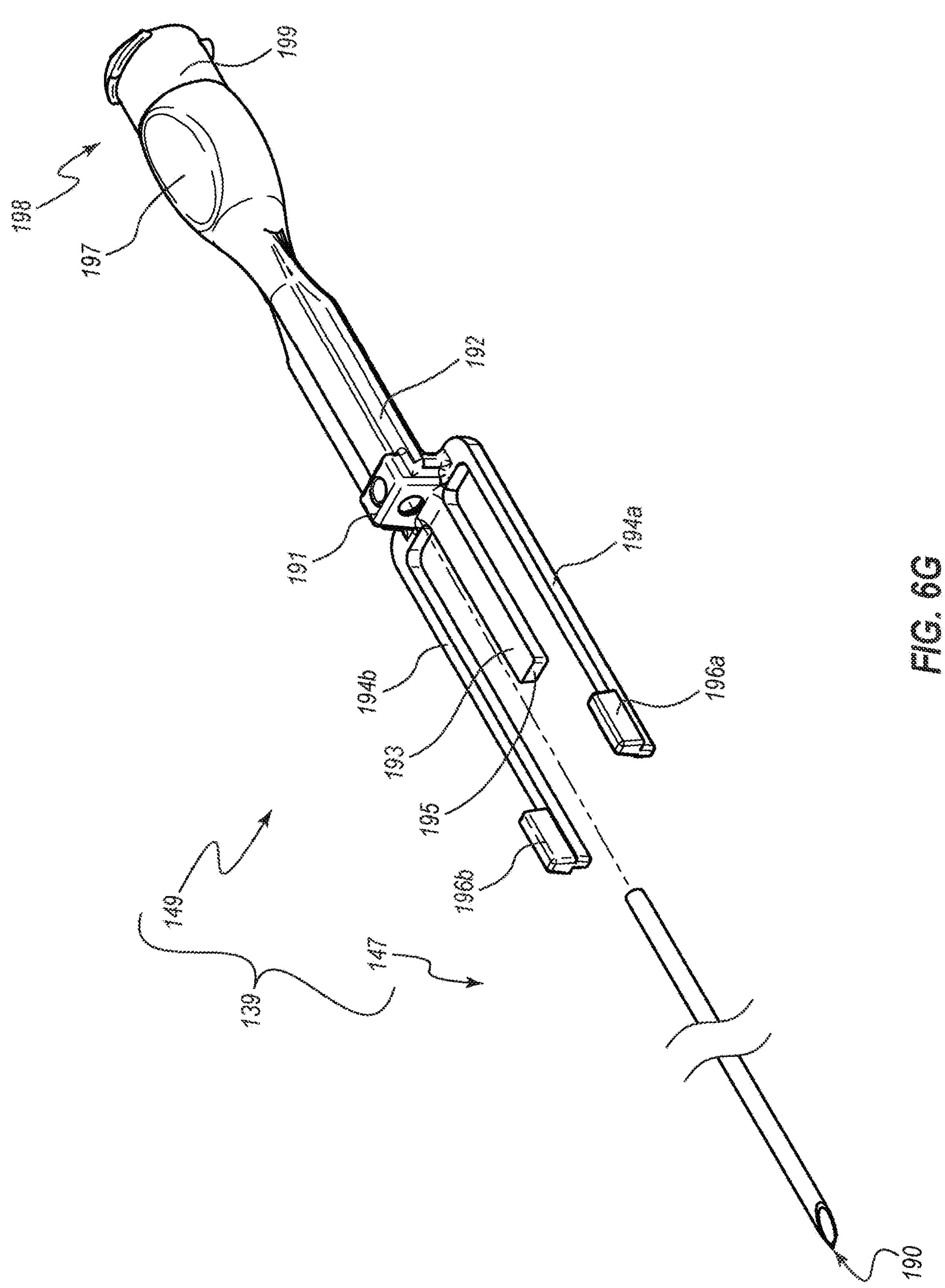
FIG. 6G is an exploded perspective view of an embodiment of an access assembly that includes an embodiment of an access device and an embodiment of a hub in an uncoupled state.

FIG. 6G depicts the access assembly 139, which includes the access device 147 or piercing member and the hub 149. A proximal end of the access device 147 can be coupled to a body 191 of the hub 149 in any suitable manner. The access device 190 can define a lumen 190 through which communication with a region beneath the target tissue layer (e.g., the pericardial space) can be established once the access device 147 pierces through the target tissue layer. For example, a guide wire may be delivered through the lumen 190.

The hub 192 includes a neck 192 that is shaped to fit within the key slot defined by the keying surfaces 153*a*, 153*b* of the lower and upper shells 142, 141. The neck 192 can include outwardly projecting flanges that, in cooperation with the keying surfaces 153*a*, 153*b*, prevent rotational movement of the hub 149 about a longitudinal axis thereof.

The hub 192 can include a grip 197, which may be positioned proximal of the neck 192. The grip 197 can be sized and configured to be readily manipulated by a user, such as by using a second hand while the user holds the housing 140 with a first hand. In the illustrated embodiment, a medical connector 198 is positioned at a proximal end of the hub 192. Any suitable connection interface is contemplated for the medical connector 198, which can serve to couple the hub 149 with any suitable medical device(s) or equipment for delivering and/or withdrawing fluid to/from a region accessed by the distal end of the access device 147. In the illustrated embodiment, the connector 198 comprises a Luer fitting 199.

With continued reference to FIG. 6G, the hub 149 includes three distally projecting tines, prongs, or arms 193, 194*a*, 194*b*. In the illustrated embodiment, the arms 193, 194*a*, 194*b* substantially form a trident shape. The central arm 193 is shorter than the outer arms 194*a*, 194*b* and includes a stop 195 at a distal end thereof. The stop 195 operates at the lower level of the interlock system, and is configured to interact with the stops 175*a*, 175*b* of the gate 144.

An upward protrusion 196*a*, 196*b* is positioned at the distal end of each of the side arms 194*a*, 194*b*. The protrusions 196*a*, 196*b* are positioned to operate at the upper level of the interlock system. In particular, the protrusions 196*a*, 196*b* are configured to bend the proximal ends of the arms 185*a*, 186*a* inward when the hub 149 is drawn proximally to a retracted state, thereby permitting proximal movement of the shuttle to a retracted state, as shown in and discussed further with respect to FIG. 7E.

Some of the features of the illustrated actuation mechanism 137 include a pair of elements to accomplish a given function. For example, the two arms 185*a*, 186*a* interact with the two stops 159*a*, 159*b* to prevent retraction of the actuation member 145 under certain conditions. In other embodiments, only a single set of interacting features may be used. In some instances, however, a redundant set of interacting features can provide strength, stability, and/or balance to the system and/or act a as a backup or failsafe.

FIGS. 7A-7E demonstrate various stage of operation of the actuation mechanism 137. Many details regarding these stages of operation have already been provided. FIGS. 7A-7E and the discussion that follows are to provide further clarity regarding to the manners in which the various components interact (e.g., to achieve a dual interlock mechanism). Certain features that were discussed with respect to at least FIGS. 5A-6G may not be repeated in the following discussion, as the purpose of the present discussion is to provide a streamlined understanding of the illustrated actuation mechanism 137. The further details disclosed with respect to at least FIGS. 5A-6G are fully applicable here, but will be omitted for the sake of brevity and clarity.

Figure 7A:
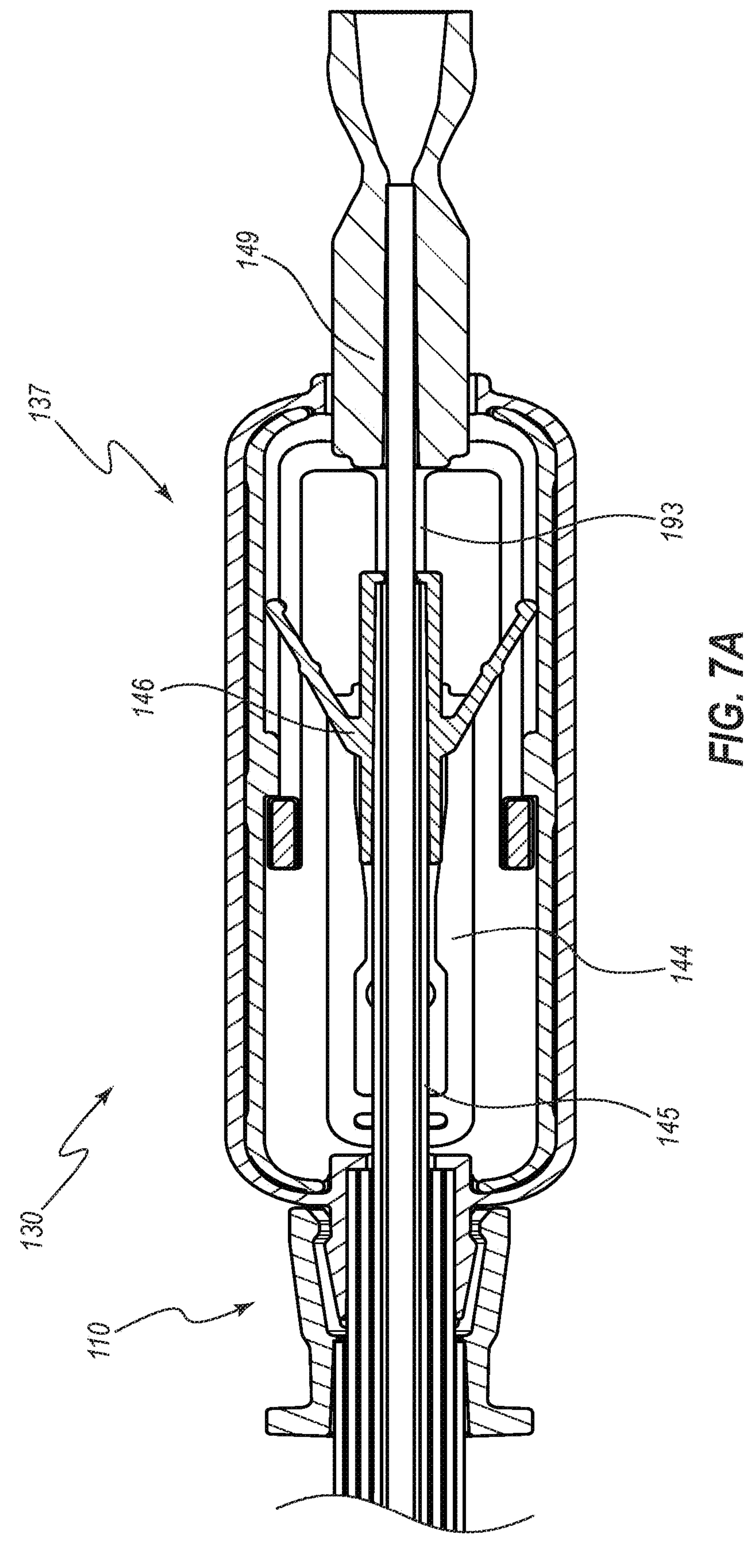
FIG. 7A is a cross-sectional view of the tissue engagement device along the view line 7A-7A in FIG. 1, as coupled with the tunneler cannula (also shown in cross-section), that depicts the actuation device in a fully retracted configuration and corresponds with the distal view depicted in FIG. 5B.

FIG. 7A is a cross-sectional view of the tissue engagement device 130 along the view line 7A-7A in FIG. 1, as coupled with the tunneler cannula 110, which is also shown in cross-section. This drawing depicts the shuttle 146 in a fully retracted configuration. Correspondingly, the drawing depicts the actuation member 145 in the retracted configuration. Likewise, the access device 147 and the hub 149 are in the retracted configuration. Accordingly, the tissue engagement device 130 is in the fully retracted configuration. FIG. 7A corresponds with the view of the distal end of the tissue engagement device 130 depicted in FIG. 5B. In this operational state, the gate 144 is closed and interacts with the central prong 193 of the hub 149 to prevent deployment of the access device 147.

Figure 7B:
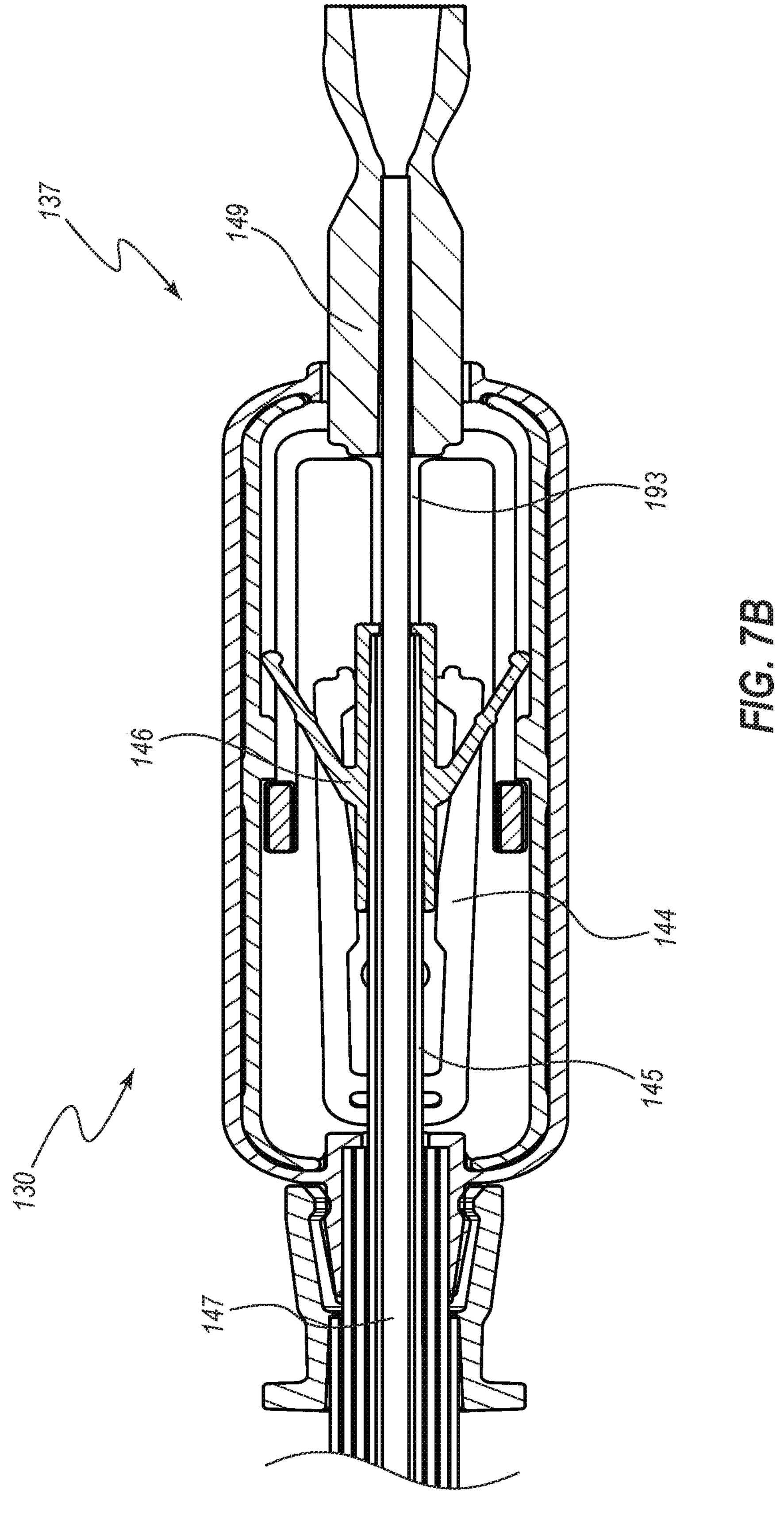
FIG. 7B is another cross-sectional view of the tissue engagement device such as that of FIG. 7A, that depicts the actuation device in a partially deployed state, with the actuator advanced distally to an intermediate position.

In FIG. 7B, the tissue engagement device 130 is in a partially deployed state. In particular, the shuttle 146 has been advanced distally, but not yet to its distal-most orientation. That is, the shuttle 146 has been advanced to an intermediate phase of deployment. The gate 144 has begun to open, but is not yet open sufficiently wide to permit the distal passage of the central prong 193 of the hub 149.

Figure 7C:
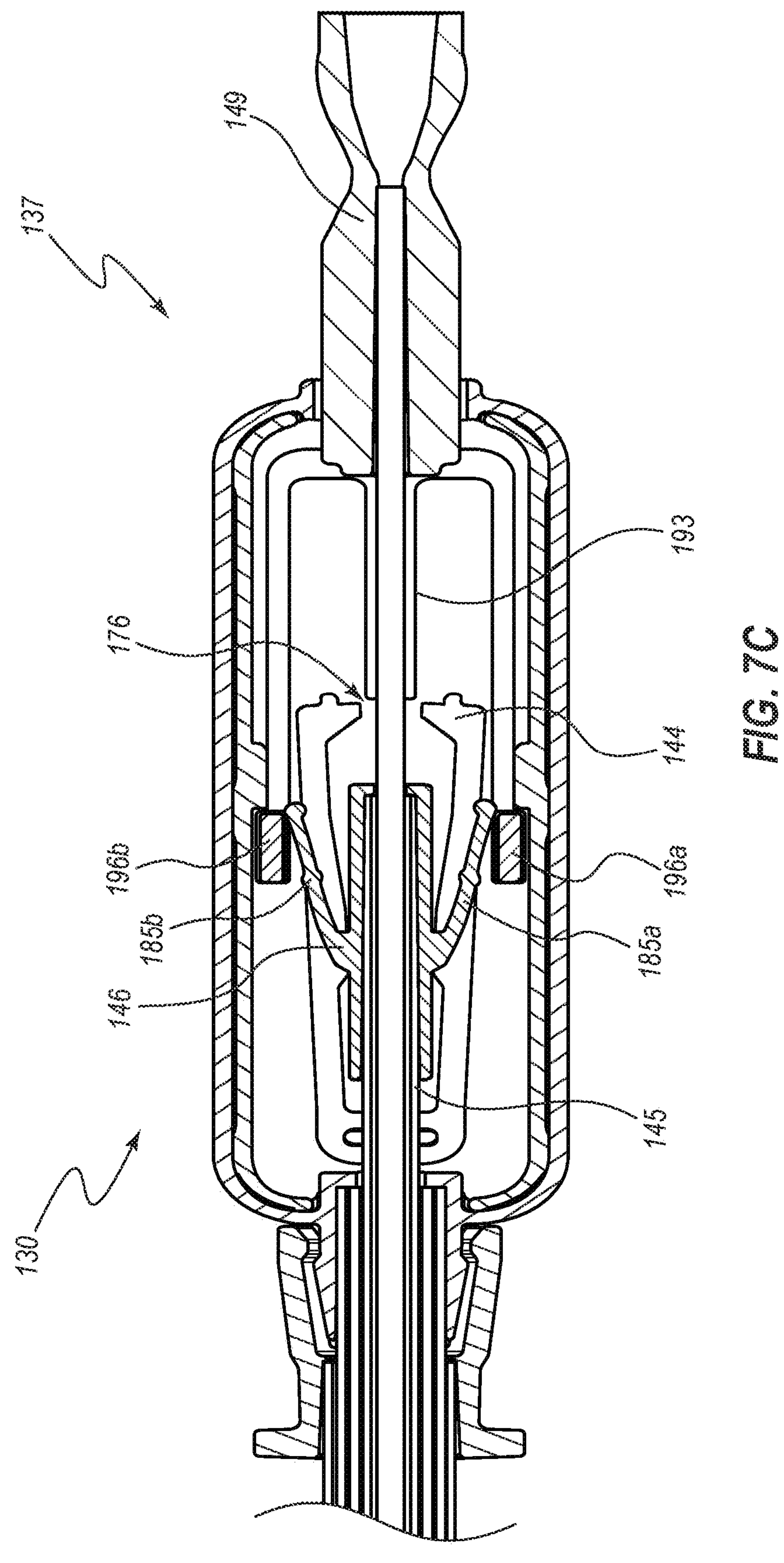
FIG. 7C is another cross-sectional view of the tissue engagement device, such as that of FIGS. 7A and 7B, that depicts the actuation device in a partially deployed state, with the actuator advanced a distal-most position.

FIG. 7C depicts the actuation mechanism 137 of the tissue engagement device 130 in another partially deployed state. In this state, the shuttle 146 has been advanced to its distal-most position, and is thus fully deployed. However, the hub 149 and the access device 147 remain in their retracted state. The full distal movement of the shuttle 146 has opened the gate 144 to create the passageway 176, which is now sufficiently large to permit passage of the central prong 193 of the hub 149 in a distal direction. FIG. 7C corresponds with the view of the distal end of the tissue engagement device 130 depicted in FIG. 5C.

Figure 7D:
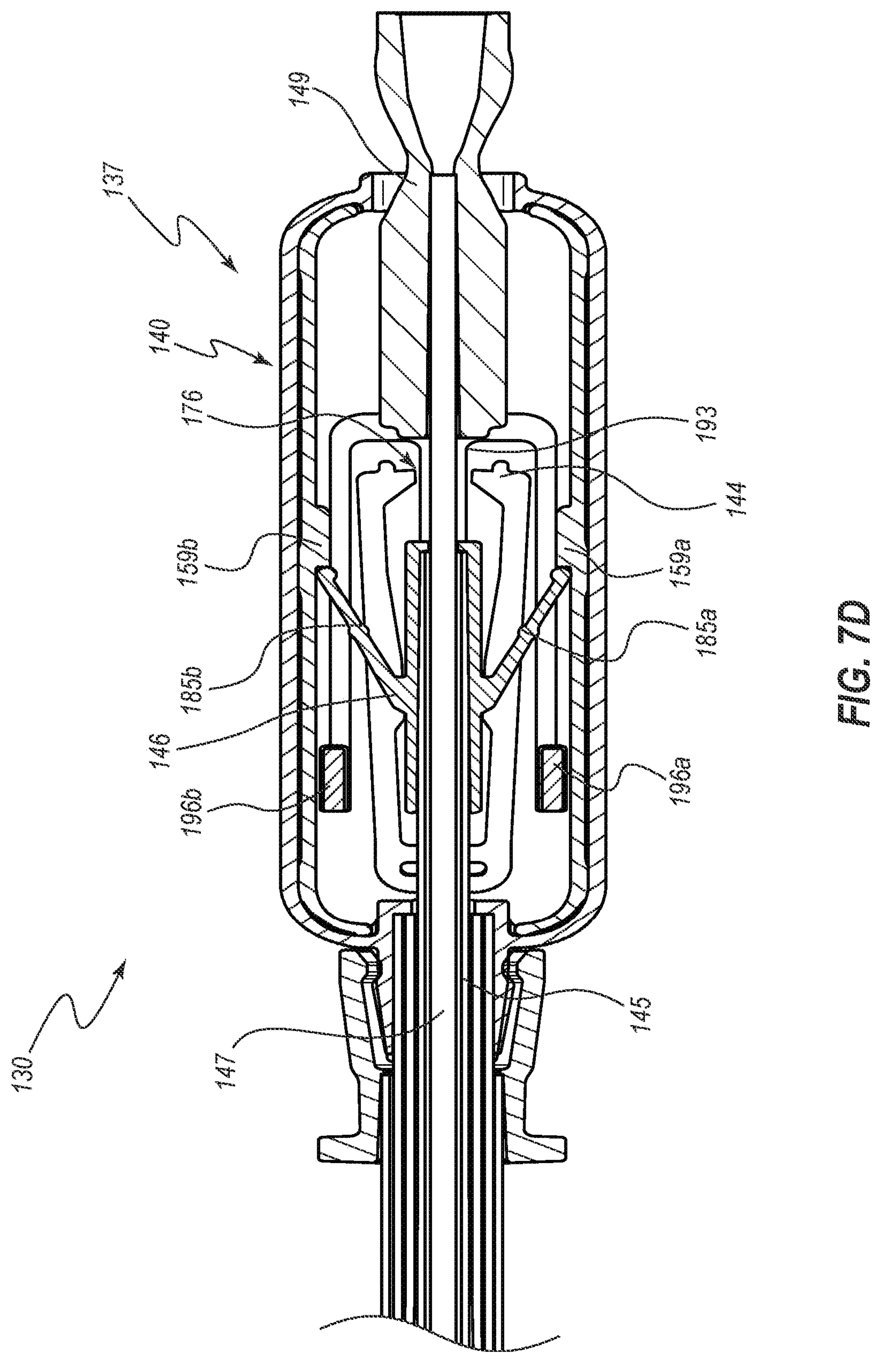
FIG. 7D is another cross-sectional view of the tissue engagement device, such as that of FIGS. 7A-7C, that depicts the actuation device in a fully deployed state, with the actuator in the distal-most orientation and the access assembly advanced distally to deploy the access device.

FIG. 7D depicts the actuation mechanism 137 of the tissue engagement device 130 in a fully deployed state. Specifically, the shuttle 146 and the actuation member 145 are in their distal-most orientations, and the hub 149 has been moved distally to at least partially deploy the access device 147.

In this operational mode, the hub 149 is able to move distally and proximally in an unconstrained manner, or at least unconstrained within a range permitted by the confines of the housing 140. Unconstrained distal movement permits a user to select the amount of force to be applied to the access device 147 to pierce the target tissue layer, as well as the distance (within a limited range) to which the access device 147 will be inserted through the tissue layer.

Unconstrained proximal movement can be an advantageous safety feature, in some instances. For example, if a user inserts the access device 147 through the tissue layer, but then becomes distracted or otherwise inadvertently releases the hub 149, the underlying layer can be protected from damage, such as by pushing the access device 147 in the proximal direction. In the context of pericardial access, for example, a distal tip of the access device 147 may be readily pushed rearward by the beating heart if the practitioner maintains a grip on the housing 140, but releases a grip on the hub 149.

Movement of the hub 149 and its upward protrusions 196*a*, 196*b* in the distal direction releases the arms 185*a*, 185*b* of the shuttle 146 to automatically resiliently expand outwardly into contact with the sides of the housing 140. The proximal ends of the arms 185*a*, 185*b* come into contact with the distal faces of the stops 159*a*, 159*b*, which prevents the shuttle 146 from moving distally in the present configuration.

Figure 7E:
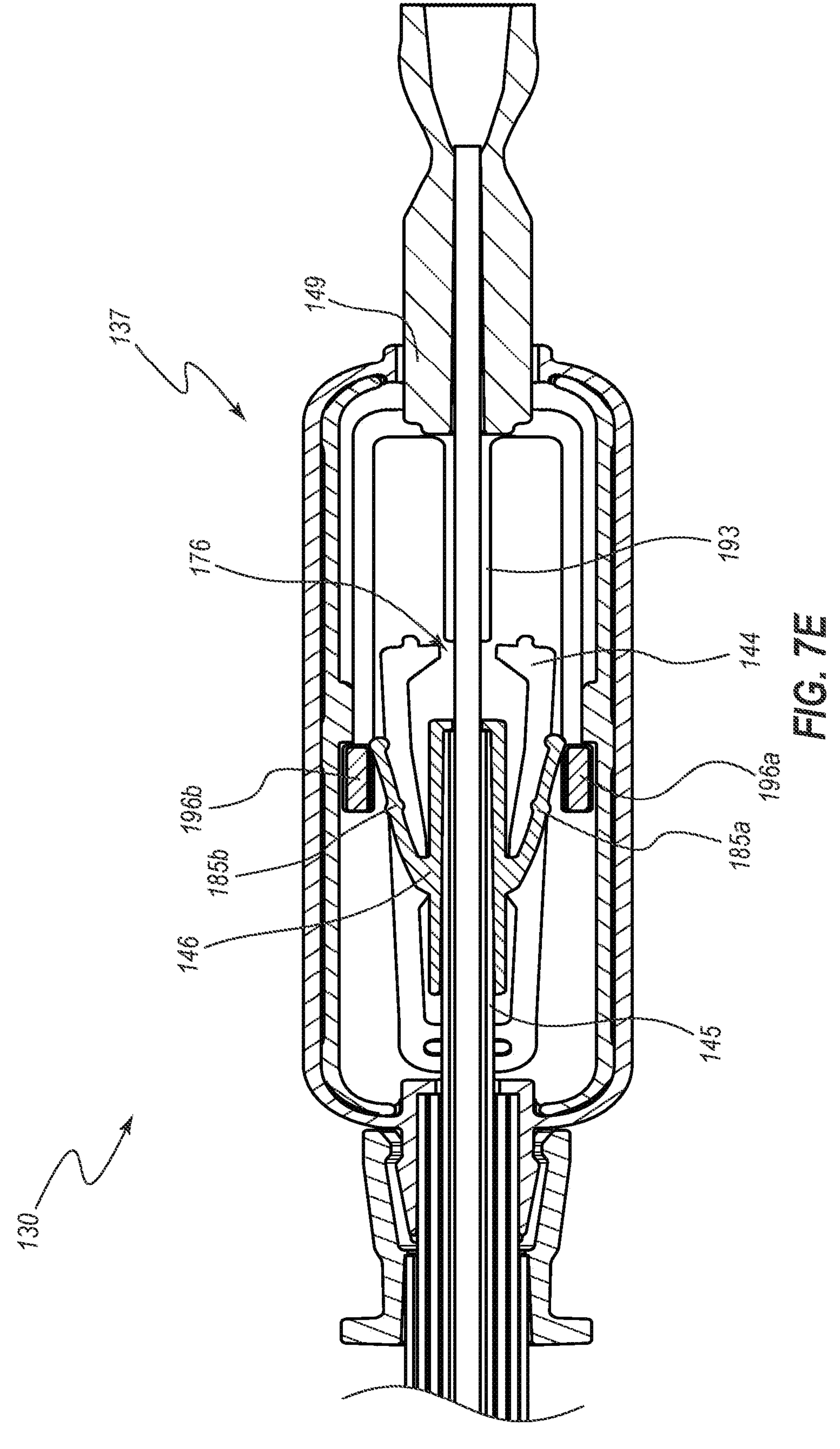
FIG. 7E is another cross-sectional view of the tissue engagement device, such as that of FIGS. 7A-7D, that depicts the actuation device in a partially deployed state again, with the access assembly having been withdrawn distally to a configuration that permits retraction of the actuator.

FIG. 7E depicts the actuation mechanism 137 in a partially deployed state again, with the hub 149 having been withdrawn distally to a configuration that permits retraction of the actuation member 145. Moreover, movement of the hub 149 and its upward protrusions 196*a*, 196*b* in the proximal direction compresses the arms 185*a*, 185*b* of the shuttle 146 to be displaced inward and out of contact from the distal faces of the stops 159*a*, 159*b*. This configuration permits proximal movement of the shuttle 146 to draw the actuation member 145 into the retracted position.

FIGS. 8A-8K depict various stages of illustrative methods for engaging a target tissue layer and accessing a space beneath the same. Many details regarding these method stages have already been provided. FIGS. 8A-8K and the discussion that follows are to provide further clarity regarding to the methods. Certain features that were discussed with respect to at least FIGS. 5A-7E may not be repeated in the following discussion, as the purpose of the present discussion is to provide a streamlined understanding of the illustrated method stages. The further details disclosed with respect to at least FIGS. 5A-7E are fully applicable here, but will be omitted for the sake of brevity and clarity.

One illustrative method includes each stage depicted in FIGS. 8A-8K in the sequential order shown. In the illustrative method, the pericardial space of the heart of a patient is accessed. Other methods are contemplated, including some that do not employ each method stage illustrated and/or that use additional stages. Moreover, other suitable contexts (e.g., target tissue layers other than the pericardium) are contemplated.

Figure 8A:
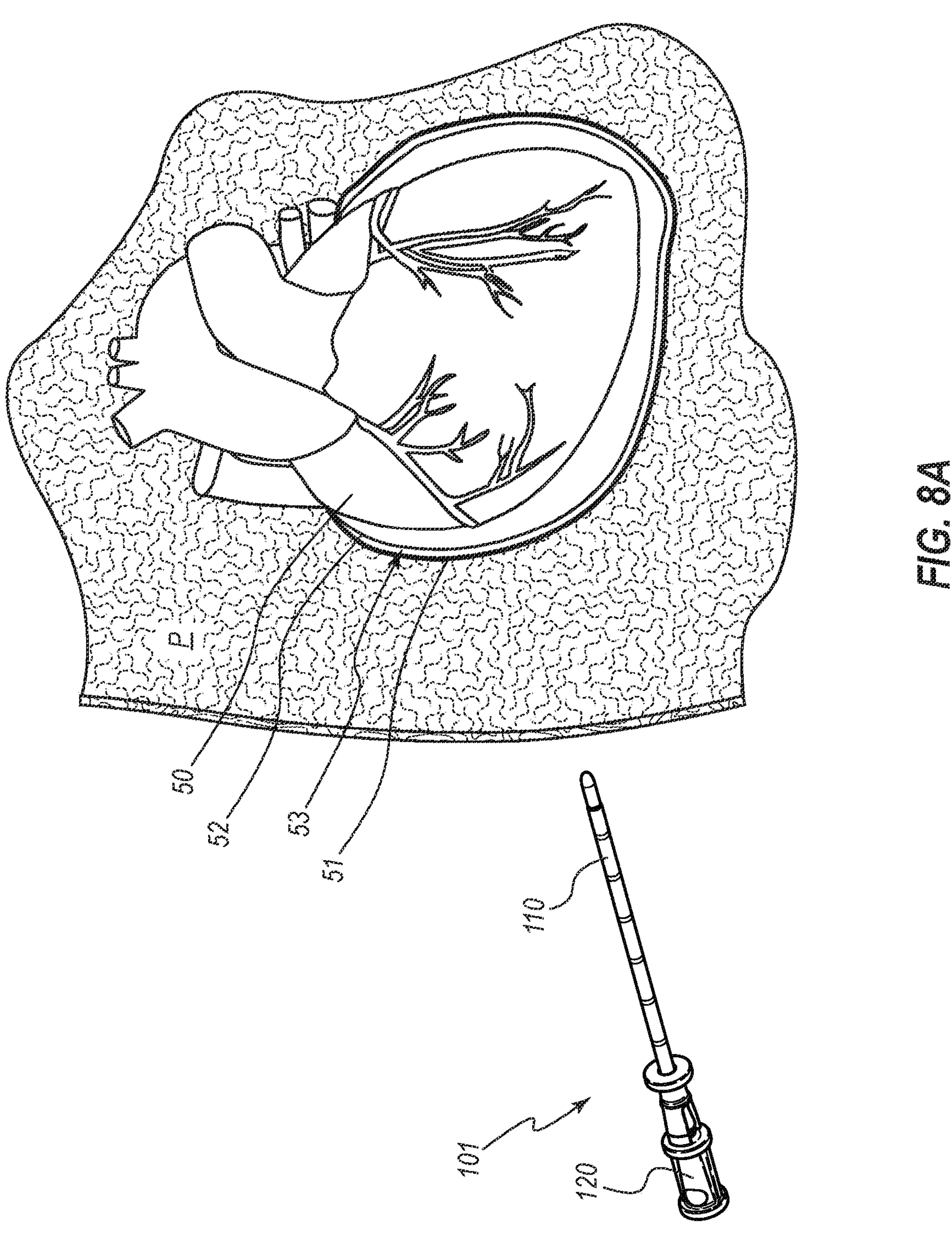
FIG. 8A depicts an early stage of an illustrative method for accessing a region beneath a tissue layer, in which the tissue engagement system of FIG. 1 can be used.

FIG. 8A depicts an early stage of an illustrative method for accessing a region beneath a tissue layer. In particular, the method is used to access the pericardial space 53 between the pericardium 51 and the epicardium 52 of the heart 50 of a patient P.

In the illustrated method, the tunneling assembly 101 is provided, such as by being removed from sterile packaging. In some embodiments, the obturator 120 and the tunneling cannula 110 are provided in a preassembled state. In other instances, an earlier stage of the method includes coupling the obturator 120 to the tunneling cannula 110 into the configuration show.

In some embodiments, an anterior approach may be used in directing the tunneling assembly 101 toward the heart 50. In other embodiments, an inferior or posterior approach is used, which can require passing the tunneling assembly 101 through the diaphragm. Such an approach may also be referred to as a transdiaphragmatic or subdiaphragmatic approach. Each such approach may be referred to as a subxiphoid approach. The different approaches may result in different angles relative to the heart. In still further instances, an intercostal approach, e.g., between the 6th and 7th ribs may be used and may provide direct access to different areas of the heart. In some instances, the intercostal space allows the apex of the heart to be accessed, and so such an approach is also called a transapical approach.

In view of the foregoing, a number of different approaches to the heart are contemplated. The tissue engagement systems 100, 102 and tissue engagement devices 130 disclosed herein can be particularly well suited for any such approach to the heart. In particular, the systems 100, 102 and devices 130 can be particularly well suited to engage, grasp, pull, and or otherwise manipulate the pericardium 51 at any number of different approach angles. For example, the tissue engagement devices 130 can work effectively at shallow angles of approach or steep angles of approach. Indeed, certain embodiments are capable of functioning well at approach angles of from 0 degrees (e.g., a fully transverse orientation) through 90 degrees (e.g., a fully orthogonal orientation). With respect to a 0-degree approach, a distal end of the device 130 can come into contact with the pericardium and create a ripple, or a substantially vertical (or upwardly extending) wall of tissue ahead of the distal end of the device. This phenomenon is similar to pushing a piece of fabric along a tabletop using a finger to generate a ripple or wave response. A local wave or ripple can create an at least somewhat transverse surface, relative to a distal end of the device 130, to which the tines can engage (e.g., grasp, grab, embed within, snag, catch, etc.)

Figure 8B:
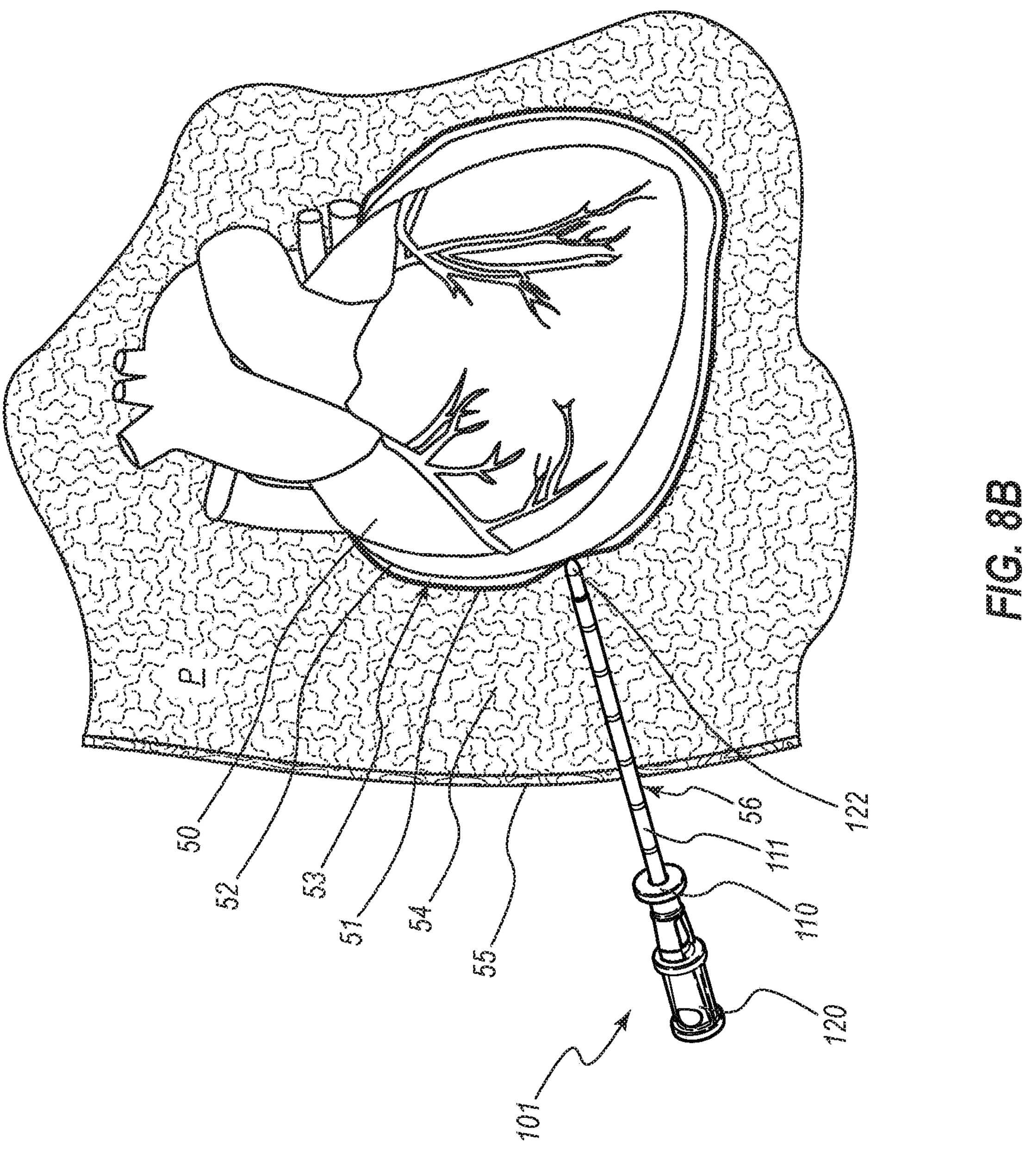
FIG. 8B depicts another stage of the illustrative method in which the obturator contacts the tissue layer.

FIG. 8B depicts a stage at which the tunneling assembly 101 has been advanced through an incision 56 in the skin 55 of the patient. The blunt tip 122 of the obturator 120 has been urged through the connective tissue 54 of the patient P into contact with an external surface of the pericardium 51.

Figure 8C:
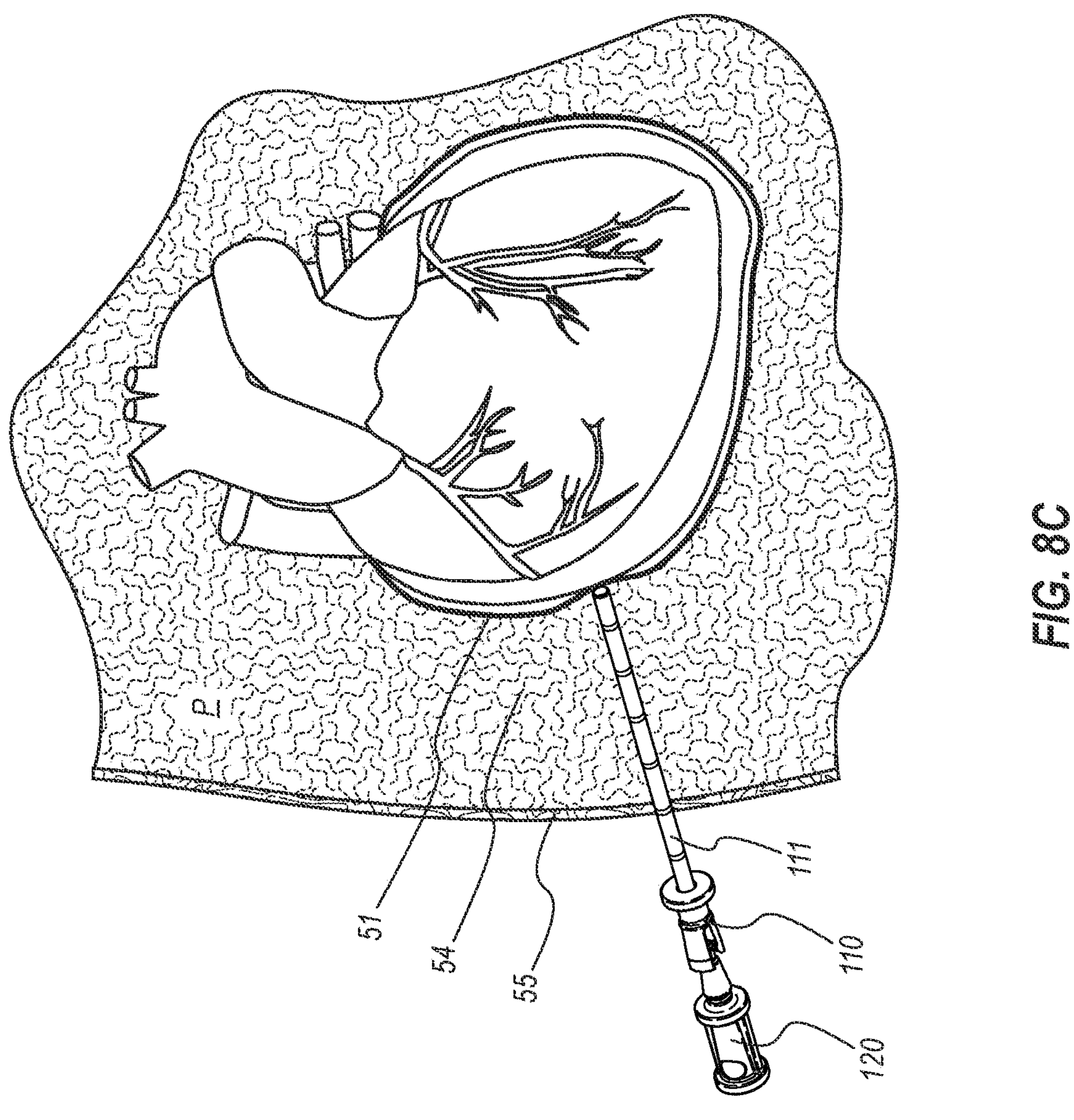
FIG. 8C depicts another stage in which the obturator is being removed from the tunneler cannula.

FIG. 8C depicts a stage at which the obturator 120 is decoupled from the tunneling cannula 110 and removed therefrom. The tube 111 portion of the tunneling cannula 110 is left in the tissue 54 to provide a channel to the pericardium 51.

Figure 8D:
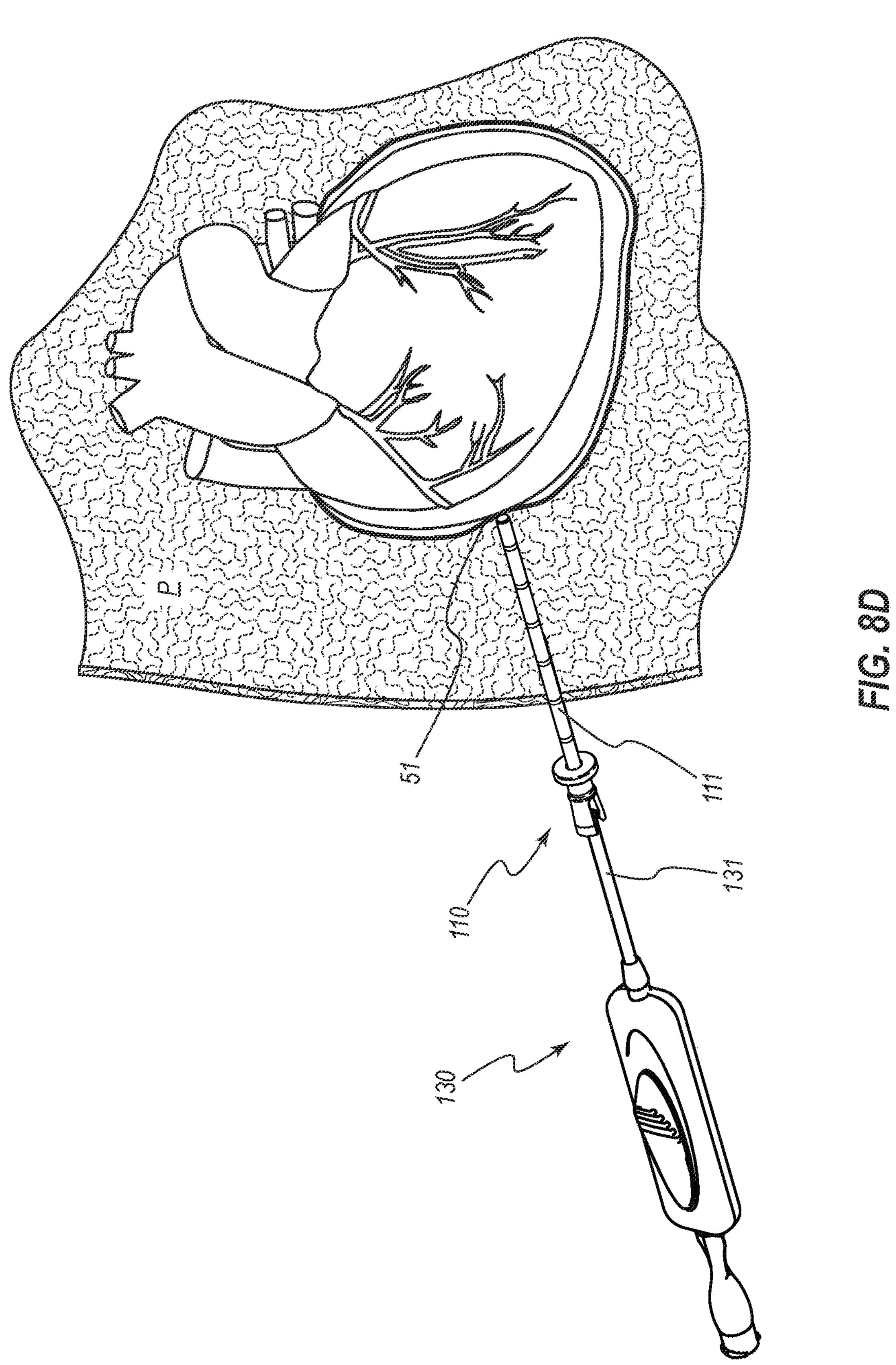
FIG. 8D depicts another stage in which the tissue engagement device is advanced through the tunneler cannula.

FIG. 8D depicts a stage in which the tissue engagement device 130 is coupled with the tunneler cannula 110. In particular, the sheath 131 is advanced through the tube 111 and toward the pericardium 51.

Figure 8E:
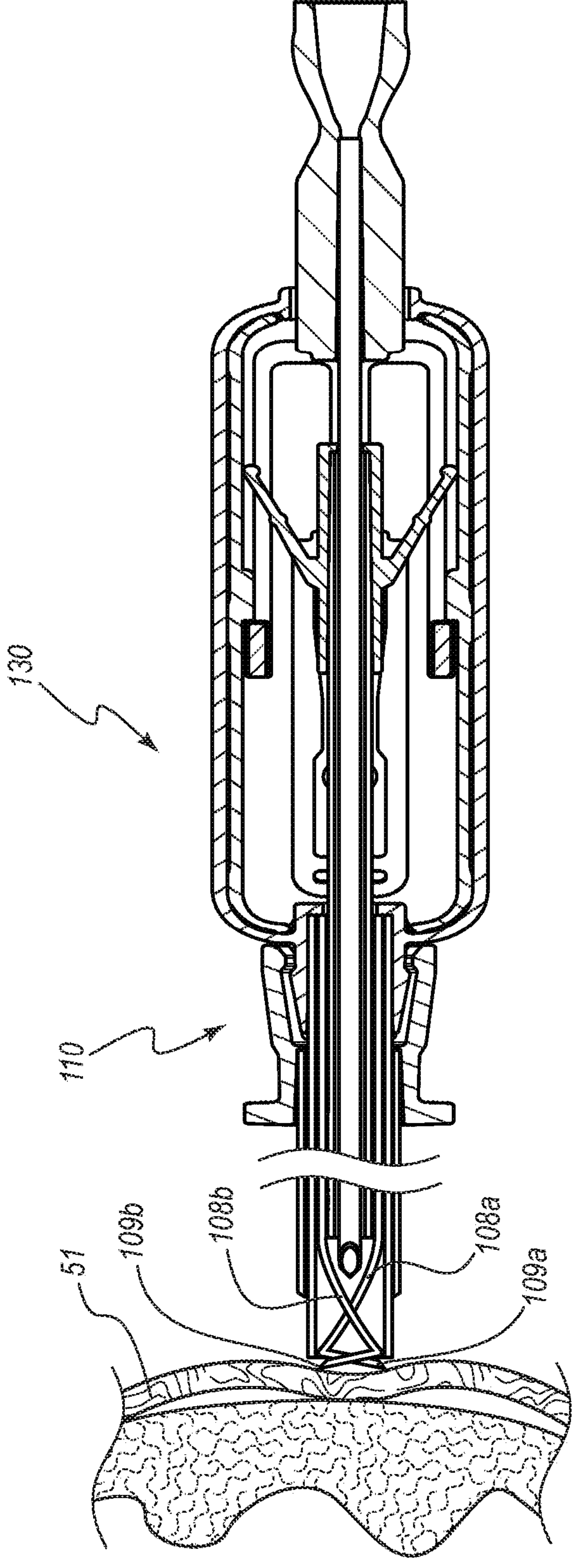
FIG. 8E depicts another stage in which the tissue engagement device is in the fully retracted configuration, such as that of FIGS. 5B and 7A, with distal tips of engagement arms positioned at the tissue layer.

FIG. 8E depicts another stage in which the tissue engagement device 130 is in the fully retracted configuration, such as that of FIGS. 5B and 7A, with the tissue engagement members 109*a*, 109*b* (e.g., the distal tips) of engagement arms 108*a*, 108*b* positioned at the target tissue layer, which in this instance is the pericardium 51. The tissue engagement device 130 is fully coupled with the tunneler cannula 110.

Figure 8F:
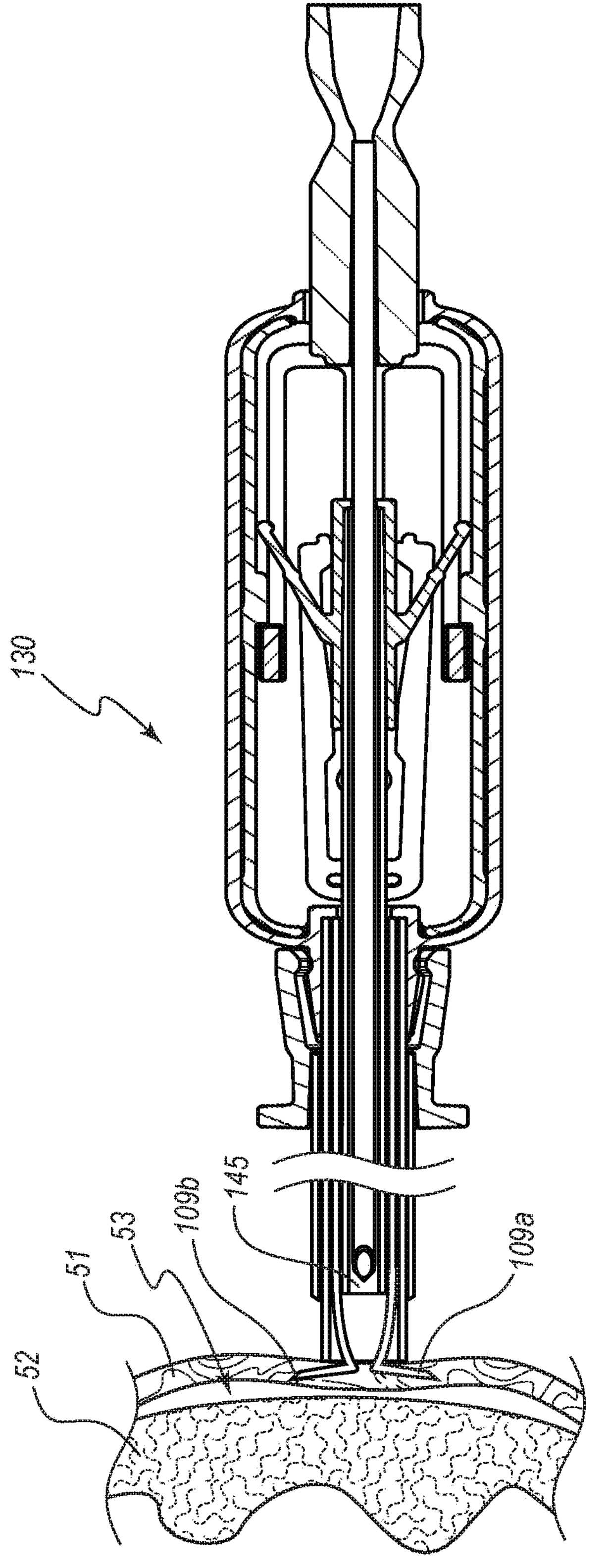
FIG. 8F depicts another stage in which the tissue engagement device is in the partially deployed state, such as that of FIG. 7B, with the actuator advanced distally to an intermediate position to embed the engagement arms in the tissue layer.

FIG. 8F depicts another stage in which the tissue engagement device 130 is in the partially deployed state, such as that of FIG. 7B, with the actuation member 145 advanced distally to an intermediate position to embed the tissue engagement members 109*a*, 109*b* arms in the pericardium 51. In the illustrated embodiment, the tissue engagement members 109*a*, 109*b* do not extend through a full thickness of the pericardium 51 to pass into the pericardial space 53. Stated otherwise, the engagement members 109*a*, 109*b* do not pass through an interior or bottom surface of the pericardium 51. This can result from the initial shallow angle of the engagement members 109*a*, 109*b* relative to the pericardium 51, and further, from a shallow deployment path for each of the engagement members 109*a*, 109*b*. By "shallow deployment path," it is meant that the path traced by the engagement members 109*a*, 109*b* (e.g., a distal tip thereof) extends only a small longitudinal distance from the distal end of the actuation member 145, or from the starting point of the respective engagement member 109*a*, 109*b*. In various embodiments, each engagement member 109*a*, 109*b* progresses distally from its staring point to a maximum longitudinal distance (i.e., a distance as measured only in the longitudinal direction, or in a direction that is collinear with or parallel to a longitudinal axis of the actuation member 145) that is no greater than 1, 2, 3, or 4 millimeters. Indeed, in some embodiments, an entirety of the path traced by each engagement member 109*a*, 109*b* may have no longitudinal component (e.g., may be entirely lateral), or may have a longitudinal component that progresses only in the proximal direction, or stated otherwise, only moves laterally and proximally from the starting point.

In various embodiments, each engagement member 109*a*, 109*b* defines a maximum length. For example, in the illustrated embodiment, the maximum length of each engagement member 109*a*, 109*b* is the distance from the distal point thereof to a primary bend (e.g., the only bend in each arm 108*a*, 108*b* that is readily apparent in FIG. 8F). In various embodiments, each engagement member 109*a*, 109*b* progresses distally from its starting point to a maximum longitudinal distance that is no greater than 0.25, 0.5, 0.75, 1, 1.25, or 1.5 times the maximum length of the engagement member 109*a*, 109*b*.

It may alternatively be stated that each engagement member 109*a*, 109*b* follows a deployment path that is substantially transverse to the surface of the target tissue layer. The substantially transverse deployment of the engagement members 109*a*, 109*b* can embed the engagement members 109*a*, 109*b* within the tissue layer and can put the tissue layer under tension in the transverse direction. A substantially transverse deployment path also reduces the risk of contacting and/or damaging an underlying tissue layer, such as the epicardium 52.

In other embodiments, at least a portion of one or more of the engagement members 109*a*, 109*b* may extend through a full thickness of the target tissue layer. Stated otherwise, in other embodiments, the engagement members 109*a*, 109*b* may pierce through the bottom or inner surface of the tissue layer.

In some embodiments, the each of the engagement members 109*a*, 109*b* defines an angle relative to a distal projection of longitudinal axis of the device 130. In various embodiments, this angle can be no less than 60, 70, or 80 degrees throughout movement of the actuation cannula 145 from the retracted position to the extended position.

Figure 8G:
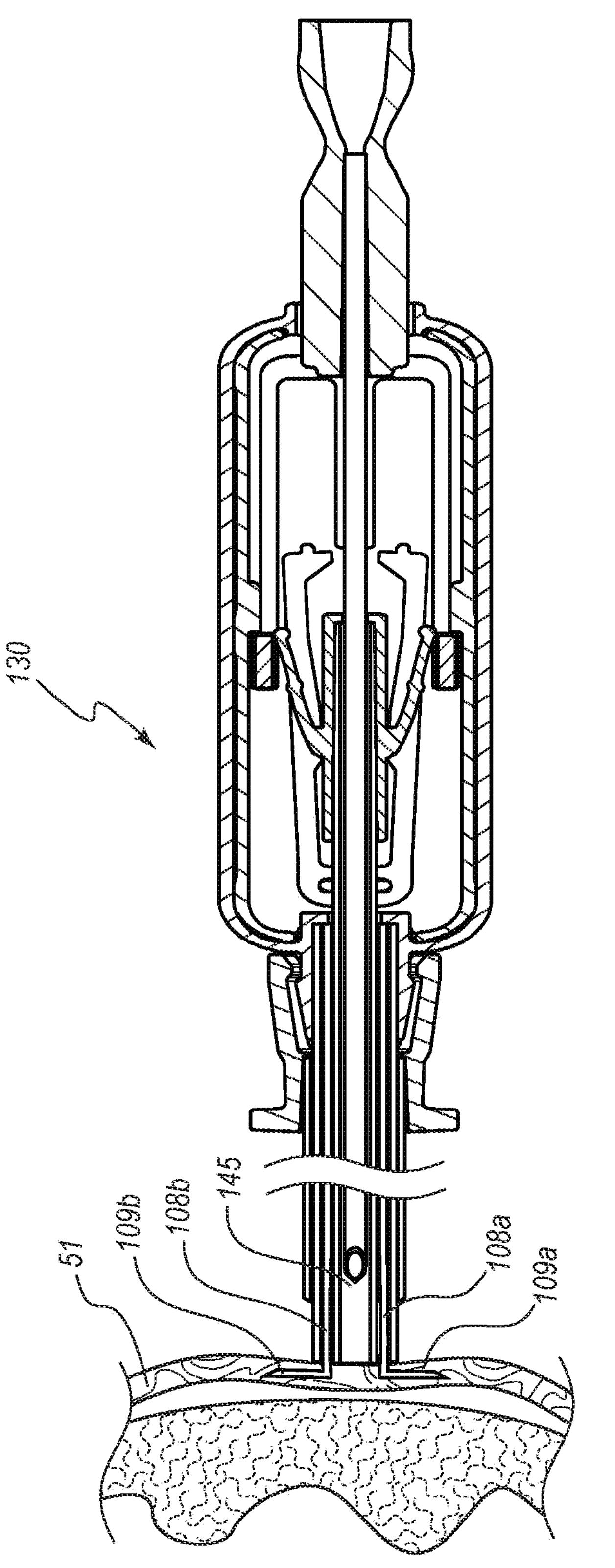
FIG. 8G depicts another stage in which the tissue engagement device is in the further partially deployed state, such as that of FIGS. 5C and 7C, with the actuator advanced to the distal-most position to further embed the engagement arms in the tissue layer.

FIG. 8G depicts a stage in which the tissue engagement device 130 is in the further partially deployed state, such as that of FIGS. 5C and 7C, with the actuation member 145 advanced to the distal-most position to further embed the engagement members 109*a*, 109*b* in the pericardium 51. In the illustrated embodiment, the engagement members 109*a*, 109*b* extend laterally outward at an angle of approximately 90 degrees relative to the adjacent, proximal portions of the arms 108*a*, 108*b*. Other angles relative to the arms 108*a*, 108*b* in this fully deployed state are also contemplated, as further discussed below.

Figure 8H:
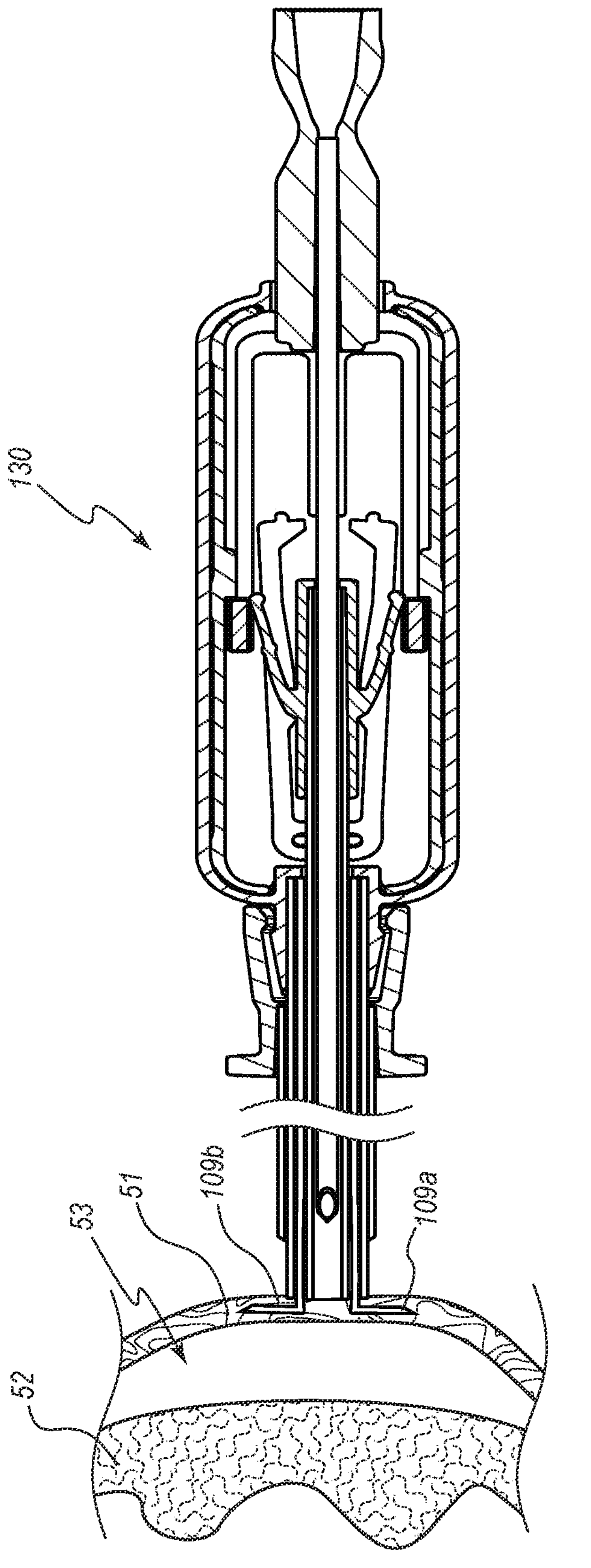
FIG. 8H depicts another stage in which the tissue engagement device is in the same configuration as that depicted in FIG. 8G and in which the system is drawn proximally to enlarge a space between the tissue layer and an underlying structure.

FIG. 8H depicts a stage in which the tissue engagement device 130 is in the same configuration as that depicted in FIG. 8G and in which the tissue engagement device 130 is drawn proximally to enlarge the pericardial space 53 between the pericardium 51 and the epicardium 52 in the vicinity of the engagement members 109*a*, 109*b*. Such a separation event may result in tenting of the pericardium 51 at the engagement position. This tenting is shown only schematically in FIG. 8H, as the tenting can be quite steep in some instances, such as may result from vacuum or other forces within the pericardial space 53 as the pericardium 51 is drawn upward in the manner shown.

Figure 8I:
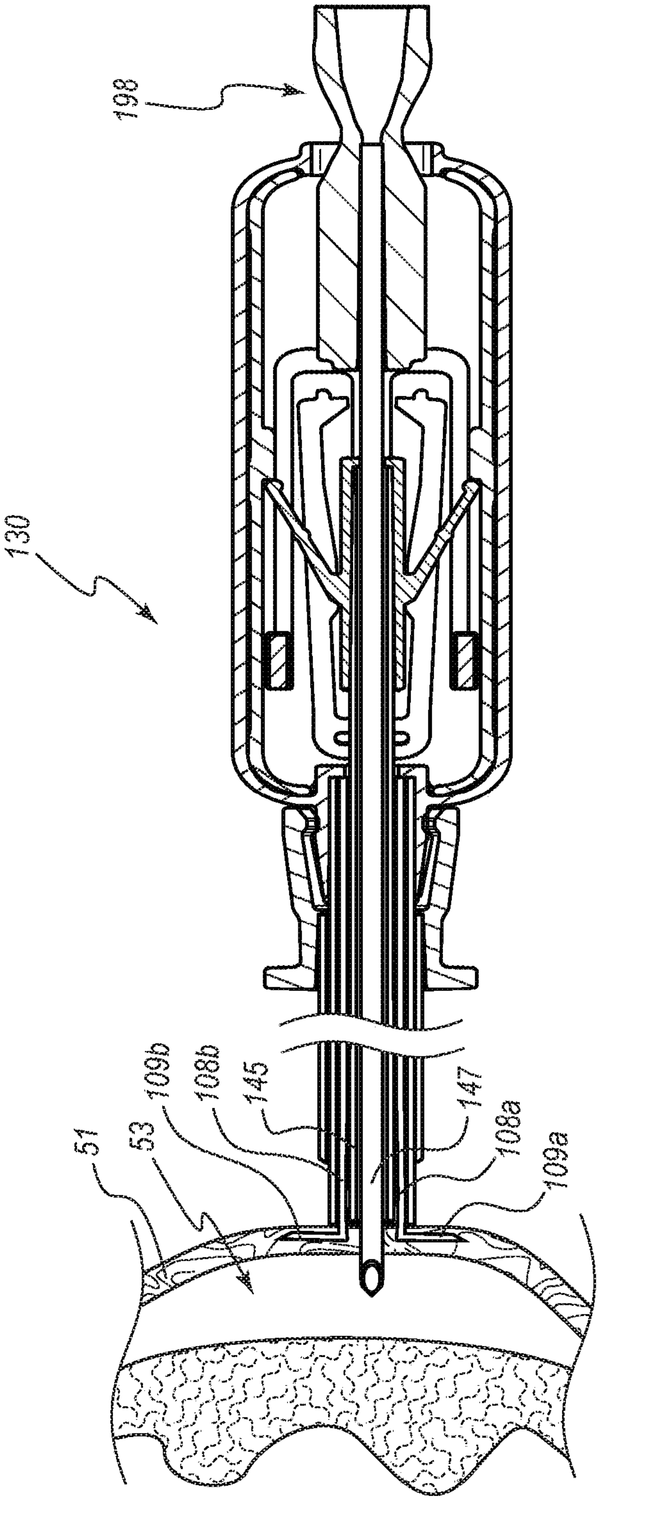
FIG. 8I depicts another stage in which the tissue engagement device has been moved to the fully deployed state, such as that of FIGS. 5D and 7D, in that both the actuator and the access device have been advanced distally; the access device has pierced the tissue layer to provide access to the space between the tissue layer and the underlying structure.

FIG. 8I depicts a stage in which the tissue engagement device 130 has been moved to the fully deployed state, such as that of FIGS. 5D and 7D, in that both the actuation member 145 and the access device 147 have been advanced distally. At the illustrated stage, the access device 147 has pierced the pericardium 51 to provide access to the pericardial space 53. Communication with pericardial space 53, such as for the introduction or removal of fluid, can be achieved via the medical connector 198.

As discussed with respect to FIG. 8H, tenting in the vicinity of the actuation arms 108*a*, 108*b* may be quite steep. However, the region between the arms 108*a*, 108*b* may be substantially planar due to tension provided by the arms 108*a*, 108*b*. The access device 147 thus may be readily advanced through the portion of the pericardium 51 that is held in tension, which is relatively unaffected by the neighboring tenting.

In particular, a distal end of the access device 147 may be pointed, or angled relative to a longitudinal axis of the device. As a result, insertion of the device 147 is much easier through a planar region that is substantially orthogonal to the longitudinal axis of the device—e.g., through the region between the arms 108*a*, 108*b*—than it is through regions that have shallower angles relative to the tip, such as the steep tented surfaces that surround the region that is held between the arms 108*a*, 108*b*. For this reason, it can be advantageous in some embodiments to ensure that a tip of the access device 147 passes through a line that extends between the arms 108*a*, 108*b* when the arms 108*a*, 108*b* are in the deployed state.

Figure 8J:
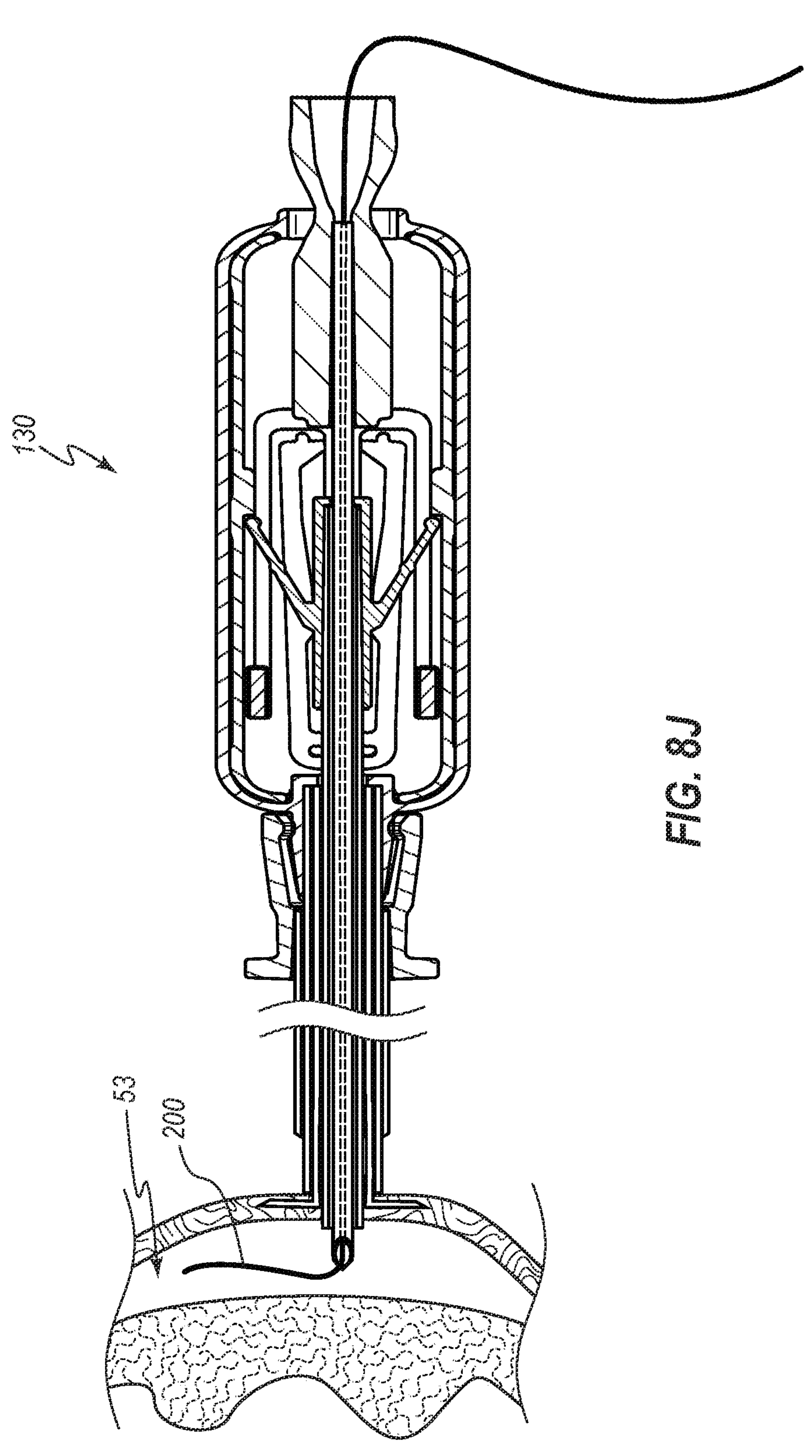
FIG. 8J depicts another stage in which the tissue engagement device remains in the fully deployed state and a distal end of a guidewire has been advanced through the access device into the space between the tissue layer and the underlying structure.

FIG. 8J depicts a stage in which the tissue engagement device 130 remains in the fully deployed state and a distal end of a guidewire 200 has been advanced distally through the access device 147 into the pericardial space 53. The guidewire 200 may be of any suitable variety or size. In various embodiments, a thickness of the guidewire can be 0.035 inches (0.89 millimeters) or 0.032 inches (0.81 millimeters). In some embodiments, the guidewire 200 may comprise a flexible tip. The flexible tip may be interchangeably referred to as a bias tip. The flexible tip may be a distal portion of the guidewire that has a low structural rigidity and is easily deflectable. In one such embodiment, the guidewire 200 may be a floppy tip guidewire. In another embodiment, the guidewire 200 may be J-tip guidewire. A person of ordinary skill in the art will recognize that floppy tip and J-tip guidewires are known guidewires traditionally used urological procedures and the placement of drainage catheters or temporary pacemakers.

It is contemplated that the flexible tip may reduce puncturing of undesired regions of tissue. For example, traditional guidewires may puncture the myocardium upon entry into the pericardial space 53. The use of a flexible tip guidewires, such as the floppy and J-tip guidewires, is contemplated to prevent puncturing the myocardium upon entry into the pericardial space 53. For example, the floppy tip guidewire may be deflected upon contact with the myocardium. The J-tip guidewire may deflect following after a portion of the guidewire is advanced distally through the access device 147 into the pericardial space 53. In such an instance, the J-tip guidewire may be deflected prior to contacting the myocardium.

Figure 8K:
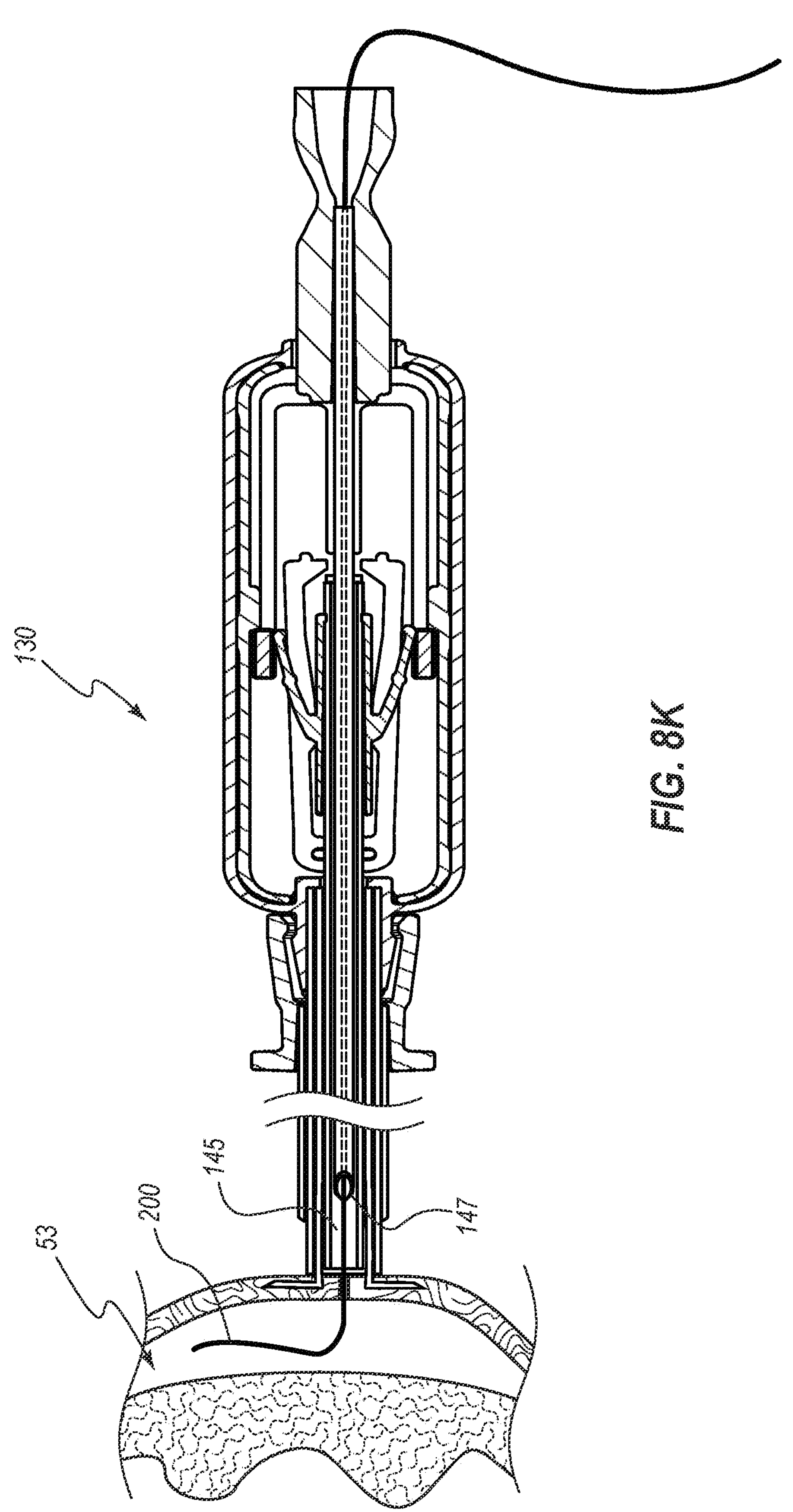
FIG. 8K depicts another stage in which the tissue engagement device has been returned to the partially deployed state, such as that of FIGS. 5C and 7C, in that the actuator remains fully deployed and the access assembly has retracted.

FIG. 8K depicts another stage in which the tissue engagement device 130 has been returned to the partially deployed state, such as that of FIGS. 5C and 7C. In particular, the access device 147 has been retracted. From this stage, the actuation member 145 may subsequently be retracted and then the device 130 can be removed from the patient P. The distal end of the guidewire 200 can remain in place within the pericardial space 53 as the tissue engagement device 130 is withdrawn. Although the arms will be in a retracted state during removal of the device 130, positioning of the guidewire 200 will be relatively unaffected during withdrawal of the device 130. In particular, as the device 130 is withdrawn, the arms 108*a*, 108*b* pass by the guidewire 200. Stated otherwise, the guidewire 200 can pass through openings 225, 226 defined by the arms 108*a*, 108*b*, even though the arms 108*a*, 108*b* cover the distal opening of the actuation member 145. The openings 225, 226 can be seen, for example, in FIGS. 11C and 11D.

Figure 9:
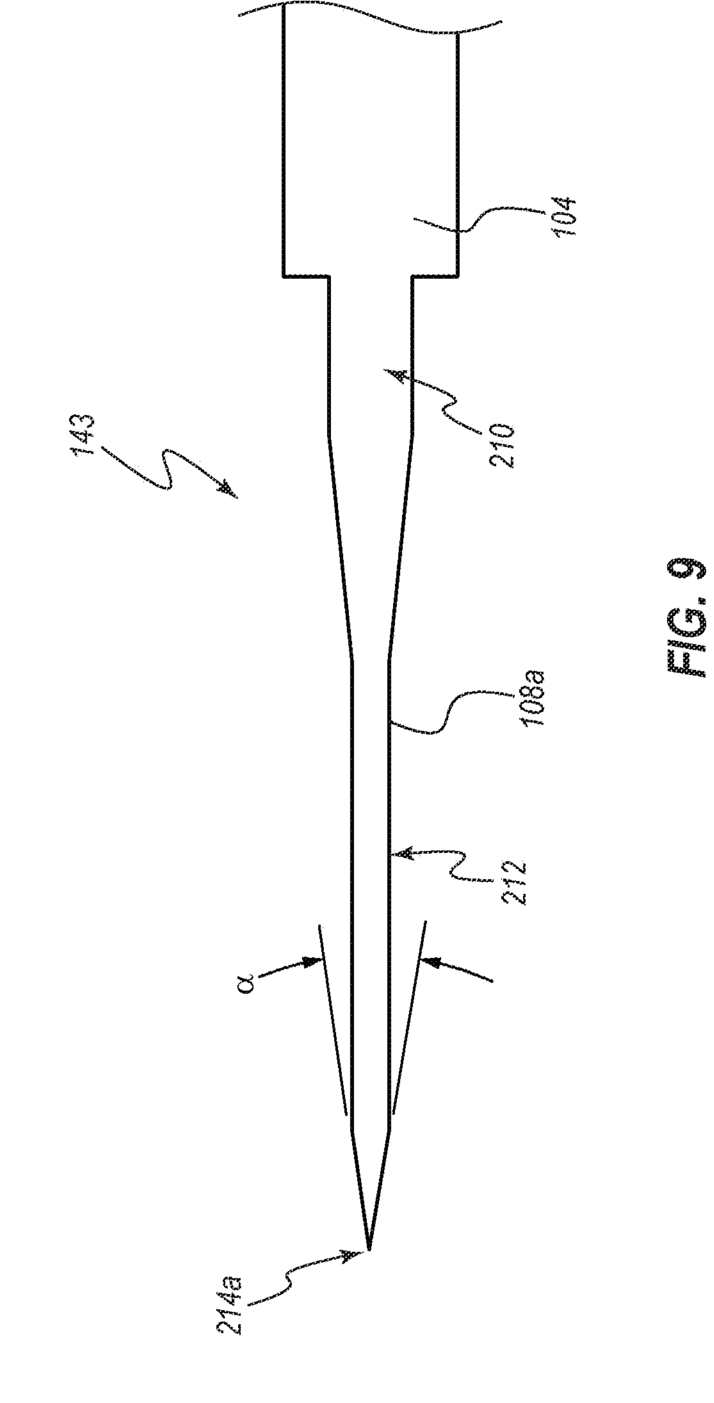
FIG. 9 is a side elevation view of an embodiment of an engagement element during an early stage of manufacture.

FIG. 9 depicts an embodiment of an engagement element 143 during a stage of a manufacturing process therefor. In the illustrated embodiment, the engagement element 143 is formed from a unitary piece of material. Any suitable material is contemplated. The material can desirably exhibit the properties described herein. In some embodiments, the engagement element 143 is formed from a unitary piece of stainless steel that has been formed as a tube.

Prior to the stage of the manufacturing method depicted in FIG. 9, portions of the tube are cut or otherwise removed to form the arms or tines 108*a*, 108*b* (the tine 108*b* is hidden in FIG. 9, but is shown in other figures, such as FIG. 10A). In some embodiments, the tines are laser cut. The tines 108*a*, 108*b* can extend distally from the remaining portion of the original tube, which is also referred to herein as the cannular base 104.

The tines 108*a*, 108*b* can each include a relatively wide base region 210, which can extend distally from a distal end of the cannular base 104. In various embodiments, a width of the base region 210 can be no greater than about ⅔, ½, or ⅓ of a diameter of the cannular base 104. The base region 210 can have an angled step down to a displacement region 212. The displacement region 212 of each arm is the region of greatest displacement during use. A thinner displacement region 212 can permit a compact or low profile design. In particular, a thin displacement region can be desirable where the tines 108*a*, 108*b* cross one another in the retracted orientation and move past each other during deployment. In various embodiments, a thickness of the displacement region is no greater than about ½, ⅓, ¼, ⅙, or ⅛ of the diameter of the cannular base 104.

Removal of portions of the original tube can also yield a piercing surface 214*a*, 214*b* (see also, e.g., FIG. 10A). In the illustrated embodiment, the piercing surfaces 214*a*, 214*b* are fashioned as pointed ends or barbs at the distal tips of each tine 108*a*, 108*b*. An attack angle $\alpha$ of the piercing surfaces 214*a*, 214*b* can be selected to provide ready engagement with the target tissue layer. In various embodiments, the attack angle $\alpha$ is no greater than about 10, 15, 20, 25, or 30 degrees.

Figure 10B:
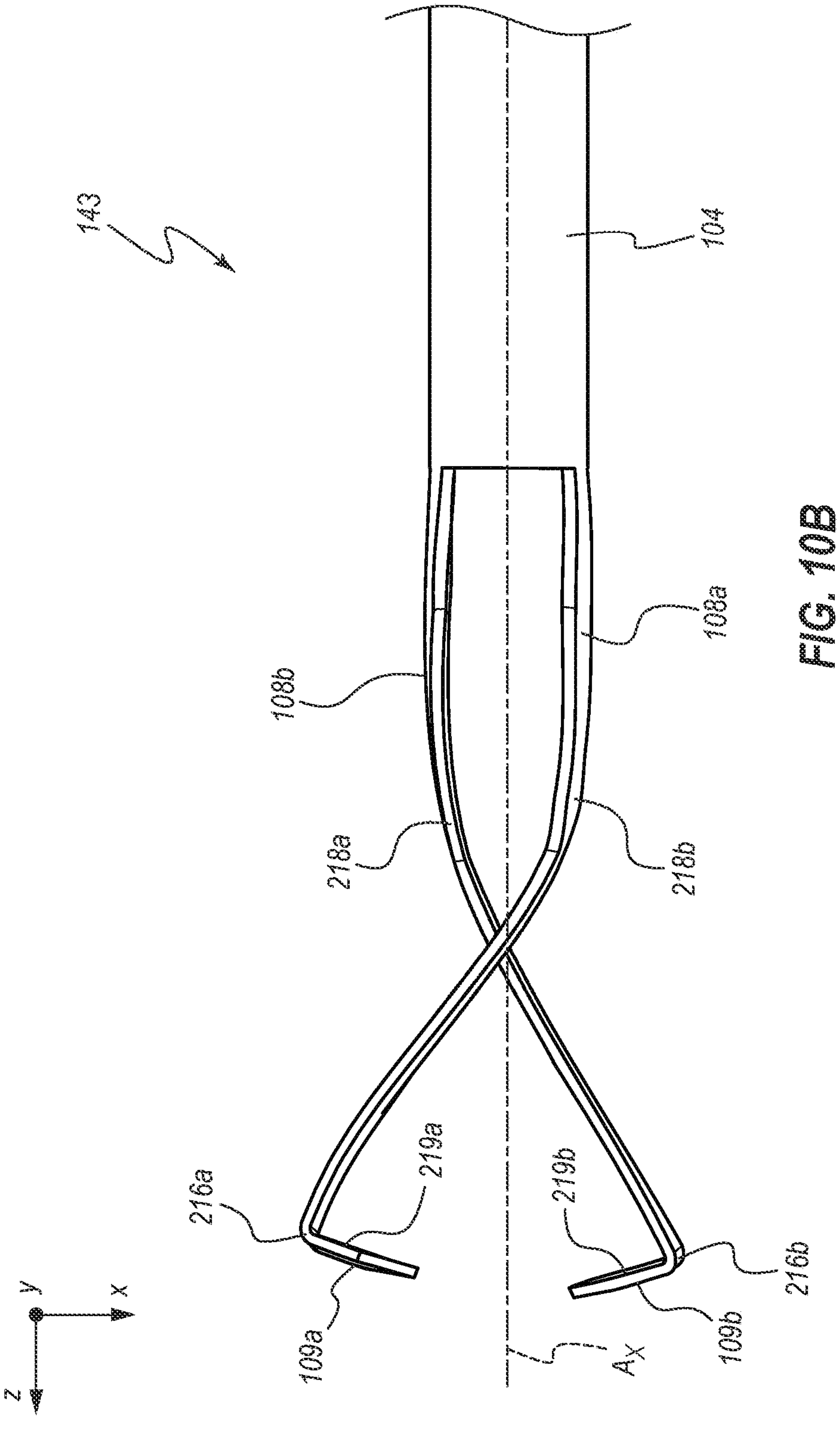
FIG. 10B is a top plan view of the engagement element after manufacture of the engagement arms.

FIG. 10A is a side elevation view of the engagement element 143 after further processing, and FIG. 10B is a top plan view thereof. In further process stages that result in the configuration depicted in FIGS. 10A and 10B, the tines 108*a*, 108*b* are bent about multiple axes. In some embodiments, a primary bend 216*a*, 216*b* is made by rotating the distal end of the tines 108*a*, 108*b* about the y-axis. In particular, the tine 108*a* is rotated in a first direction about the y-axis, and the tine 108*b* is rotated in an opposite direction about the y-axis. In various embodiments, an angle of plastic deformation that results from the bending can be within a range of from about 30 degrees to about 120 degrees, from about 45 degrees to about 115 degrees, or may be no more than about 45, 60, 90, or 115 degrees.

The primary bends 216*a*, 216*b* can yield the engaging members 109*a*, 109*b*. Retention surfaces 219*a*, 219*b* at the proximal sides of the engaging members 109*a*, 109*b* may vary in effectiveness at holding the target tissue layer, depending on the angle of plastic deformation of the bends 216*a*, 216*b*.

The tines 108*a*, 108*b* can be rotated and permanently bent in the same direction about the z-axis. Additionally, or alternatively, the tines 108*a*, 108*b* can be rotated and permanently bent in opposite directions about the x-axis. The latter bending may be referred to as splining, and can permit the tines 108*a*, 108*b* to move past one another when an additional permanent bend, or secondary bend 218*a*, 218*b* (FIG. 10) is formed.

As shown in FIG. 10B, in some embodiments, the tines 108*a*, 108*b* define a natural orientation in which the lateral width at a distal end of the tines 108*a*, 108*b* is greater than a diameter of the cannular base 104. As a result, when the tines 216*a*, 216*b* are received within the sheath 131, which has an interior diameter that only slightly exceeds the outer diameter of the base 104, the tines 108*a*, 108*b* are spring-loaded. That is, the tines 108*a*, 108*b* naturally attempt to assume the configuration shown in FIGS. 10A and 10B, but are prevented from doing so by the sheath 131 (see FIG. 5B). Providing such a pre-load to the tines 108*a*, 108*b* allows them to naturally return to the constrained orientation depicted in FIG. 5B after the actuation member 145 is retracted.

FIGS. 11A-11D depict various views of the engagement element 143 when in the constrained configuration that is provided by the sheath 131, such as in the arrangement depicted in FIG. 5B. For clarity, the sheath 131 is not shown in these views. In this operative state, the tines 108*a*, 108*b* cross each other at a position distal of the distal end of the cannular base 104. In this particular embodiment, the tines 108*a*, 108*b* contact one another at a crossing point 220. Other embodiments may cross one another near a crossing point, but not contact each other thereat. The crossing point in such arrangements may be the midpoint of a minimum distance between the tines 108*a*, 108*b* where they cross. As previously mentioned, the tines 108*a*, 108*b* can define openings 225, 226 through which a guidewire may readily pass during use.

As can be appreciated from the foregoing, in certain embodiments, the tines 108*a*, 108*b* can be positioned diametrically opposite one another. When in a retracted state, the tines 108*a*, 108*b* can be in a substantially bent configuration. When actuated, a proximal portion of each tine 108*a*, 108*b* that is constrained within the sheath 131 can be substantially straightened. The straightened tines may be substantially parallel to each other and/or substantially parallel to a longitudinal axis of the cannular base 104. A length of each tine 108*a*, 108*b* may be sufficiently long to prevent plastic deformation of the tines 108*a*, 108*b* during deployment. The tines are formed in an elastically resilient fashion that permits them to automatically and naturally return to the pre-deployment state after deployment.

Further, as is clear from the foregoing disclosure, in some embodiments, the first and second piercing surfaces 214*a*, 214*b* are moved at an exterior of the sheath throughout transition of the actuation cannula from the retracted position to the extended position. In other or further embodiments, the actuation cannula 245 defines a longitudinal axis, and the first and second tines 108*a*, 108*b* rotate about the longitudinal axis as the actuation cannula transitions from the retracted position to the extended position. Stated otherwise, the first and second tines 108*a*, 108*b* can progress toward their pre-bent state during actuation, and can return to their formed condition during retraction.

Figures 12A, 12B:
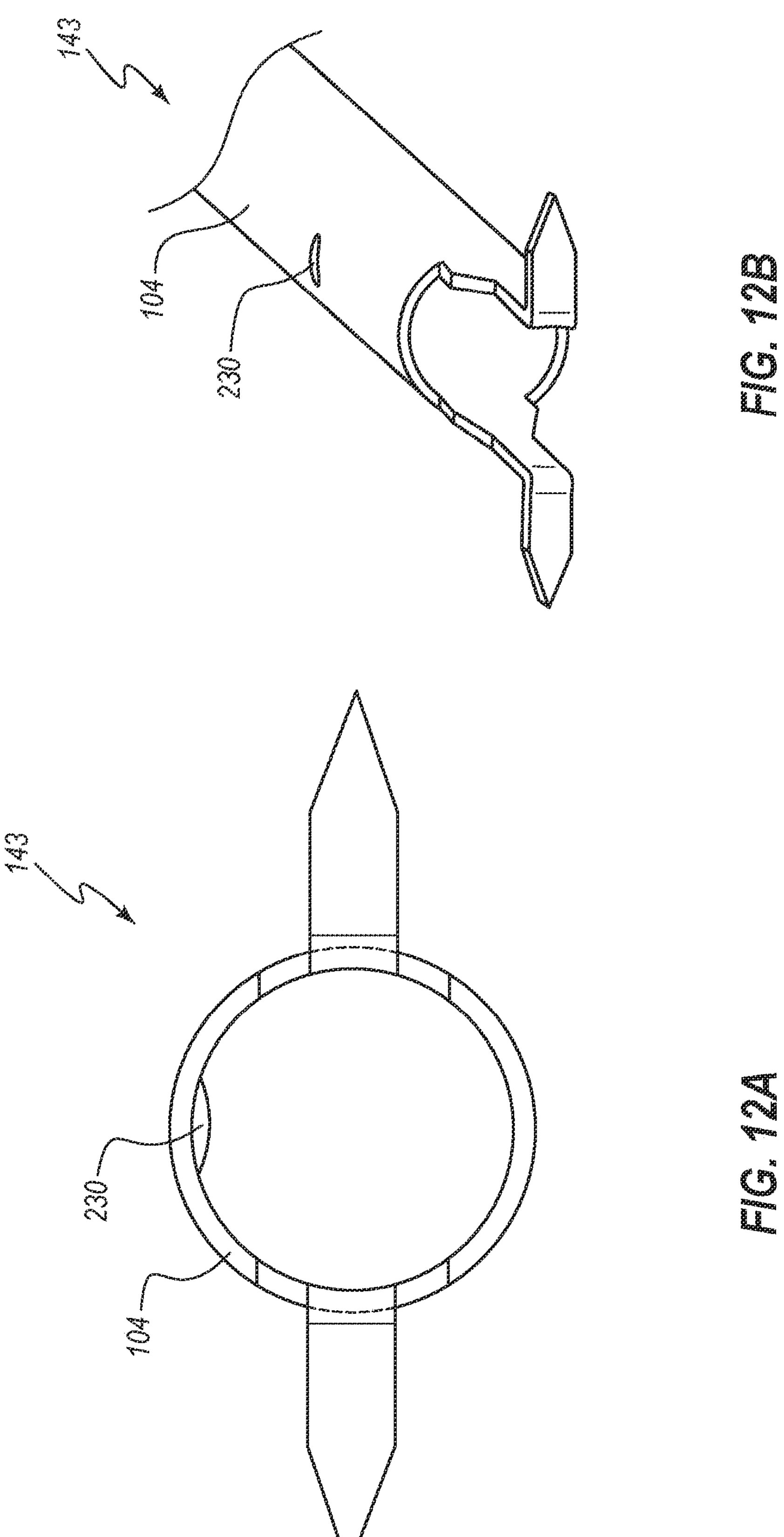
FIG. 12A is a front elevation view of the engagement element in the constrained state when actuated from within, such as via an actuation cannula—not shown in the present view (but see, e.g., FIG. 5C)
FIG. 12B is a perspective view of the engagement element in the constrained state when actuated from within, such as via an actuation cannula—not shown in the present view (but see, e.g., FIG. 5C)

With reference to FIGS. 12A and 12B, certain embodiments of the engagement element 143 can include a centering protrusion 230. In the illustrated embodiment, the centering protrusion 230 is an inwardly directed bump 230 that is impressed into the cannular base 104. In other embodiments, the centering protrusion 230 may instead be formed from a different material and fixedly secured to the inner wall of the cannular base 104.

Figure 13:
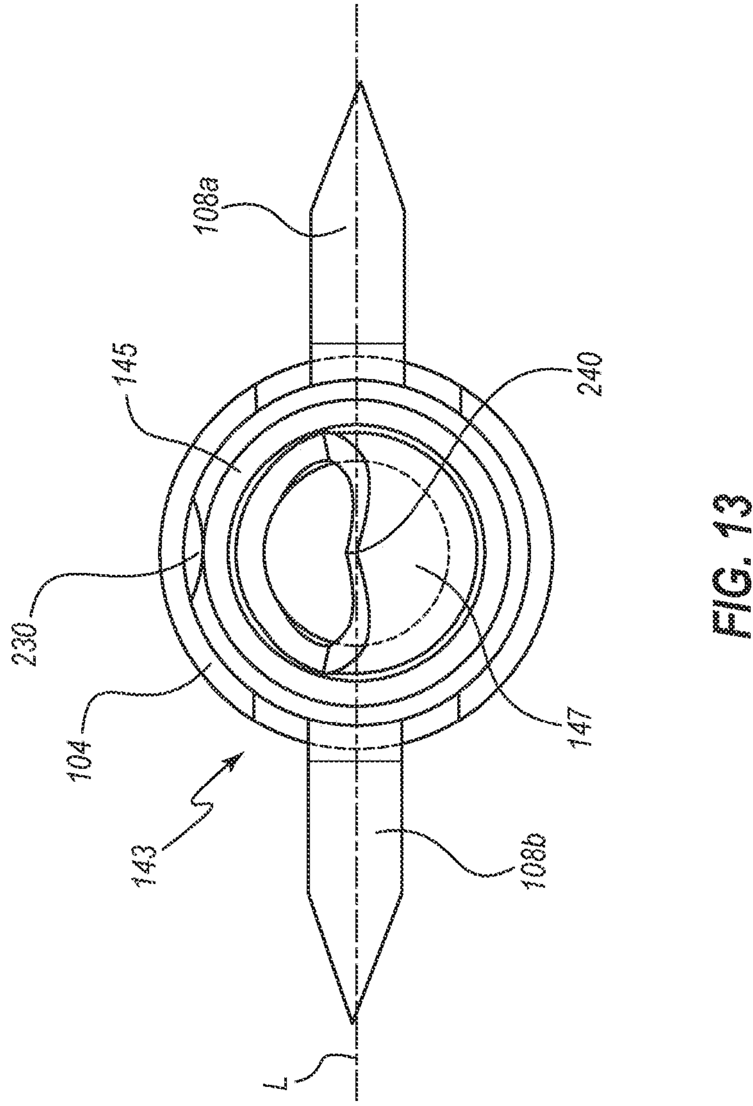
FIG. 13 is a front elevation view (e.g., an end-on view directed proximally) of a distal end of an embodiment of an engagement device in a fully deployed configuration.

As shown in FIG. 13, the centering protrusion 230 constrains movement of the actuation member 145 (e.g., constrains lateral movements relative to a longitudinal axis), which in turn constrains movement of the access device 147. This arrangement can ensure that a distal tip 240 of the access device 147 is substantially centered relative to the engagement element 143. In some embodiments, during actuation of the access device 147, the distal tip 240 can pass through a line L that extends through the distal tips of the tines 108*a*, 108*b*. Such an arrangement can aid in delivering the tip 240 through a portion of the pericardium that is between the tines 108*a*, 108*b* and is in tension due thereto. For example, this can permit the tip 240 to pass through a relatively flat or plateaued region at the apex of a tented portion of the pericardium, as previously discussed.

Figure 14B:
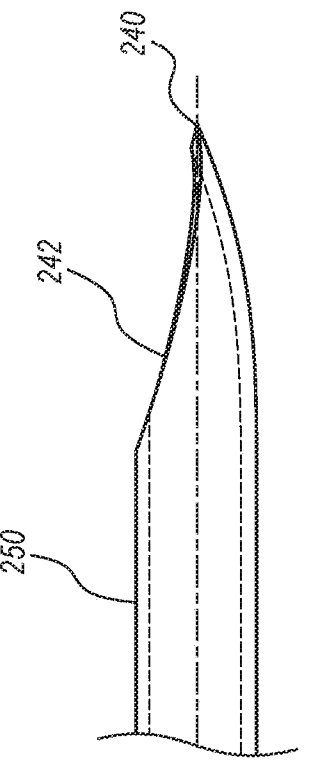
FIG. 14B is a side elevation view of the distal end of the needle of FIG. 14A.
Figure 14A:
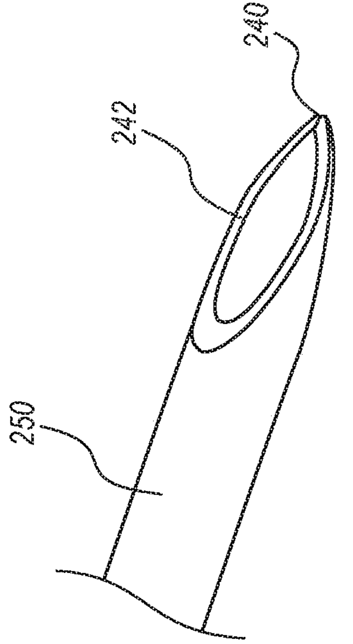
FIG. 14A is a perspective view of a distal end of an embodiment of a needle suitable for use with embodiments of engagement devices disclosed herein.

As shown in FIGS. 14A and 14B, in some embodiments, the access device 147 can be a needle 250 having a centered distal tip 240. In some instances, the needle 250 is formed with a bevel 242 (e.g., one or more of a bias grind, a lancet grind, etc.), and is then bent to move the distal tip 240 into alignment with a longitudinal axis of the needle 250.

FIGS. 15-20 depict another embodiment of a tissue engagement system 300 that can resemble the tissue engagement systems discussed above in many respects. Accordingly, like features are designated with like reference numerals, with the leading digits incremented to "3." Relevant disclosure set forth above regarding similarly identified features thus may not be repeated hereafter. Moreover, specific features of the tissue engagement system 300 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the tissue engagement system 300. Any suitable combination of the features and variations of the same described with respect to the tissue engagement systems discussed above can be employed with the tissue engagement system 300, and vice versa.

Figure 17:
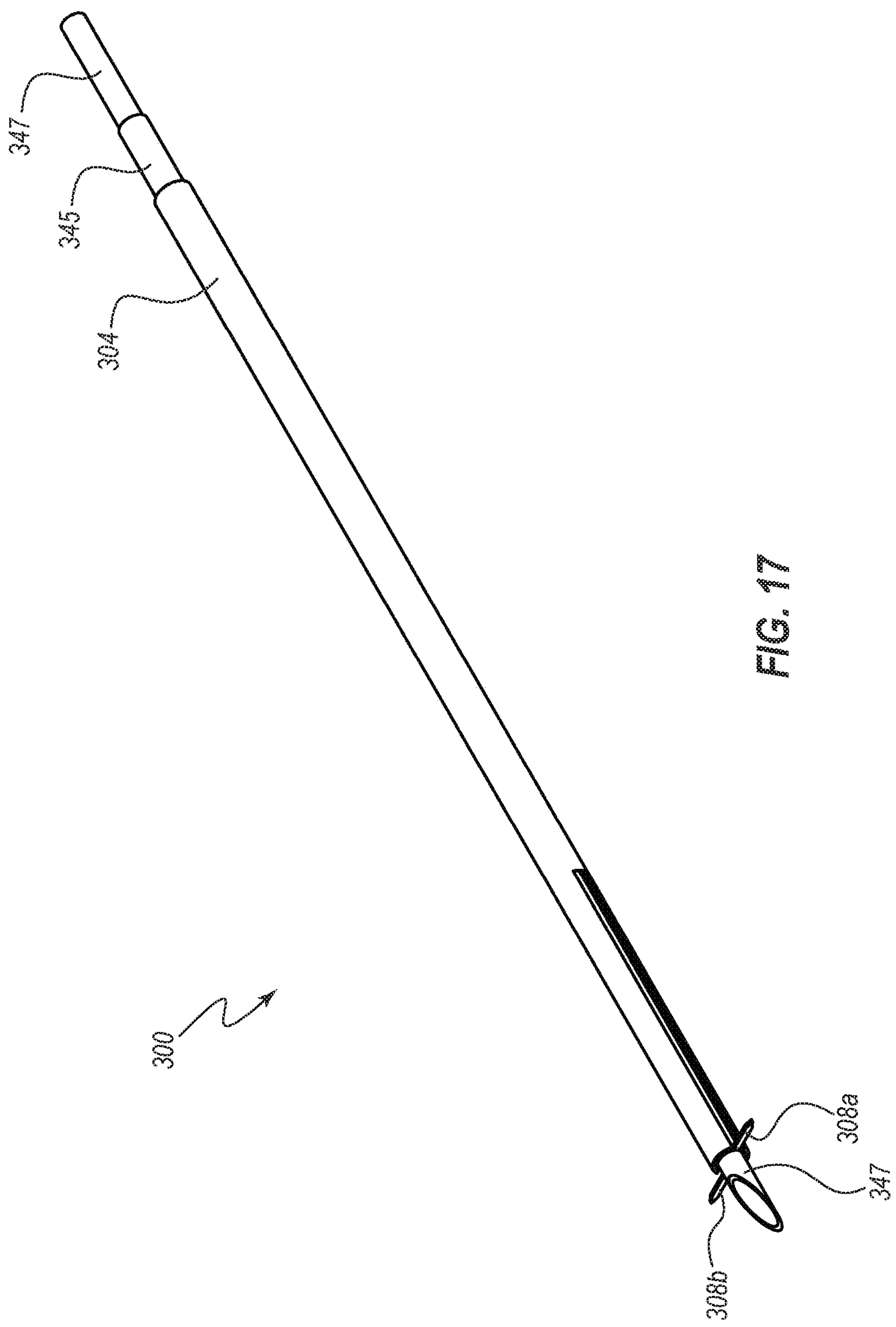
FIG. 17 is another perspective view of the tissue engagement system of FIG. 15 that depicts the system in a fully deployed state in which engagement arms have been extended and an access device has been deployed.

Referring to FIG. 17, the system 300 for engaging a tissue layer and for providing access to a region beneath the tissue layer includes a tissue engagement element 343 having a cannular base or housing 304 with integrated tissue engaging members 308*a*, 308*b*, and a cannula 345 to activate the tissue engaging members 308*a*, 308*b* within the lumen of the housing 304, and a tissue piercing member 347 within with lumen of the cannula 345, to secure access to the region beneath the tissue layer.

Figure 15:
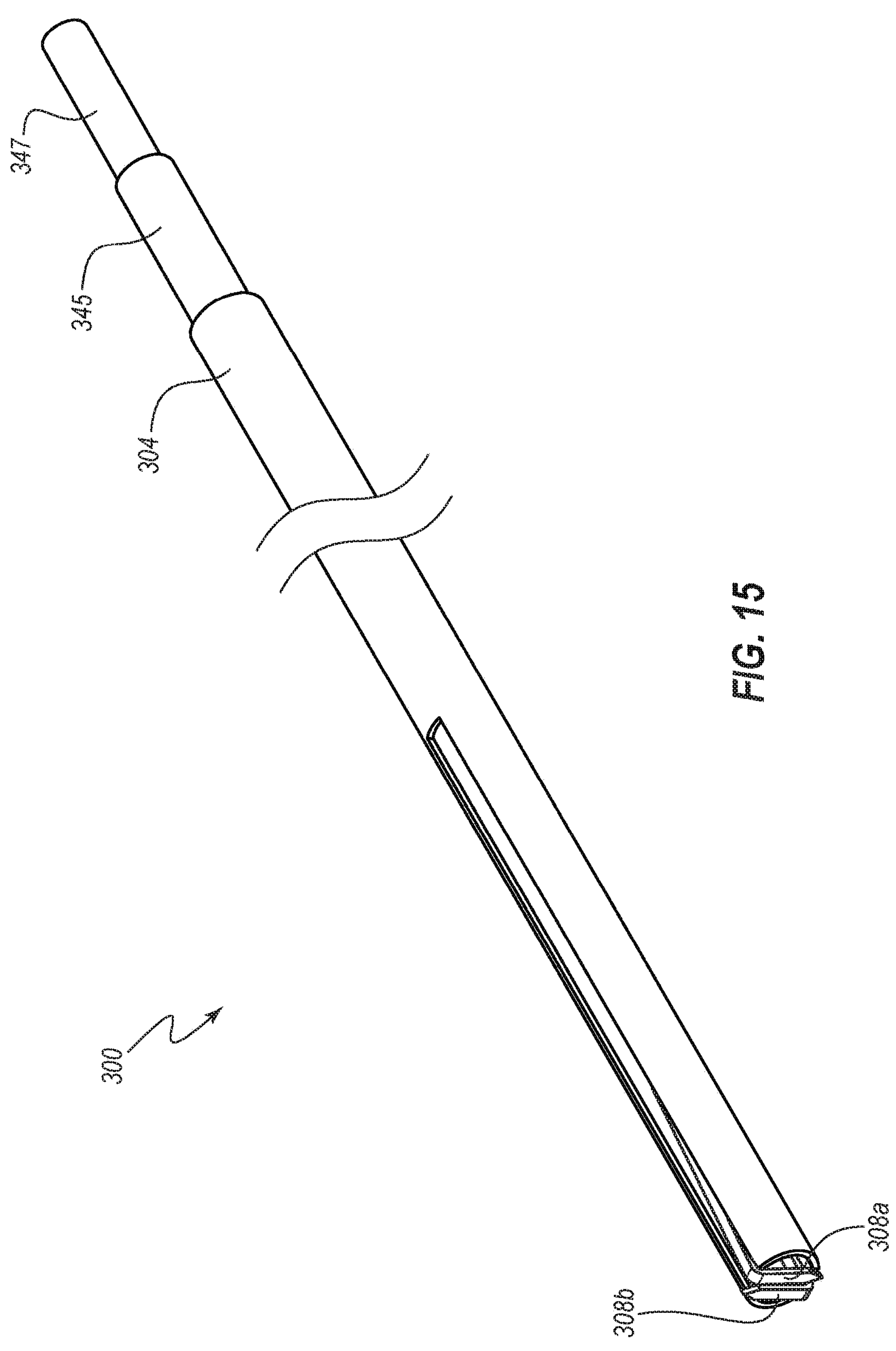
FIG. 15 is a perspective view of another embodiment of a tissue engagement system that is depicted in a fully retracted state.

Referring to FIG. 15 there is depicted an embodiment of a system 300 with the cannula 345 and the tissue piercing member 347 retracted within the housing 304, such that the cannula 345 and the tissue piercing member 347 are not in contact with the tissue engaging members 308*a*, 308*b*.

Figure 16:
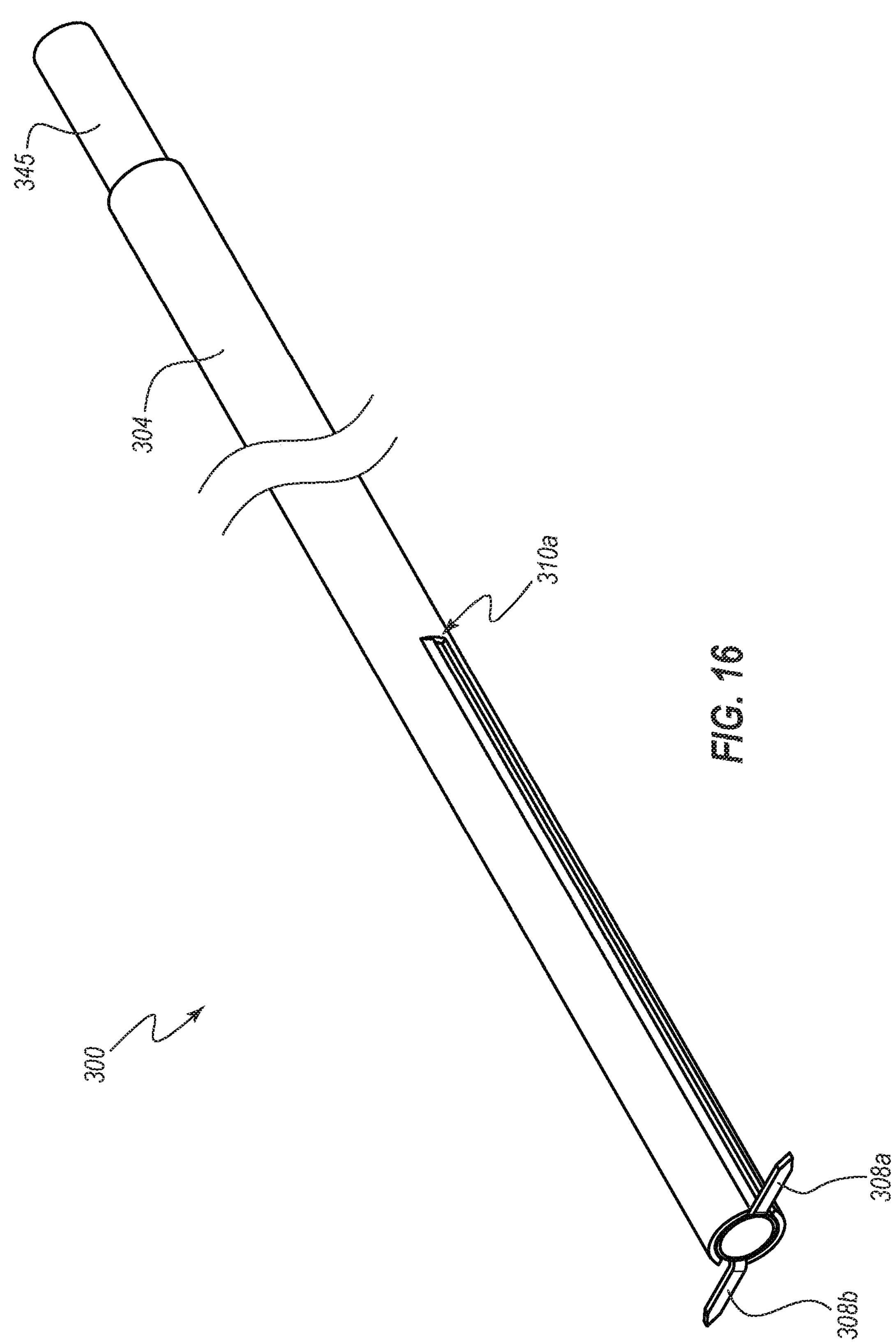
FIG. 16 is another perspective view of the tissue engagement system of FIG. 15 that depicts the system in a partially deployed state in which engagement arms have been extended.

Referring to FIG. 16 there is shown an embodiment of the housing 304 with the tissue engaging members 308*a*, 308*b* fully deployed. The distal end of the cannula 345 is advanced to the distal end of the housing 304, thereby causing the tissue engaging members 308*a*, 308*b* to deploy outward.

Figure 18:
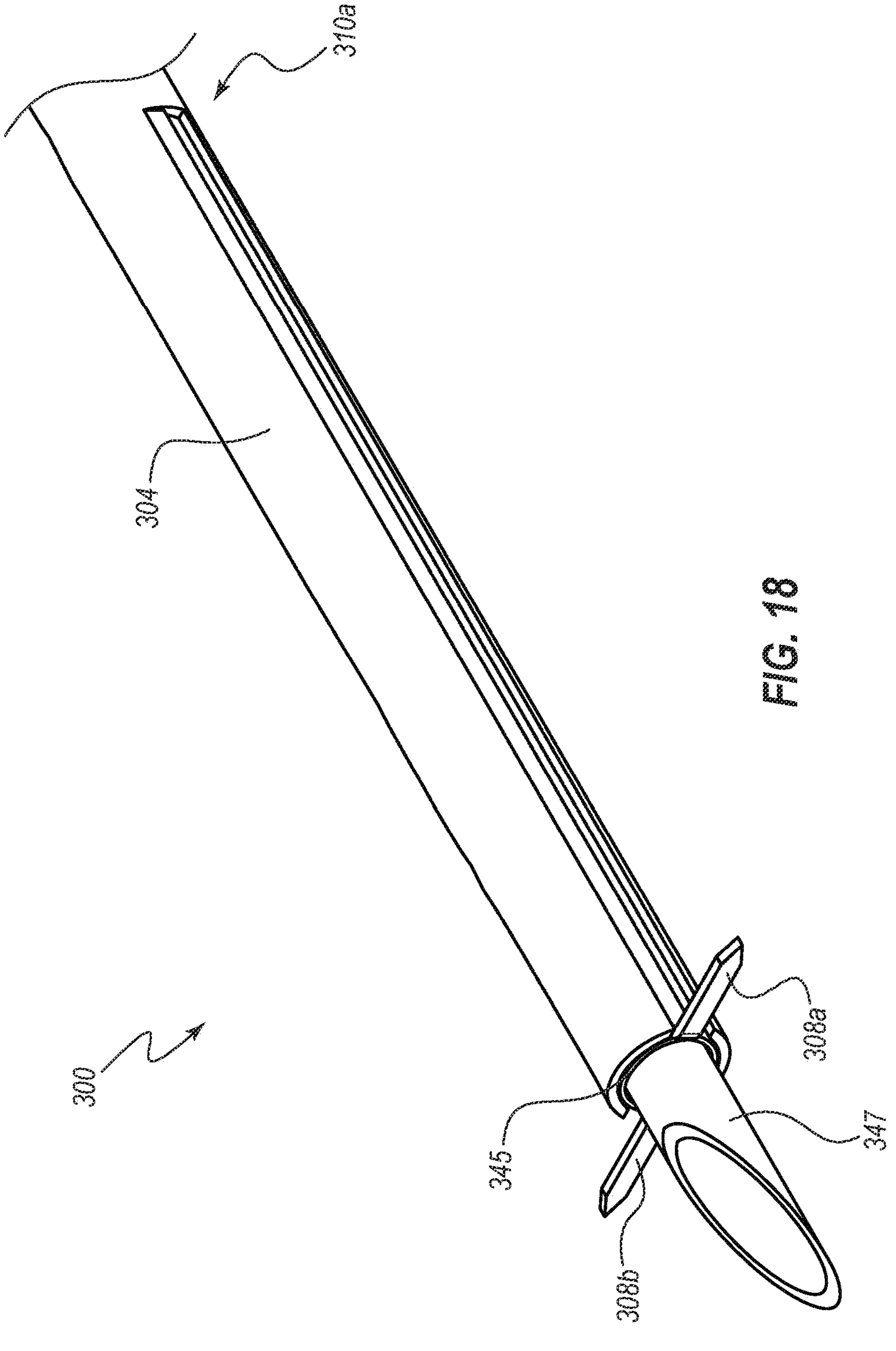
FIG. 18 is an enlarged perspective view of a distal portion of the tissue engagement system in the fully deployed state of FIG. 17.

Referring to FIG. 18 there is shown an embodiment of the system 300, with the distal end of the cannula 345 advanced from the proximal end 310*a* of the tissue engaging member 308*a* to the distal end of the housing 304, thereby deploying the tissue engaging member 308*a*. The tissue engaging member 308*b* is deployed in a like manner. The tissue piercing member 347 is advanced beyond the distal end of the housing 304.

Figure 19:
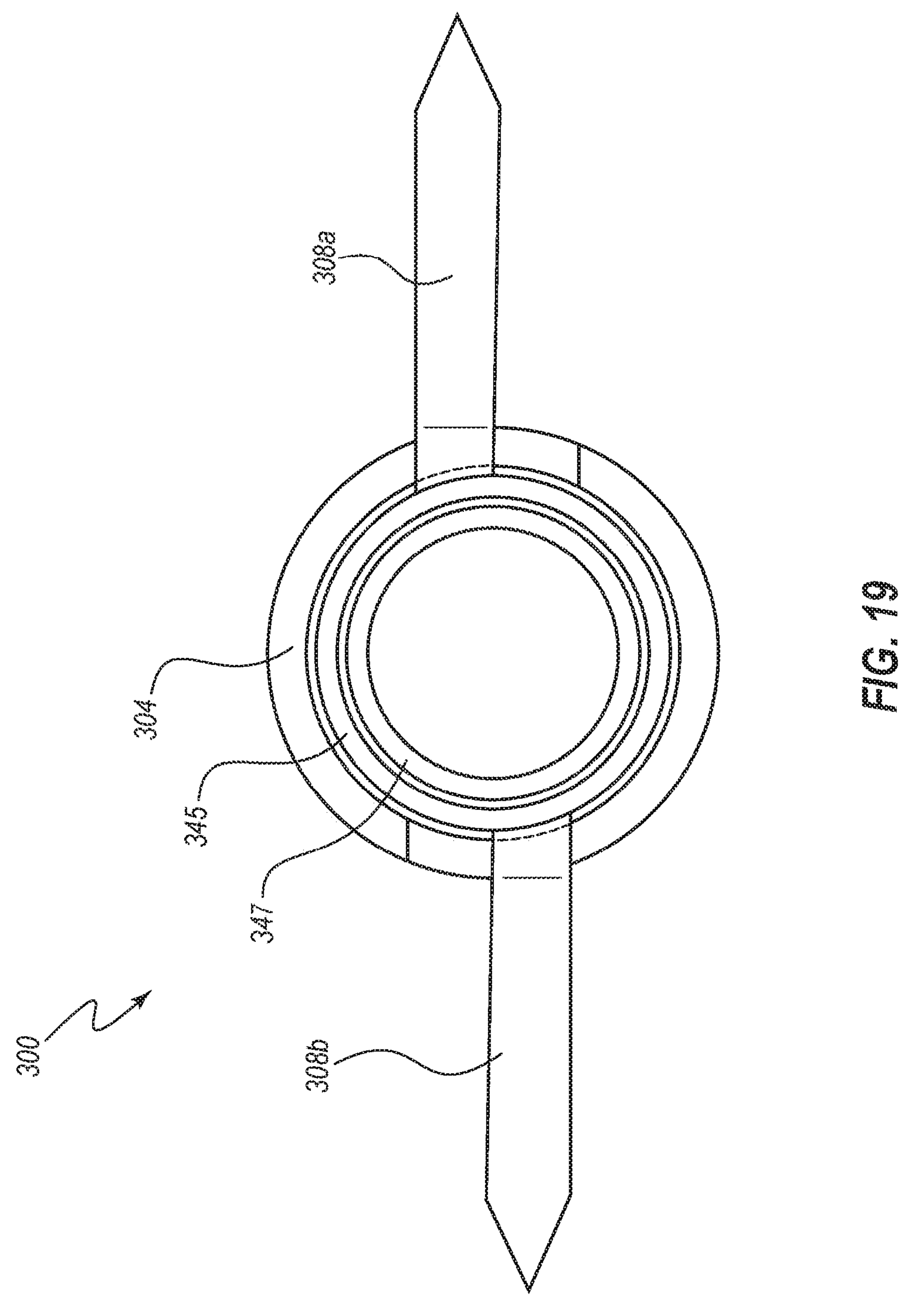
FIG. 19 is a front elevation view (e.g., an end-on view directed proximally) of a distal end of the tissue engagement system in the fully deployed state of FIG. 17.

Referring to FIG. 19 there is shown a front view of one embodiment depicting the offset nature of the tissue engaging members 308*a*, 308*b* at the distal end of the housing 304.

Figure 20:
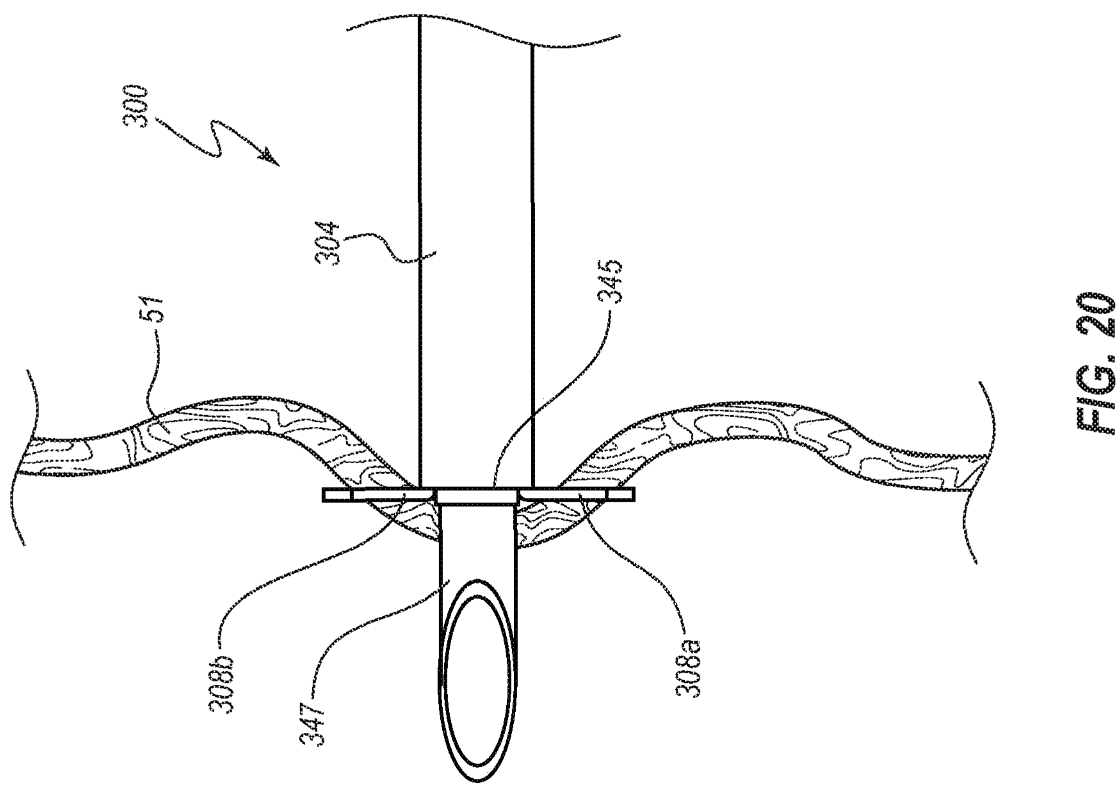
FIG. 20 is a top plan view of the distal end of the tissue engagement system in the fully deployed state that depicts the system having engaged a tissue layer via deployed arms and pierced the tissue layer via the access device to provide access to a region below the tissue layer.

Referring to FIG. 20 there is depicted a side view of the engagement of a tissue layer 51 by the tissue engaging members 308*a*, 308*b*, and the deployment of the tissue piercing member 347 into the space under the tissue layer 51.

As shown in these drawings, the illustrated system 300 includes an elongated housing 304, which may also be referred to as a cannula, having a proximal and distal end. The distal end terminates at a distal tip of the needle 347 when said needle 347 is extended as in FIG. 17 and the distal end terminates at the distal tip of the housing 304 when said needle 347 is retracted as in FIG. 15. The needle 347 can be advanced to aid insertion into the patient skin as in FIG. 17, and then retracted as in FIG. 15 as the device 300 is moved towards the tissue layer 51 to be engaged, to reduce damage to tissues that could be caused by an extended needle. The illustrated embodiment is particularly well suited for providing access to the pericardial space using a subxiphoid approach. The non-deployed tissue engaging members 308*a*, 308*b* as shown in FIG. 15 may effectively pass through soft tissue of a patient until contacting the pericardium, and can be sufficiently blunt to inhibit puncture or piercing of the pericardium or other tissues when advanced.

The housing 304 may be formed of any suitable material. In some embodiments, the housing 304 is metallic, whereas in other or further embodiments, the housing 304 can be formed of a substantially rigid plastic.

The needle 347 may be formed of any suitable material. For example, in some embodiments, the needle 347 is formed of stainless steel. The material is chosen such that it is sufficiently rigid to pierce the tissue layer.

The cannula 345 may be formed of any suitable material. For example, in some embodiments, the cannula 345 is formed of stainless steel. The material chosen such that is sufficiently rigid and strong to deploy the tissue engaging members 308*a*, 308*b*.

During use of the system 300, the needle 347 may be extended past the housing 304 to be inserted into a patient to the desired location, and the proximal end of the housing 304 can remain at an exterior of the patient. In one embodiment, the system is inserted into the patient with the needle 347 in the retracted position as shown in FIG. 15 via an incision in the patient at the desired location. In some embodiments, the system 300 includes one or more actuators at the proximal end by which a user can deploy the needle 347 and/or the cannula 345. Any suitable actuator arrangement is possible. In other or further embodiments the cannula 345 and the access needle 347 may be manipulated directly by a user and advanced through the housing 304 without relying on any actuators.

In one embodiment, the system 300 comprises a first actuator at the proximal end of the system that is configured to deploy and/or retract the needle 347. While any suitable actuator arrangement is contemplated, the illustrated actuator comprises a button, switch, tab, or protrusion that is coupled to a proximal portion of the needle 347. In the illustrated embodiment, a relatively large annular space is depicted between an exterior surface of the access needle 347 and an interior surface of the cannula 345 and the interior surface of the housing 304. In some embodiments, this annular space is proportionally much smaller, minimized, or substantially eliminated. For example, a snug fit, a loose fit, or a minimal gap may be provided between at least a portion of an interior surface of the sidewall of the housing 304 and at least a portion of an exterior surface of the cannula 345, and the access needle 347, which can desirably reduce an overall diameter (e.g., maximum cross-sectional width, where the cross-section is not necessarily circular) of the system 300, or more particularly, an outer diameter of the housing 304. Such an arrangement also can reduce or avoid coring of tissue by the housing 304 as the system 300 is advanced into a patient.

FIG. 20 depicts the distal end of the system 300 as having been advanced into the patient and as having engaged the tissue layer 51. The tissue layer 51 is pulled back and the needle 347 is advanced into the space created under the tissue layer 41. A guidewire may be advanced through the lumen of the tissue piercing layer into the space under the tissue layer.

With reference again to FIG. 18, it is preferable that the length of the tissue engagement member 308*a*, 308*b* as it extends along the housing 304 is sufficiently long to prevent plastic deformation of the tissue engagement member 308*a*, 308*b* during actuation by the cannula 345.

With reference again to FIG. 19, the shape of the distal end of the tissue engagement members 308*a*, 308*b* are sharp such that they can cut into the tissue layer 51. The prongs are sufficiently long to engage the tissue layer 51, but they are not longer than the diameter of the housing 304, such that they do not extend beyond the border of the housing 304 when non-actuated as shown in FIG. 15. The prongs that engage the tissue layer may be bent at 90 degrees as shown, or they may be bent between 60 degrees to 120 degrees to enable tissue engagement and retention. The sharp tip of the prong may be cut from the center as shown, or it may be cut a variety of angles, or it may not be cut at any angle, to enable tissue engagement and retention. The prong profile and sharpness are designed to engage the tissue layer 50 at a low angle or a high angle. This allows for low and high approach angles, but particularly low-angles that can be particularly suitable for a low-angle, subxiphoid approach to the heart, for example.

With reference again to FIG. 15 and FIG. 19, the tissue engaging members 308*a*, 308*b* may be offset as shown, or they may not be offset such that they do not pass each other during activation by the cannula 345. The length of the prongs at the distal end of the tissue engaging members 308*a*, 308*b* may be constructed such that they do not extend beyond the diameter of the housing 304 when not activated by the cannula.

FIGS. 21A-22D illustrate another embodiment of a tissue engagement system that may be used to practice the invention. The tissue engagement system may comprise a tube 2111, a sheath 2131, an actuation member 2145, and a plurality of flexible arms (obscured) each comprising a tissue engaging member 2109*a*, 2109*b*.

As shown in FIGS. 21A-D, the arm and other internal structures are obscured, however, any arm known in the art or described herein may be utilized to practice the disclosure. Further, any of the aforementioned configurations, embodiments, or operation of the arm may be utilized in any of the described embodiments. FIGS. 22A-D depicts various views of an engagement element 2143 when in the constrained, or undeployed, state that is provided by the sheath 2131, as discussed with reference to the embodiment shown in FIGS. 11A-D.

The tube 2111, the sheath 2131, and the actuation member 2145 may be configured in any embodiment that may be desired, including the embodiments described herein. In some embodiments, each of the tissue engaging members 2109*a*, 2109*b* may define an angled distal end of their respective arms. It should be recognized that the angle of the tissue engaging members 2109*a*, 2109*b* may be any angle that may desired. For example, the angle of the tissue engaging members 2109*a*, 2109*b* may extend distally relative to the sheath and may be from about 5° to about 35°, from about 10° to about 30°, or from about 15° to about 25° when deployed. The angle of the tissue engaging members 2109*a*, 2109*b* relative to the arm is contemplated to secure to the target tissue following puncture. An insufficient angle may not sufficiently secure to the target tissue layer, which may cause the tissue engaging member to become disengaged during use.

In one embodiment, each of the tissue engaging members 2109*a*, 2109*b* may define a piercing surface 2214*a*, 2214*b*. As discussed herein, the piercing surface 2214*a*, 2214*b* may be operative to pierce a target tissue layer.

Figure 21A:
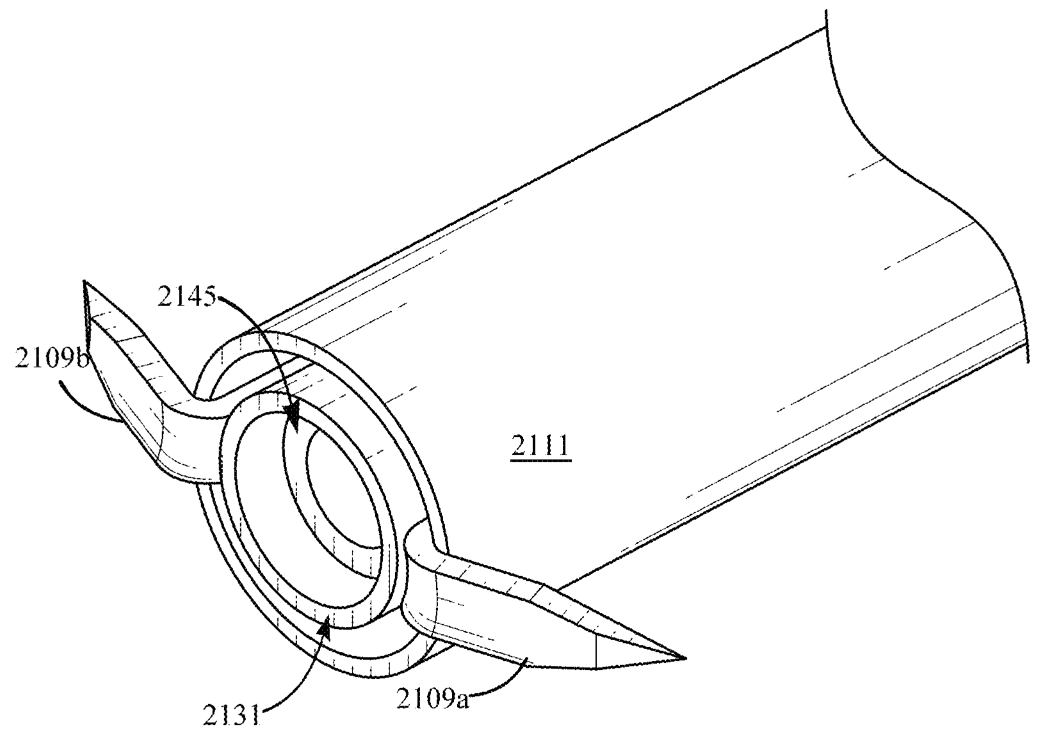
FIG. 21A is a perspective view of a distal end of an embodiment of an engagement device in a fully deployed configuration.
Figure 21B:
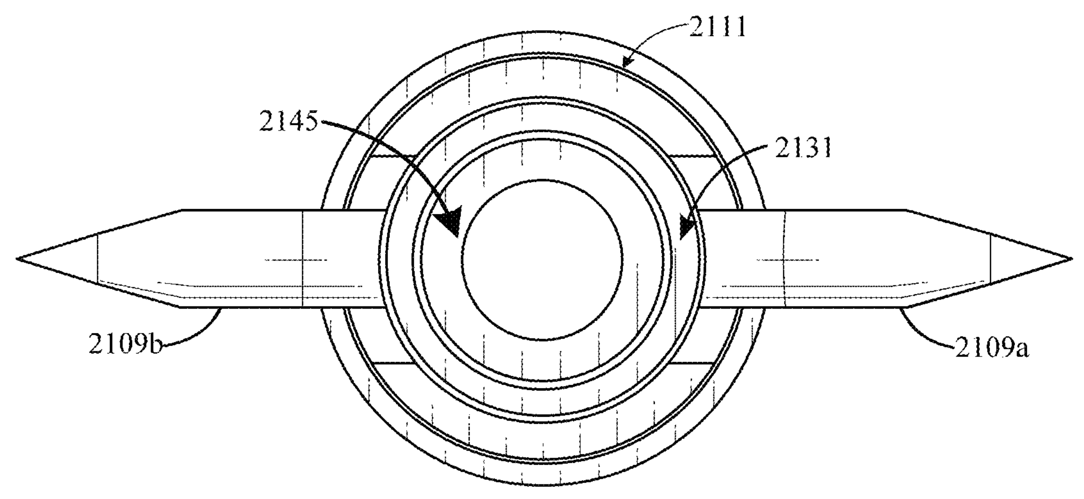
FIG. 21B is a front elevation view (e.g., an end-on view directly proximally) of a distal end of an embodiment of any engagement device in a fully deployed configuration.
Figure 21C:
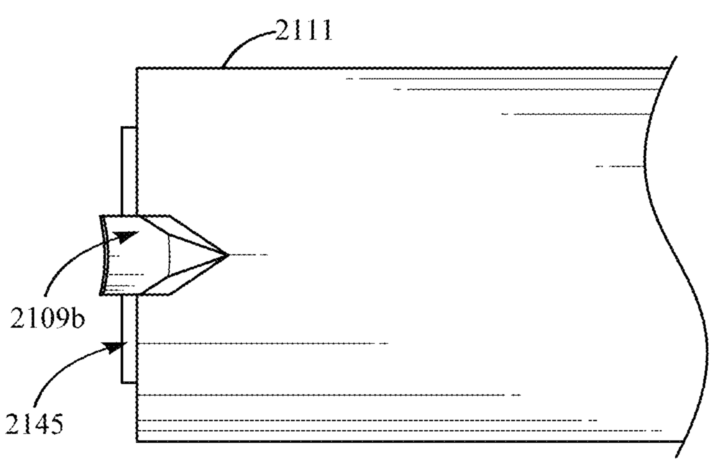
FIG. 21C is side view of a distal end of an embodiment of an engagement device in a fully deployed configuration.

FIG. 21A illustrates the tissue engagement system after the arms have been deployed. In one embodiment, each the tissue engaging members 2109*a*, 2109*b* may comprise a first face and a second face. The first face may be a proximally-facing face relative to the sheath 2131 when deployed and the second face may be a distal-facing face relative to the sheath 2131 when deployed. More particularly, the first face may be positioned to oppose the pericardium when pulling and the second face may be positioned to oppose the myocardium when pulling. In some embodiments, the second face may be configured to anchor the tissue engaging member 2109*a*, 2109*b* to the desired tissue layer during when deployed.

Figure 21D:
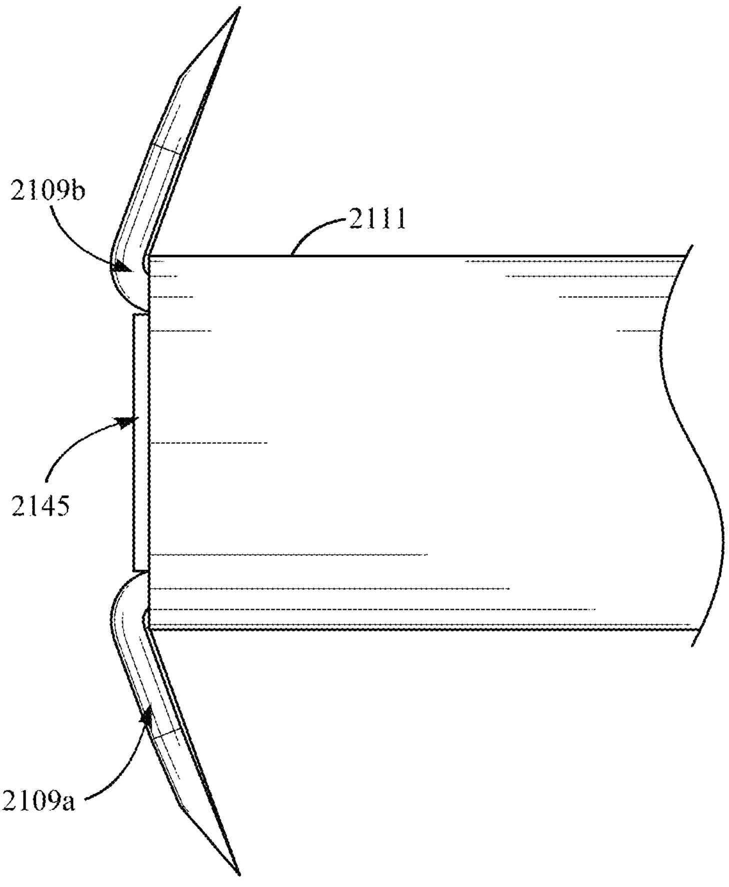
FIG. 21D is a top view of a distal end of an embodiment of an engagement device in a fully deployed configuration.
Figure 22A:
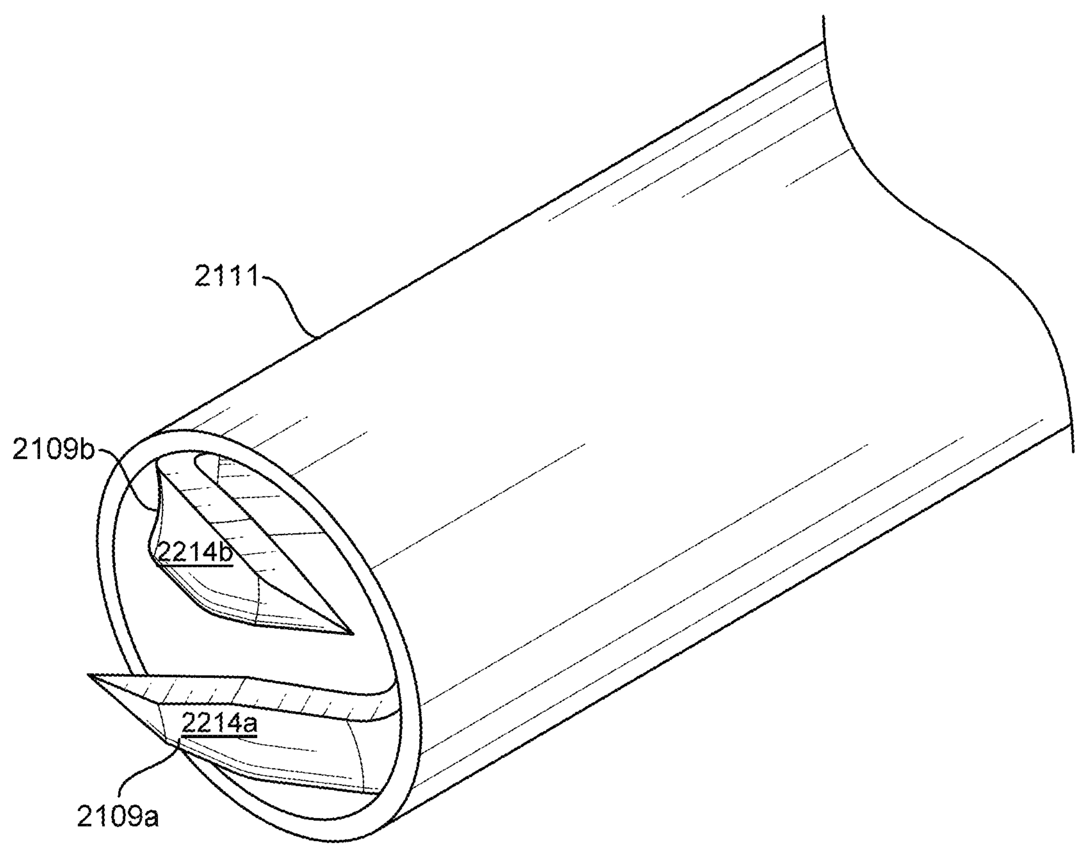
FIG. 22A is a perspective view of a distal end of an embodiment of an engagement device in a constrained state.
Figure 22B:
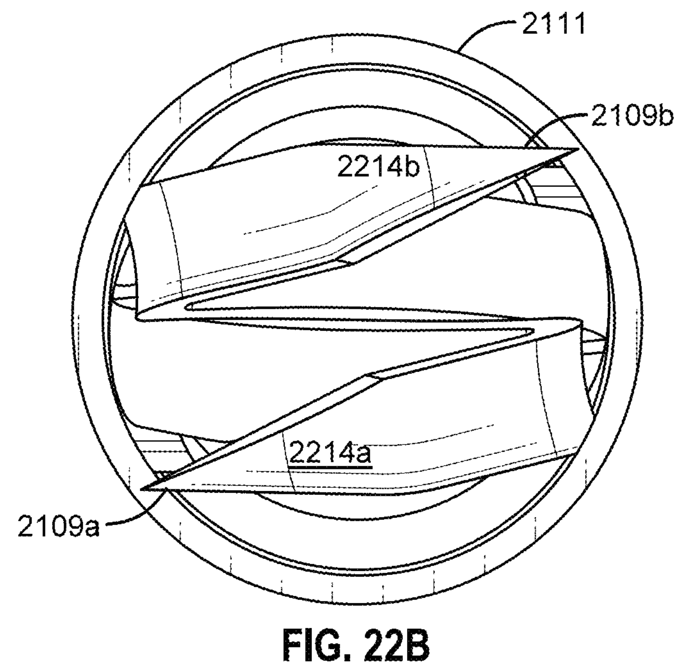
FIG. 22B is a front elevation view (e.g., an end-on view directly proximally) of a distal end of an embodiment of an engagement device in a constrained configuration.
Figure 22C:
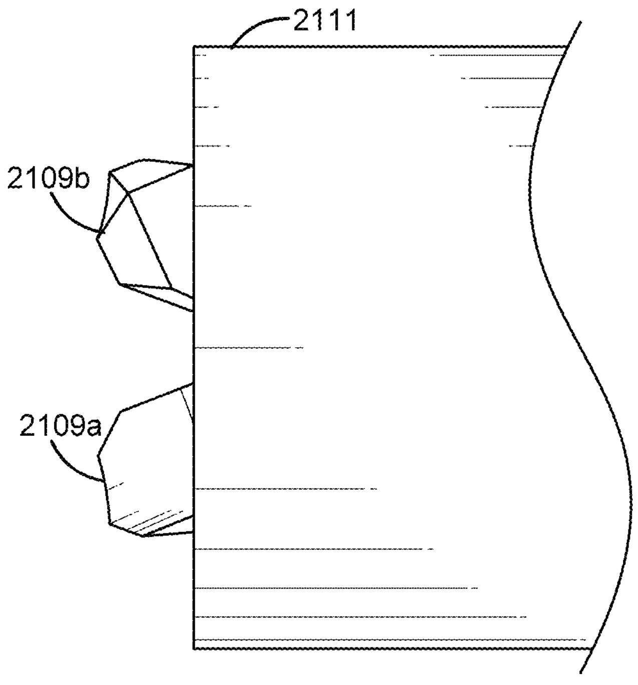
FIG. 22C is a side view of a distal end of an embodiment of an engagement device in a constrained configuration.
Figure 22D:
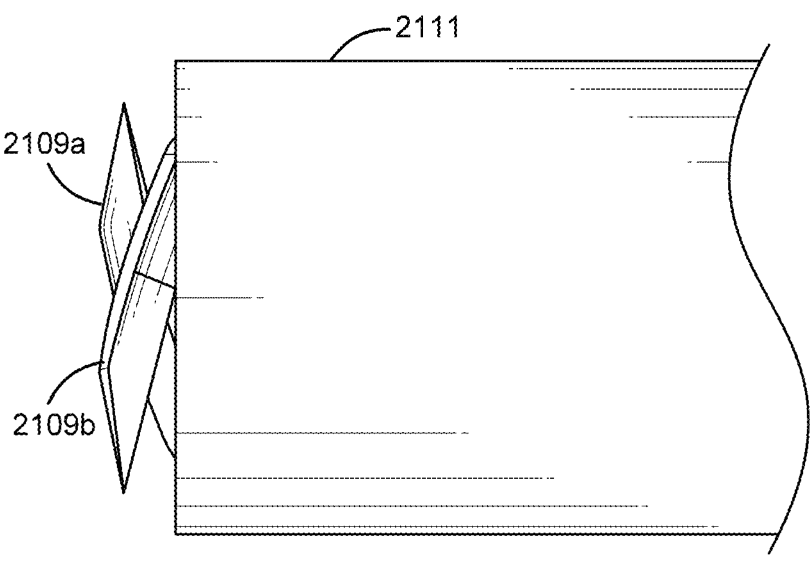
FIG. 22D is a top view of a distal end of an embodiment of an engagement device in a constrained configuration.

As seen in the embodiment illustrated in FIG. 21D, the second face may comprise a chamfer. It is contemplated that the second face comprising the chamfer may improve the tissue engaging members 2109*a*, 2109*b* engagement to the target tissue layer. More particularly, the chamfer may reduce the slippage of the tissue engaging member 2109*a*, 2109*b* relative to the target tissue when deployed. The chamfer on the tissue engaging members 2109*a*, 2109*b* may be any chamfer suitable to pierce the target tissue layer. For example, in one embodiment, the chamfer may have an angle from about 5° to about 35°, from about 10° to about 30°, or from about 15° to about 25°. Of course, other chamfer angles are contemplated and any angle suitable to create a sharpened tip is contemplated.

In another embodiment, the first face may comprise a chamfer. The chamfer may, in some embodiments, be configured to improve the piercing of the target tissue layer. In one such embodiment, the chamfer may be configured as the piercing surface and may be operative to pierce through any of the target tissue layer to permit the engagement members to extend through the target tissue layer.

In one embodiment, the length of each of the tissue engaging members 2109*a*, 2109*b* may be from about 0.2 inches (0.5 mm) to about 0.12 inches (3 mm). In a further embodiment, the length of each of the tissue engaging members 2109*a*, 2109*b* may be from about 0.4 inches (1 mm) to about 0.08 inches (2 mm). In still a further embodiment, the length of each of the tissue engaging members 2109*a*, 2109*b* may be about 0.07 inches (1.78 mm). Of course, any length of tissue engaging member 2109*a*, 2109*b* that a person of ordinary skill in the art may desire may be utilized to carry out the invention and may vary according to a desired use of the device. For example, the length of the tissue engaging members 2109*a*, 2109*b* being about 0.007 inches may be sufficient to pierce the pericardium to permit retraction. It is contemplated that too short of a tissue engaging member may result in piercing a ligament outside the pericardium, without engaging the pericardium, and if the tissue engaging member is too long it may inadvertently damage the myocardium.

In one embodiment, the thickness of each of the tissue engaging members 2109*a*, 2109*b* may be from about 0.001 inches (0.025 mm) to about 0.01 inches (0.3 mm). In a further embodiment, the thickness of each of the tissue engaging members 2109*a*, 2109*b* may be from about 0.007 inches (0.178 mm) to about 0.008 inches (0.203 mm).

It is contemplated that the length and thickness of the tissue engaging member 2109*a*, 2109*b* may, in some embodiments, be related. For example, in one embodiment, when the length of the tissue engaging members 2109*a*, 2109*b* is about 0.07 inches, the thickness may be from about 0.007 inches (0.178 mm) to about 0.008 inches (0.203 mm) to retain stiffness of the tissue engaging members 2109*a*, 2109*b*. Thus, in some embodiments, the thickness of the tissue engaging members 2109*a*, 2109*b* may be increased as the length is increased.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the terms "about" or "approximately." For each such reference, it is to be understood that, in some embodiments, the value, feature, or characteristic may be specified without approximation. For example, where qualifiers such as "about," "substantially," and "generally" are used, these terms include within their scope the qualified words in the absence of their qualifiers. For example, where the term "substantially planar" is recited with respect to a feature, it is understood that in further embodiments, the feature can have a precisely planar orientation.

Any reference throughout this specification to "certain embodiments" or the like means that a particular feature, structure or characteristic described in connection with that embodiment is included in at least one embodiment. Thus, the quoted phrases, or variations thereof, as recited throughout this specification are not necessarily all referring to the same embodiment or embodiments.

Similarly, it should be appreciated that in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements specifically recited in means-plus-function format, if any, are intended to be construed in accordance with 35 U.S.C. § 112(f). Embodiments of the invention in which an exclusive property or privilege is claimed are defined as follows.

What is claimed is:

1. A tissue engagement device comprising:

a sheath;

a first arm of which at least a proximal portion thereof is within the sheath, the first arm comprising a first tissue engaging member defining a first piercing surface;

a second arm of which at least a proximal portion thereof is within the sheath, the second arm comprising a second tissue engaging member defining a second piercing surface; and an actuation cannula configured to move distally from a retracted position to an extended position, wherein the actuation cannula moves at least a portion of each of the first and second arms into a region between an exterior surface of the actuation cannula and an interior surface of the sheath as the actuation cannula moves distally to the extended position, wherein each of the first and second tissue engaging members comprises a first face and a second face, wherein the first face is proximal-facing relative to the sheath and the second face is distally-facing relative to the sheath.

2. The tissue engagement device of claim 1, wherein the first and second arms extend distally from a distal end of a cannular base, and wherein at least a portion of the cannular base is positioned between the exterior surface of the actuation cannula and the interior surface of the sheath.

3. The tissue engagement device of claim 2, wherein, when the actuation cannula is in the retracted position, the first arm crosses the second arm at a position within the sheath that is distal to the distal end of the cannular base.

4. The tissue engagement device of claim 1, wherein the first face of the first and second tissue engaging members each comprise a chamfer extending off the face and configured to engage with a desired tissue layer.

5. The tissue engagement device of claim 1, wherein, when the actuation cannula is in the retracted position, the first arm crosses the second arm at a position within the sheath.

6. The tissue engagement device of claim 1, wherein the first and second tissue engaging members have a thickness from about 0.007 inches to about 0.008 inches.

7. The tissue engagement device of claim 1, wherein the first and second tissue engaging members have a length of about 0.07 inches.

8. The tissue engagement device of claim 1, wherein movement of the actuation cannula from the retracted position to the extended position transitions each of the first and the second arms from a bent configuration to a substantially straightened configuration.

9. The tissue engagement device of claim 1, wherein the first and second piercing surfaces are moved at an exterior of the sheath throughout transition of the actuation cannula from the retracted position to the extended position.

10. The tissue engagement device of claim 1, wherein the first and second arms are resiliently biased to automatically return to a low-profile orientation in which a maximum transverse dimension of the arms is smaller than an outer diameter of the sheath when the actuation cannula transitions from the extended orientation to the retracted orientation.

11. The tissue engagement device of claim 1, wherein a distal opening of the actuation cannula is substantially unobstructed by the first and second arms when the actuation cannula is in the extended position.

12. The tissue engagement device of claim 1, further comprising an access device within the actuation cannula configured to pass through a distal end of the actuation cannula when the actuation cannula is in the extended position and a guidewire positioned within the access device and configured to pass through a distal end of the access device.

13. The tissue engagement device of claim 12, wherein the guidewire is a flexible tip guidewire.

14. The tissue engagement device of claim 13, further comprising a locking mechanism configured to prevent the access device from being advanced through the distal end of the actuation cannula unless the actuation cannula is in the extended position.

15. The tissue engagement device of claim 14, further comprising a locking mechanism configured to prevent the actuation cannula from being transitioned from the extended position to the retracted position unless the access device is in a retracted state.

16. The tissue engagement device of claim 1, further comprising a guidewire having a flexible tip, the guidewire being configured to pass through an inner lumen of the access device when the actuation cannula is in the extended state; wherein the first piercing surface is at a distal tip of the first arm and the second piercing surface is at a distal tip of the second arm, and wherein the tip of the access device is configured to pass through a line that extends between the distal tips of the first and second arms when the actuation cannula is in the extended state.

17. The tissue engagement device of claim 1, wherein the first and second arms cross each other so as to cover at least a portion of a distal opening of the actuation cannula when the actuation cannula is in the retracted orientation, and wherein movement of the actuation cannula to the extended orientation moves the first and second arms to a position where they no longer cover the distal opening.

18. The tissue engagement device of claim 17, further comprising an access device having a tip, the access device being configured to pass through the actuation cannula when the actuation cannula is in the extended state; wherein the first piercing surface is at a distal tip of the first arm and the second piercing surface is at a distal tip of the second arm, and wherein the tip of the access device is configured to pass through a line that extends between the distal tips of the first and second arms when the actuation cannula is in the extended state.

* * * * *